(12) United States Patent
Watterson et al.

(10) Patent No.: US 11,951,358 B2
(45) Date of Patent: Apr. 9, 2024

(54) ENCODING EXERCISE MACHINE CONTROL COMMANDS IN SUBTITLE STREAMS

(71) Applicant: iFIT Inc., Logan, UT (US)

(72) Inventors: Eric Watterson, Logan, UT (US);
Chase Brammer, Providence, UT (US);
Christian Hathaway, Logan, UT (US);
Rebecca Capell, Logan, UT (US)

(73) Assignee: iFIT Inc., Logan, UT (US)

( * ) Notice: Subject to any disclaimer, the term of this patent is extended or adjusted under 35 U.S.C. 154(b) by 100 days.

(21) Appl. No.: 17/851,396

(22) Filed: Jun. 28, 2022

(65) Prior Publication Data

US 2022/0323827 A1 Oct. 13, 2022

Related U.S. Application Data

(63) Continuation of application No. 16/742,762, filed on Jan. 14, 2020, now Pat. No. 11,426,633.

(Continued)

(51) Int. Cl.
*A63B 24/00* (2006.01)
*A63B 22/00* (2006.01)
(Continued)

(52) U.S. Cl.
CPC ...... *A63B 24/0087* (2013.01); *A63B 22/0076* (2013.01); *A63B 22/025* (2015.10);
(Continued)

(58) Field of Classification Search
CPC ............... A63B 24/0087–2024/0096; A63B 71/0622–2071/0683
See application file for complete search history.

(56) References Cited

U.S. PATENT DOCUMENTS

| 3,123,646 A | 3/1964 | Easton |
| 3,579,339 A | 5/1971 | Chang et al. |

(Continued)

FOREIGN PATENT DOCUMENTS

| CN | 1447706 | 10/2003 |
| CN | 1828591 A | 9/2006 |

(Continued)

OTHER PUBLICATIONS

U.S. Appl. No. 63/316,890, filed Mar. 4, 2022, iFIT, Inc.

(Continued)

*Primary Examiner* — Jennifer Robertson
(74) *Attorney, Agent, or Firm* — Ray Quinney & Nebeker P.C.; Paul N. Taylor

(57) ABSTRACT

A method for controlling an exercise machine using a video workout program including encoding, remotely from the exercise machine, exercise machine control commands into a subtitle stream of a video to create the video workout program, wherein the exercise machine control commands are encoded at least once per second, decoding, locally to the exercise machine, the subtitle stream of the video to access the exercise machine control commands, displaying, locally to the exercise machine, the video, and controlling, locally to the exercise machine, one or more moveable members of the exercise machine using the exercise machine control commands.

20 Claims, 15 Drawing Sheets

Related U.S. Application Data

(60) Provisional application No. 62/866,576, filed on Jun. 25, 2019, provisional application No. 62/804,685, filed on Feb. 12, 2019.

(51) Int. Cl.
  A63B 22/02    (2006.01)
  A63B 22/06    (2006.01)
  A63B 71/06    (2006.01)

(52) U.S. Cl.
  CPC ...... *A63B 22/0605* (2013.01); *A63B 22/0664* (2013.01); *A63B 71/0622* (2013.01); *A63B 2024/0068* (2013.01); *A63B 2024/009* (2013.01); *A63B 2024/0093* (2013.01); *A63B 2071/0644* (2013.01); *A63B 2220/806* (2013.01); *A63B 2225/20* (2013.01); *A63B 2230/062* (2013.01)

(56) References Cited

U.S. PATENT DOCUMENTS

| | | |
|---|---|---|
| 4,023,795 A | 5/1977 | Pauls |
| 4,300,760 A | 11/1981 | Bobroff |
| 4,413,821 A | 11/1983 | Centafanti |
| D286,311 S | 10/1986 | Martinell et al. |
| 4,681,318 A | 7/1987 | Lay |
| 4,684,126 A | 8/1987 | Dalebout et al. |
| 4,705,028 A | 11/1987 | Melby |
| 4,728,102 A | 3/1988 | Pauls |
| 4,750,736 A | 6/1988 | Watterson |
| 4,796,881 A | 1/1989 | Watterson |
| 4,813,667 A | 3/1989 | Watterson |
| 4,830,371 A | 5/1989 | Lay |
| 4,844,451 A | 7/1989 | Bersonnet et al. |
| 4,850,585 A | 7/1989 | Dalebout |
| D304,849 S | 11/1989 | Watterson |
| 4,880,225 A | 11/1989 | Lucas et al. |
| 4,883,272 A | 11/1989 | Lay |
| D306,468 S | 3/1990 | Watterson |
| D306,891 S | 3/1990 | Watterson |
| 4,913,396 A | 4/1990 | Dalebout et al. |
| D307,614 S | 5/1990 | Bingham et al. |
| D307,615 S | 5/1990 | Bingham et al. |
| 4,921,242 A | 5/1990 | Watterson |
| 4,932,650 A | 6/1990 | Bingham et al. |
| D309,167 S | 7/1990 | Griffin |
| D309,485 S | 7/1990 | Bingham et al. |
| 4,938,478 A | 7/1990 | Lay |
| D310,253 S | 8/1990 | Bersonnet et al. |
| 4,955,599 A | 9/1990 | Bersonnet et al. |
| 4,971,316 A | 11/1990 | Dalebout et al. |
| D313,055 S | 12/1990 | Watterson |
| 4,974,832 A | 12/1990 | Dalebout |
| 4,979,737 A | 12/1990 | Kock |
| 4,981,294 A | 1/1991 | Dalebout et al. |
| D315,765 S | 3/1991 | Measom et al. |
| 4,998,725 A | 3/1991 | Watterson et al. |
| 5,000,442 A | 3/1991 | Dalebout et al. |
| 5,000,443 A | 3/1991 | Dalebout et al. |
| 5,000,444 A | 3/1991 | Dalebout et al. |
| D316,124 S | 4/1991 | Dalebout et al. |
| 5,013,033 A | 5/1991 | Watterson et al. |
| 5,014,980 A | 5/1991 | Bersonnet et al. |
| 5,016,871 A | 5/1991 | Dalebout et al. |
| D318,085 S | 7/1991 | Jacobson et al. |
| D318,086 S | 7/1991 | Bingham et al. |
| D318,699 S | 7/1991 | Jacobson et al. |
| 5,029,801 A | 7/1991 | Dalebout et al. |
| 5,034,576 A | 7/1991 | Dalebout et al. |
| 5,058,881 A | 10/1991 | Measom |
| 5,058,882 A | 10/1991 | Dalebout et al. |
| D321,388 S | 11/1991 | Dalebout |
| 5,062,626 A | 11/1991 | Dalebout et al. |
| 5,062,627 A | 11/1991 | Bingham |
| 5,062,632 A | 11/1991 | Dalebout et al. |
| 5,062,633 A | 11/1991 | Engel et al. |
| 5,067,710 A | 11/1991 | Watterson et al. |
| 5,072,929 A | 12/1991 | Peterson et al. |
| D323,009 S | 1/1992 | Dalebout et al. |
| D323,198 S | 1/1992 | Dalebout et al. |
| D323,199 S | 1/1992 | Dalebout et al. |
| D323,863 S | 2/1992 | Watterson |
| 5,088,729 A | 2/1992 | Dalebout |
| 5,090,694 A | 2/1992 | Pauls et al. |
| 5,102,380 A | 4/1992 | Jacobson et al. |
| 5,104,120 A | 4/1992 | Watterson et al. |
| 5,108,093 A | 4/1992 | Watterson |
| D326,491 S | 5/1992 | Dalebout |
| 5,122,105 A | 6/1992 | Engel et al. |
| 5,135,216 A | 8/1992 | Bingham et al. |
| 5,135,458 A | 8/1992 | Huang |
| 5,147,265 A | 9/1992 | Pauls et al. |
| 5,149,084 A | 9/1992 | Dalebout et al. |
| 5,149,312 A | 9/1992 | Croft et al. |
| 5,158,520 A | 10/1992 | Lemke |
| 5,171,196 A | 12/1992 | Lynch |
| D332,347 S | 1/1993 | Raadt et al. |
| 5,190,505 A | 3/1993 | Dalebout et al. |
| 5,192,255 A | 3/1993 | Dalebout et al. |
| 5,195,937 A | 3/1993 | Engel et al. |
| 5,203,826 A | 4/1993 | Dalebout |
| D335,511 S | 5/1993 | Engel et al. |
| D335,905 S | 5/1993 | Cutter et al. |
| D336,498 S | 6/1993 | Engel et al. |
| 5,217,487 A | 6/1993 | Engel et al. |
| D337,361 S | 7/1993 | Engel et al. |
| D337,666 S | 7/1993 | Peterson et al. |
| D337,799 S | 7/1993 | Cutter et al. |
| 5,226,866 A | 7/1993 | Engel et al. |
| 5,242,339 A | 9/1993 | Thornton |
| 5,244,446 A | 9/1993 | Engel et al. |
| 5,247,853 A | 9/1993 | Dalebout |
| 5,259,611 A | 11/1993 | Dalebout et al. |
| D342,106 S | 12/1993 | Campbell et al. |
| 5,279,528 A | 1/1994 | Dalebout et al. |
| D344,112 S | 2/1994 | Smith |
| D344,557 S | 2/1994 | Ashby |
| 5,282,776 A | 2/1994 | Dalebout |
| 5,295,931 A | 3/1994 | Dreibelbis et al. |
| 5,302,161 A | 4/1994 | Loubert et al. |
| D347,251 S | 5/1994 | Dreibelbis et al. |
| 5,316,534 A | 5/1994 | Dalebout et al. |
| D348,493 S | 7/1994 | Ashby |
| D348,494 S | 7/1994 | Ashby |
| 5,328,164 A | 7/1994 | Soga |
| D349,931 S | 8/1994 | Bostic et al. |
| 5,336,142 A | 8/1994 | Dalebout et al. |
| 5,344,376 A | 9/1994 | Bostic et al. |
| D351,202 S | 10/1994 | Bingham |
| D351,435 S | 10/1994 | Peterson et al. |
| D351,633 S | 10/1994 | Bingham |
| D352,534 S | 11/1994 | Dreibelbis et al. |
| D353,422 S | 12/1994 | Bostic et al. |
| 5,372,559 A | 12/1994 | Dalebout et al. |
| 5,374,228 A | 12/1994 | Buisman et al. |
| 5,382,221 A | 1/1995 | Hsu et al. |
| 5,385,520 A | 1/1995 | Lepine |
| 5,387,168 A | 2/1995 | Bostic |
| 5,393,690 A | 2/1995 | Fu et al. |
| D356,128 S | 3/1995 | Smith et al. |
| 5,409,435 A | 4/1995 | Daniels |
| 5,429,563 A | 7/1995 | Engel et al. |
| 5,431,612 A | 7/1995 | Holden |
| 5,461,612 A | 7/1995 | Holden |
| D360,915 S | 8/1995 | Bostic et al. |
| 5,468,205 A | 11/1995 | McFall et al. |
| 5,489,249 A | 2/1996 | Brewer et al. |
| 5,492,517 A | 2/1996 | Bostic et al. |
| D367,689 S | 3/1996 | Wilkinson et al. |
| 5,511,740 A | 4/1996 | Loubert et al. |
| 5,512,025 A | 4/1996 | Dalebout et al. |
| D370,949 S | 6/1996 | Furner |
| D371,176 S | 6/1996 | Furner |

(56) References Cited

U.S. PATENT DOCUMENTS

| | | |
|---|---|---|
| 5,527,245 A | 6/1996 | Dalebout et al. |
| 5,529,553 A | 6/1996 | Finlayson |
| 5,540,429 A | 7/1996 | Dalebout et al. |
| 5,549,533 A | 8/1996 | Olson et al. |
| 5,554,085 A | 9/1996 | Dalebout |
| 5,569,128 A | 10/1996 | Dalebout |
| 5,591,104 A | 1/1997 | Andrus et al. |
| 5,591,105 A | 1/1997 | Dalebout et al. |
| 5,591,106 A | 1/1997 | Dalebout et al. |
| 5,595,556 A | 1/1997 | Dalebout et al. |
| 5,607,375 A | 3/1997 | Dalebout et al. |
| 5,611,539 A | 3/1997 | Watterson et al. |
| 5,622,527 A | 4/1997 | Watterson et al. |
| 5,626,538 A | 5/1997 | Dalebout et al. |
| 5,626,540 A | 5/1997 | Hall |
| 5,626,542 A | 5/1997 | Dalebout et al. |
| D380,024 S | 6/1997 | Novak et al. |
| 5,637,059 A | 6/1997 | Dalebout |
| D380,509 S | 7/1997 | Wilkinson et al. |
| 5,643,153 A | 7/1997 | Nylen et al. |
| 5,645,509 A | 7/1997 | Brewer et al. |
| D384,118 S | 9/1997 | Deblauw |
| 5,662,557 A | 9/1997 | Watterson et al. |
| 5,667,461 A | 9/1997 | Hall |
| 5,669,857 A | 9/1997 | Watterson et al. |
| 5,672,140 A | 9/1997 | Watterson et al. |
| 5,674,156 A | 10/1997 | Watterson et al. |
| 5,674,453 A | 10/1997 | Watterson et al. |
| 5,676,624 A | 10/1997 | Watterson et al. |
| 5,683,331 A | 11/1997 | Dalebout |
| 5,683,332 A | 11/1997 | Watterson et al. |
| D387,825 S | 12/1997 | Fleck et al. |
| 5,695,433 A | 12/1997 | Buisman |
| 5,695,434 A | 12/1997 | Dalebout et al. |
| 5,695,435 A | 12/1997 | Dalebout et al. |
| 5,702,325 A | 12/1997 | Watterson et al. |
| 5,704,879 A | 1/1998 | Watterson et al. |
| 5,718,657 A | 2/1998 | Dalebout et al. |
| 5,720,200 A | 2/1998 | Anderson et al. |
| 5,720,698 A | 2/1998 | Dalebout et al. |
| D392,006 S | 3/1998 | Dalebout et al. |
| 5,722,922 A | 3/1998 | Watterson et al. |
| 5,733,229 A | 3/1998 | Dalebout et al. |
| 5,743,833 A | 4/1998 | Watterson et al. |
| 5,762,584 A | 6/1998 | Daniels |
| 5,762,587 A | 6/1998 | Dalebout et al. |
| 5,772,560 A | 6/1998 | Watterson et al. |
| 5,810,698 A | 9/1998 | Hullett et al. |
| 5,827,155 A | 10/1998 | Jensen et al. |
| 5,830,114 A | 11/1998 | Halfen et al. |
| 5,860,893 A | 1/1999 | Watterson et al. |
| 5,860,894 A | 1/1999 | Dalebout et al. |
| 5,899,834 A | 5/1999 | Dalebout et al. |
| 5,921,892 A | 7/1999 | Easton |
| D412,953 S | 8/1999 | Armstrong |
| D413,948 S | 9/1999 | Dalebout |
| 5,951,441 A | 9/1999 | Dalebout et al. |
| 5,951,448 A | 9/1999 | Bolland |
| D416,596 S | 11/1999 | Armstrong |
| 6,003,166 A | 12/1999 | Hald et al. |
| 6,019,710 A | 2/2000 | Dalebout et al. |
| 6,027,429 A | 2/2000 | Daniels |
| 6,033,347 A | 3/2000 | Dalebout et al. |
| D425,940 S | 5/2000 | Halfen et al. |
| 6,059,692 A | 5/2000 | Hickman |
| D428,949 S | 8/2000 | Simonson |
| 6,113,519 A | 9/2000 | Goto |
| 6,123,646 A | 9/2000 | Colassi |
| 6,171,217 B1 | 1/2001 | Cutler |
| 6,171,219 B1 | 1/2001 | Simonson |
| 6,174,267 B1 | 1/2001 | Dalebout et al. |
| 6,193,631 B1 | 2/2001 | Hickman |
| 6,228,003 B1 | 5/2001 | Hald et al. |
| 6,238,323 B1 | 5/2001 | Simonson |
| 6,251,052 B1 | 6/2001 | Simonson |
| 6,261,022 B1 | 7/2001 | Dalebout et al. |
| 6,280,362 B1 | 8/2001 | Dalebout et al. |
| 6,296,594 B1 | 10/2001 | Simonson |
| D450,872 S | 11/2001 | Dalebout et al. |
| 6,312,363 B1 | 11/2001 | Watterson et al. |
| D452,338 S | 12/2001 | Dalebout et al. |
| D453,543 S | 2/2002 | Cutler |
| D453,948 S | 2/2002 | Cutler |
| 6,350,218 B1 | 2/2002 | Dalebout et al. |
| 6,387,020 B1 | 5/2002 | Simonson |
| 6,413,191 B1 | 7/2002 | Harris et al. |
| 6,422,980 B1 | 7/2002 | Simonson |
| 6,447,424 B1 | 9/2002 | Ashby et al. |
| 6,458,060 B1 | 10/2002 | Watterson et al. |
| 6,458,061 B2 | 10/2002 | Simonson |
| 6,471,622 B1 | 10/2002 | Hammer et al. |
| 6,506,142 B2 | 1/2003 | Itoh |
| 6,527,678 B1 | 3/2003 | Wang |
| 6,547,698 B2 | 4/2003 | Inagawa |
| 6,563,225 B2 | 5/2003 | Soga et al. |
| 6,601,016 B1 | 7/2003 | Brown et al. |
| 6,623,140 B2 | 9/2003 | Watterson et al. |
| 6,626,799 B2 | 9/2003 | Watterson |
| 6,652,424 B2 | 11/2003 | Dalebout |
| 6,685,607 B1 | 2/2004 | Olson |
| 6,695,581 B2 | 2/2004 | Wasson et al. |
| 6,701,271 B2 | 3/2004 | Willner et al. |
| 6,702,719 B1 | 3/2004 | Brown et al. |
| 6,712,740 B2 | 3/2004 | Simonson |
| 6,719,667 B2 | 4/2004 | Wong |
| 6,730,002 B2 | 5/2004 | Hald et al. |
| 6,743,153 B2 | 6/2004 | Watterson et al. |
| 6,746,371 B1 | 6/2004 | Brown et al. |
| 6,749,537 B1 | 6/2004 | Hickman |
| 6,761,667 B1 | 7/2004 | Cutler et al. |
| 6,770,015 B2 | 8/2004 | Simonson |
| 6,783,482 B2 | 8/2004 | Oglesby |
| 6,786,852 B2 | 9/2004 | Watterson et al. |
| 6,796,925 B2 | 9/2004 | Martinez |
| 6,808,472 B1 | 10/2004 | Hickman |
| 6,821,230 B2 | 11/2004 | Dalebout et al. |
| 6,830,540 B2 | 12/2004 | Watterson et al. |
| 6,863,641 B1 | 3/2005 | Brown et al. |
| 6,866,613 B1 | 3/2005 | Brown et al. |
| 6,875,160 B2 | 4/2005 | Watterson et al. |
| 6,878,101 B2 | 4/2005 | Colley |
| D507,311 S | 7/2005 | Butler et al. |
| 6,918,858 B2 | 7/2005 | Watterson |
| 6,921,351 B1 | 7/2005 | Hickman et al. |
| 6,974,404 B1 | 12/2005 | Watterson et al. |
| 6,997,852 B2 | 2/2006 | Watterson et al. |
| 7,025,713 B2 | 4/2006 | Dalebout et al. |
| D520,085 S | 5/2006 | Willardson et al. |
| 7,044,897 B2 | 5/2006 | Myers et al. |
| 7,052,442 B2 | 5/2006 | Watterson et al. |
| 7,060,006 B1 | 6/2006 | Watterson et al. |
| 7,060,008 B2 | 6/2006 | Watterson et al. |
| 7,070,539 B2 | 7/2006 | Brown et al. |
| 7,070,542 B2 | 7/2006 | Reyes |
| 7,097,588 B2 | 8/2006 | Watterson et al. |
| D527,776 S | 9/2006 | Willardson et al. |
| 7,112,168 B2 | 9/2006 | Dalebout et al. |
| 7,125,369 B2 | 10/2006 | Endelman |
| 7,128,693 B2 | 10/2006 | Brown et al. |
| 7,132,939 B2 | 11/2006 | Tyndall |
| 7,153,240 B1 | 12/2006 | Wu |
| 7,166,062 B1 | 1/2007 | Watterson et al. |
| 7,166,064 B2 | 1/2007 | Watterson et al. |
| 7,169,087 B2 | 1/2007 | Ercanbrack et al. |
| 7,169,093 B2 | 1/2007 | Simonson et al. |
| 7,172,536 B2 | 2/2007 | Liu |
| 7,192,387 B2 | 3/2007 | Mendel |
| 7,192,388 B2 | 3/2007 | Dalebout et al. |
| 7,250,022 B2 | 7/2007 | Dalebout et al. |
| 7,282,016 B2 | 10/2007 | Simonson |
| 7,285,075 B2 | 10/2007 | Cutler et al. |
| 7,344,481 B2 | 3/2008 | Watterson et al. |
| 7,377,882 B2 | 5/2008 | Watterson et al. |
| 7,425,188 B2 | 9/2008 | Ercanbrack et al. |

(56) References Cited

U.S. PATENT DOCUMENTS

| | | |
|---|---|---|
| 7,429,236 B2 | 9/2008 | Dalebout et al. |
| 7,452,311 B2 | 11/2008 | Barnes |
| 7,455,622 B2 | 11/2008 | Watterson et al. |
| 7,470,219 B2 | 12/2008 | Larson |
| 7,482,050 B2 | 1/2009 | Olson |
| D588,655 S | 3/2009 | Utykanski |
| 7,510,509 B2 | 3/2009 | Hickman |
| 7,537,546 B2 | 5/2009 | Watterson et al. |
| 7,537,549 B2 | 5/2009 | Nelson et al. |
| 7,537,552 B2 | 5/2009 | Dalebout et al. |
| 7,540,828 B2 | 6/2009 | Watterson et al. |
| 7,549,947 B2 | 6/2009 | Hickman et al. |
| 7,556,590 B2 | 7/2009 | Watterson et al. |
| 7,563,203 B2 | 7/2009 | Dalebout et al. |
| 7,575,536 B1 | 8/2009 | Hickman |
| 7,578,771 B1 | 8/2009 | Towley, III et al. |
| 7,601,105 B1 | 10/2009 | Gipson et al. |
| 7,604,573 B2 | 10/2009 | Dalebout et al. |
| D604,373 S | 11/2009 | Dalebout et al. |
| 7,618,350 B2 | 11/2009 | Dalebout et al. |
| 7,618,357 B2 | 11/2009 | Dalebout et al. |
| 7,625,315 B2 | 12/2009 | Hickman |
| 7,625,321 B2 | 12/2009 | Simonson et al. |
| 7,628,730 B1 | 12/2009 | Watterson et al. |
| 7,628,737 B2 | 12/2009 | Kowallis et al. |
| 7,631,338 B2 | 12/2009 | Del Sesto et al. |
| 7,637,847 B1 | 12/2009 | Hickman |
| 7,645,212 B2 | 1/2010 | Ashby et al. |
| 7,645,213 B2 | 1/2010 | Watterson et al. |
| 7,658,698 B2 | 2/2010 | Pacheco et al. |
| 7,674,205 B2 | 3/2010 | Dalebout et al. |
| 7,713,171 B1 | 5/2010 | Hickman |
| 7,713,172 B2 | 5/2010 | Watterson et al. |
| 7,713,180 B2 | 5/2010 | Wickens et al. |
| 7,717,828 B2 | 5/2010 | Simonson et al. |
| 7,736,279 B2 | 6/2010 | Dalebout et al. |
| 7,740,563 B2 | 6/2010 | Dalebout et al. |
| 7,749,144 B2 | 7/2010 | Hammer |
| 7,766,797 B2 | 8/2010 | Dalebout et al. |
| 7,771,320 B2 | 8/2010 | Riley |
| 7,771,329 B2 | 8/2010 | Dalebout |
| 7,775,940 B2 | 8/2010 | Dalebout et al. |
| 7,789,800 B1 | 9/2010 | Watterson et al. |
| 7,798,946 B2 | 9/2010 | Dalebout et al. |
| 7,806,589 B2 | 10/2010 | Tashman |
| 7,815,548 B2 | 10/2010 | Barre |
| 7,815,550 B2 | 10/2010 | Watterson et al. |
| 7,857,731 B2 | 12/2010 | Hickman et al. |
| 7,862,475 B2 | 1/2011 | Watterson et al. |
| 7,862,478 B2 | 1/2011 | Watterson et al. |
| 7,862,483 B2 | 1/2011 | Hendrickson et al. |
| 7,862,489 B2 | 1/2011 | Saysek |
| 7,887,470 B2 | 2/2011 | Chen |
| D635,207 S | 3/2011 | Dalebout et al. |
| 7,901,324 B2 | 3/2011 | Kodama |
| 7,901,330 B2 | 3/2011 | Dalebout et al. |
| 7,909,740 B2 | 3/2011 | Dalebout et al. |
| 7,980,996 B2 | 7/2011 | Hickman |
| 7,981,000 B2 | 7/2011 | Watterson et al. |
| 7,985,164 B2 | 7/2011 | Ashby |
| 8,007,409 B2 | 8/2011 | Ellis |
| 8,029,415 B2 | 10/2011 | Ashby et al. |
| 8,033,960 B1 | 10/2011 | Dalebout et al. |
| D650,451 S | 12/2011 | Olson et al. |
| 8,075,453 B1 | 12/2011 | Wilkinson |
| D652,877 S | 1/2012 | Dalebout et al. |
| 8,152,702 B2 | 4/2012 | Pacheco |
| 8,157,708 B2 | 4/2012 | Daly |
| D659,775 S | 5/2012 | Olson et al. |
| D659,777 S | 5/2012 | Watterson et al. |
| D660,383 S | 5/2012 | Watterson et al. |
| D664,613 S | 7/2012 | Dalebout et al. |
| 8,251,874 B2 | 8/2012 | Ashby et al. |
| 8,257,232 B2 | 9/2012 | Albert |
| 8,298,123 B2 | 10/2012 | Hickman |
| 8,298,125 B2 | 10/2012 | Colledge et al. |
| D671,177 S | 11/2012 | Sip |
| D671,178 S | 11/2012 | Sip |
| 8,308,618 B2 | 11/2012 | Bayerlein |
| D673,626 S | 1/2013 | Olson et al. |
| 8,608,624 B2 | 12/2013 | Shabodyash |
| 8,690,735 B2 | 4/2014 | Watterson et al. |
| D707,763 S | 6/2014 | Cutler |
| 8,740,753 B2 | 6/2014 | Olson et al. |
| 8,747,285 B2 | 6/2014 | Hof |
| 8,758,201 B2 | 6/2014 | Ashby et al. |
| 8,771,153 B2 | 7/2014 | Dalebout et al. |
| 8,784,115 B1 | 7/2014 | Chuang |
| 8,784,270 B2 | 7/2014 | Ashby et al. |
| 8,784,275 B2 | 7/2014 | Mikan |
| 8,784,278 B2 | 7/2014 | Flake |
| 8,808,148 B2 | 8/2014 | Watterson et al. |
| 8,814,762 B2 | 8/2014 | Butler et al. |
| D712,493 S | 9/2014 | Ercanbrack et al. |
| 8,840,075 B2 | 9/2014 | Dalebout et al. |
| 8,845,493 B2 | 9/2014 | Watterson et al. |
| 8,870,726 B2 | 10/2014 | Watterson et al. |
| 8,876,668 B2 | 11/2014 | Hendrickson et al. |
| 8,894,549 B2 | 11/2014 | Colledge |
| 8,894,555 B2 | 11/2014 | Colledge et al. |
| 8,911,330 B2 | 12/2014 | Watterson et al. |
| 8,920,288 B2 | 12/2014 | Dalebout et al. |
| 8,920,347 B2 | 12/2014 | Bayerlein |
| 8,979,709 B2 | 3/2015 | Toback |
| 8,986,165 B2 | 3/2015 | Ashby |
| 8,992,364 B2 | 3/2015 | Law et al. |
| 8,992,387 B2 | 3/2015 | Watterson et al. |
| D726,476 S | 4/2015 | Ercanbrack |
| 9,028,368 B2 | 5/2015 | Ashby et al. |
| 9,028,370 B2 | 5/2015 | Watterson et al. |
| 9,039,578 B2 | 5/2015 | Dalebout |
| D731,011 S | 6/2015 | Buchanan |
| 9,072,930 B2 | 7/2015 | Ashby et al. |
| 9,119,983 B2 | 9/2015 | Rhea |
| 9,119,988 B2 | 9/2015 | Murray |
| 9,123,317 B2 | 9/2015 | Watterson et al. |
| 9,126,071 B2 | 9/2015 | Smith |
| 9,126,072 B2 | 9/2015 | Watterson |
| 9,138,615 B2 | 9/2015 | Olson et al. |
| 9,142,139 B2 | 9/2015 | Watterson et al. |
| 9,144,703 B2 | 9/2015 | Dalebout et al. |
| 9,149,683 B2 | 10/2015 | Watterson et al. |
| 9,186,535 B2 | 11/2015 | Ercanbrack |
| 9,186,549 B2 | 11/2015 | Watterson et al. |
| 9,186,552 B1 | 11/2015 | Deal |
| 9,227,101 B2 | 1/2016 | Maguire |
| 9,233,272 B2 | 1/2016 | Villani |
| 9,254,409 B2 | 2/2016 | Dalebout et al. |
| 9,254,416 B2 | 2/2016 | Ashby |
| 9,278,248 B2 | 3/2016 | Tyger et al. |
| 9,278,249 B2 | 3/2016 | Watterson |
| 9,278,250 B2 | 3/2016 | Buchanan |
| 9,289,648 B2 | 3/2016 | Watterson |
| 9,292,935 B2 | 3/2016 | Koduri et al. |
| 9,308,417 B2 | 4/2016 | Grundy |
| 9,339,683 B2 | 5/2016 | Dilli |
| 9,339,691 B2 | 5/2016 | Brammer |
| 9,352,185 B2 | 5/2016 | Hendrickson et al. |
| 9,352,186 B2 | 5/2016 | Watterson |
| 9,364,714 B2 | 6/2016 | Koduri et al. |
| 9,375,605 B2 | 6/2016 | Tyger et al. |
| 9,378,336 B2 | 6/2016 | Ohnemus |
| 9,381,394 B2 | 7/2016 | Mortensen et al. |
| 9,387,387 B2 | 7/2016 | Dalebout |
| 9,393,453 B2 | 7/2016 | Watterson |
| 9,403,047 B2 | 8/2016 | Olson et al. |
| 9,403,051 B2 | 8/2016 | Cutler |
| 9,421,416 B2 | 8/2016 | Mortensen et al. |
| 9,457,219 B2 | 10/2016 | Smith |
| 9,457,220 B2 | 10/2016 | Olson |
| 9,457,222 B2 | 10/2016 | Dalebout |
| 9,460,632 B2 | 10/2016 | Watterson |
| 9,463,356 B2 | 10/2016 | Rhea |
| 9,468,794 B2 | 10/2016 | Barton |

(56) References Cited

U.S. PATENT DOCUMENTS

| | | |
|---|---|---|
| 9,468,798 B2 | 10/2016 | Dalebout |
| 9,480,874 B2 | 11/2016 | Cutler |
| 9,492,704 B2 | 11/2016 | Mortensen et al. |
| 9,498,668 B2 | 11/2016 | Smith |
| 9,517,378 B2 | 12/2016 | Ashby et al. |
| 9,521,901 B2 | 12/2016 | Dalebout |
| 9,533,187 B2 | 1/2017 | Dalebout |
| 9,539,461 B2 | 1/2017 | Ercanbrack |
| 9,550,091 B2 | 1/2017 | Emerson |
| 9,579,544 B2 | 2/2017 | Watterson |
| 9,586,086 B2 | 3/2017 | Dalebout et al. |
| 9,586,090 B2 | 3/2017 | Watterson et al. |
| 9,604,099 B2 | 3/2017 | Taylor |
| 9,616,276 B2 | 4/2017 | Dalebout et al. |
| 9,616,278 B2 | 4/2017 | Olson |
| 9,623,281 B2 | 4/2017 | Hendrickson et al. |
| 9,636,567 B2 | 5/2017 | Brammer et al. |
| 9,675,839 B2 | 6/2017 | Dalebout et al. |
| 9,682,307 B2 | 6/2017 | Dalebout |
| 9,694,234 B2 | 7/2017 | Dalebout et al. |
| 9,694,242 B2 | 7/2017 | Ashby et al. |
| 9,737,755 B2 | 8/2017 | Dalebout |
| 9,750,454 B2 | 9/2017 | Walke |
| 9,757,605 B2 | 9/2017 | Olson et al. |
| 9,764,186 B2 | 9/2017 | Dalebout et al. |
| 9,767,785 B2 | 9/2017 | Ashby et al. |
| 9,776,032 B2 | 10/2017 | Moran |
| 9,795,822 B2 | 10/2017 | Smith et al. |
| 9,795,855 B2 | 10/2017 | Jafarifesharaki |
| 9,808,672 B2 | 11/2017 | Dalebout |
| 9,849,326 B2 | 12/2017 | Smith |
| 9,878,210 B2 | 1/2018 | Watterson |
| 9,889,334 B2 | 2/2018 | Ashby et al. |
| 9,889,339 B2 | 2/2018 | Douglass |
| 9,937,376 B2 | 4/2018 | McInelly et al. |
| 9,937,377 B2 | 4/2018 | McInelly et al. |
| 9,937,378 B2 | 4/2018 | Dalebout et al. |
| 9,937,379 B2 | 4/2018 | Mortensen et al. |
| 9,943,719 B2 | 4/2018 | Smith et al. |
| 9,943,722 B2 | 4/2018 | Dalebout |
| 9,948,037 B2 | 4/2018 | Ashby |
| 9,968,816 B2 | 5/2018 | Olson et al. |
| 9,968,821 B2 | 5/2018 | Finlayson et al. |
| 9,968,823 B2 | 5/2018 | Cutler |
| 9,980,465 B2 | 5/2018 | Hayashi |
| 10,010,755 B2 | 7/2018 | Watterson |
| 10,010,756 B2 | 7/2018 | Watterson |
| 10,029,145 B2 | 7/2018 | Douglass |
| D826,350 S | 8/2018 | Hochstrasser |
| 10,046,196 B2 | 8/2018 | Ercanbrack et al. |
| D827,733 S | 9/2018 | Hochstrasser |
| 10,065,064 B2 | 9/2018 | Smith et al. |
| 10,071,285 B2 | 9/2018 | Smith et al. |
| 10,085,586 B2 | 10/2018 | Smith et al. |
| 10,086,254 B2 | 10/2018 | Watterson |
| 10,118,064 B1 | 11/2018 | Cox |
| 10,136,842 B2 | 11/2018 | Ashby |
| 10,186,161 B2 | 1/2019 | Watterson |
| 10,188,890 B2 | 1/2019 | Olson et al. |
| 10,207,143 B2 | 2/2019 | Dalebout et al. |
| 10,207,145 B2 | 2/2019 | Tyger et al. |
| 10,207,147 B2 | 2/2019 | Ercanbrack et al. |
| 10,207,148 B2 | 2/2019 | Powell et al. |
| 10,212,994 B2 | 2/2019 | Watterson et al. |
| 10,220,259 B2 | 3/2019 | Brammer |
| 10,226,396 B2 | 3/2019 | Ashby |
| 10,226,664 B2 | 3/2019 | Dalebout et al. |
| 10,252,109 B2 | 4/2019 | Watterson |
| 10,258,828 B2 | 4/2019 | Dalebout et al. |
| 10,272,317 B2 | 4/2019 | Watterson |
| 10,279,212 B2 | 5/2019 | Dalebout et al. |
| 10,293,211 B2 | 5/2019 | Watterson et al. |
| D852,292 S | 6/2019 | Cutler |
| 10,343,017 B2 | 7/2019 | Jackson |
| 10,376,736 B2 | 8/2019 | Powell et al. |
| 10,388,183 B2 | 8/2019 | Watterson |
| 10,391,361 B2 | 8/2019 | Watterson |
| D864,320 S | 10/2019 | Weston |
| D864,321 S | 10/2019 | Weston |
| 10,426,989 B2 | 10/2019 | Dalebout |
| 10,433,612 B2 | 10/2019 | Ashby et al. |
| 10,441,840 B2 | 10/2019 | Dalebout |
| 10,441,844 B2 | 10/2019 | Powell |
| 10,449,416 B2 | 10/2019 | Dalebout et al. |
| 10,471,299 B2 | 11/2019 | Powell |
| D868,909 S | 12/2019 | Cutler et al. |
| 10,492,519 B2 | 12/2019 | Capell et al. |
| 10,493,349 B2 | 12/2019 | Watterson |
| 10,500,473 B2 | 12/2019 | Watterson |
| 10,537,764 B2 | 1/2020 | Smith et al. |
| 10,543,395 B2 | 1/2020 | Powell et al. |
| 10,561,877 B2 | 2/2020 | Workman |
| 10,561,893 B2 | 2/2020 | Chatterton et al. |
| 10,561,894 B2 | 2/2020 | Dalebout et al. |
| 10,569,121 B2 | 2/2020 | Watterson |
| 10,569,123 B2 | 2/2020 | Hochstrasser et al. |
| 10,625,114 B2 | 4/2020 | Ercanbrack |
| 10,625,137 B2 | 4/2020 | Dalebout et al. |
| 10,661,114 B2 | 5/2020 | Watterson et al. |
| 10,668,320 B2 | 6/2020 | Watterson |
| 10,671,705 B2 | 6/2020 | Capell et al. |
| 10,688,346 B2 | 6/2020 | Brammer |
| 10,702,736 B2 | 7/2020 | Weston et al. |
| 10,709,925 B2 | 7/2020 | Dalebout et al. |
| 10,726,730 B2 | 7/2020 | Watterson |
| 10,729,965 B2 | 8/2020 | Powell |
| 10,758,767 B2 | 9/2020 | Olson et al. |
| 10,786,706 B2 | 9/2020 | Smith |
| 10,864,407 B2 | 12/2020 | Watterson et al. |
| 10,918,905 B2 | 2/2021 | Powell et al. |
| 10,932,517 B2 | 3/2021 | Ashby et al. |
| 10,940,360 B2 | 3/2021 | Dalebout et al. |
| 10,953,268 B1 | 3/2021 | Dalebout et al. |
| 10,953,305 B2 | 3/2021 | Dalebout et al. |
| 10,967,214 B1 | 4/2021 | Olson et al. |
| 10,994,173 B2 | 5/2021 | Watterson |
| 11,000,730 B2 | 5/2021 | Dalebout et al. |
| 11,013,960 B2 | 5/2021 | Watterson et al. |
| 11,033,777 B1 | 6/2021 | Watterson et al. |
| 11,058,913 B2 | 7/2021 | Dalebout et al. |
| 11,058,914 B2 | 7/2021 | Powell |
| 11,058,918 B1 | 7/2021 | Watterson et al. |
| 11,187,285 B2 | 11/2021 | Wrobel |
| 11,298,577 B2 | 4/2022 | Watterson |
| 11,326,673 B2 | 5/2022 | Buchanan |
| 11,338,169 B2 | 5/2022 | Dalebout et al. |
| 11,338,175 B2 | 5/2022 | Watterson et al. |
| 11,426,633 B2 | 8/2022 | Watterson et al. |
| 11,451,108 B2 | 9/2022 | Tinney |
| 11,452,903 B2 | 9/2022 | Watterson |
| 11,511,152 B2 | 11/2022 | Powell et al. |
| 11,534,651 B2 | 12/2022 | Ercanbrack et al. |
| 11,534,654 B2 | 12/2022 | Silcock et al. |
| 11,534,655 B2 | 12/2022 | Dalebout et al. |
| 11,565,148 B2 | 1/2023 | Dalebout et al. |
| 11,596,830 B2 | 3/2023 | Dalebout et al. |
| 11,642,564 B2 | 5/2023 | Watterson |
| 11,673,036 B2 | 6/2023 | Dalebout et al. |
| 11,680,611 B2 | 6/2023 | Wrobel |
| 11,700,905 B2 | 7/2023 | Ashby et al. |
| 2002/0016235 A1 | 2/2002 | Ashby |
| 2002/0022551 A1 | 2/2002 | Watterson |
| 2002/0077221 A1 | 6/2002 | Dalebout |
| 2002/0128127 A1 | 9/2002 | Chen |
| 2002/0159253 A1 | 10/2002 | Dalebout |
| 2003/0045406 A1 | 3/2003 | Stone |
| 2003/0171189 A1 | 9/2003 | Kaufman |
| 2004/0091307 A1 | 5/2004 | James |
| 2004/0171464 A1 | 9/2004 | Ashby |
| 2004/0171465 A1 | 9/2004 | Hald |
| 2004/0189722 A1 | 9/2004 | Acres |
| 2005/0049123 A1 | 3/2005 | Dalebout |
| 2005/0077805 A1 | 4/2005 | Dalebout |
| 2005/0107229 A1 | 5/2005 | Wickens |

(56) References Cited

U.S. PATENT DOCUMENTS

| | | |
|---|---|---|
| 2005/0164839 A1 | 7/2005 | Watterson |
| 2005/0272577 A1 | 12/2005 | Olson |
| 2005/0277520 A1 | 12/2005 | Van Waes |
| 2006/0135322 A1 | 6/2006 | Rocker |
| 2006/0217237 A1 | 9/2006 | Rhodes |
| 2006/0240959 A1 | 10/2006 | Huang |
| 2007/0042868 A1 | 2/2007 | Fisher et al. |
| 2007/0066448 A1 | 3/2007 | Pan |
| 2007/0117683 A1 | 5/2007 | Ercanbrack |
| 2007/0197353 A1 | 8/2007 | Hundley |
| 2007/0254778 A1 | 11/2007 | Ashby |
| 2008/0051256 A1 | 2/2008 | Ashby |
| 2008/0242520 A1 | 10/2008 | Hubbard |
| 2008/0300110 A1 | 12/2008 | Smith |
| 2009/0105052 A1 | 4/2009 | Dalebout |
| 2010/0004097 A1 | 1/2010 | D'Eredita |
| 2010/0242246 A1 | 9/2010 | Dalebout |
| 2010/0317488 A1 | 12/2010 | Cartaya |
| 2011/0131005 A1 | 6/2011 | Ueshirna |
| 2012/0237911 A1 | 9/2012 | Watterson |
| 2012/0264570 A1 | 10/2012 | Watterson et al. |
| 2012/0295774 A1 | 11/2012 | Dalebout |
| 2013/0014321 A1 | 1/2013 | Sullivan |
| 2013/0123071 A1 | 5/2013 | Rhea |
| 2013/0123083 A1 | 5/2013 | Sip |
| 2013/0165195 A1 | 6/2013 | Watterson |
| 2013/0178337 A1 | 6/2013 | Brammer |
| 2013/0172152 A1 | 7/2013 | Watterson |
| 2013/0172153 A1 | 7/2013 | Watterson |
| 2013/0178334 A1 | 7/2013 | Brammer |
| 2013/0178768 A1 | 7/2013 | Dalebout |
| 2013/0190136 A1 | 7/2013 | Watterson |
| 2013/0196298 A1 | 8/2013 | Watterson |
| 2013/0196821 A1 | 8/2013 | Watterson |
| 2013/0196822 A1 | 8/2013 | Watterson |
| 2013/0218585 A1 | 8/2013 | Watterson |
| 2013/0244836 A1 | 9/2013 | Maughan |
| 2013/0267383 A1 | 10/2013 | Watterson |
| 2013/0268101 A1 | 10/2013 | Brammer |
| 2013/0274067 A1 | 10/2013 | Watterson |
| 2013/0281241 A1 | 10/2013 | Watterson |
| 2014/0024499 A1 | 1/2014 | Watterson |
| 2014/0073970 A1 | 3/2014 | Ashby |
| 2014/0121071 A1 | 5/2014 | Strom |
| 2014/0135173 A1 | 5/2014 | Watterson |
| 2014/0274574 A1 | 9/2014 | Shorten |
| 2014/0274579 A1 | 9/2014 | Olson |
| 2014/0287884 A1 | 9/2014 | Buchanan |
| 2014/0309085 A1 | 10/2014 | Watterson |
| 2015/0018990 A1 | 1/2015 | Shachar et al. |
| 2015/0182779 A1 | 7/2015 | Dalebout |
| 2015/0182781 A1 | 7/2015 | Watterson |
| 2015/0238817 A1 | 8/2015 | Watterson |
| 2015/0250418 A1 | 9/2015 | Ashby |
| 2015/0251055 A1 | 9/2015 | Ashby |
| 2015/0253210 A1 | 9/2015 | Ashby et al. |
| 2015/0253735 A1 | 9/2015 | Watterson |
| 2015/0253736 A1 | 9/2015 | Watterson |
| 2015/0258560 A1 | 9/2015 | Ashby |
| 2015/0343264 A1 | 12/2015 | Rhea |
| 2015/0360083 A1 | 12/2015 | Lagree |
| 2015/0367161 A1 | 12/2015 | Wiegardt |
| 2016/0058335 A1 | 3/2016 | Ashby |
| 2016/0063615 A1 | 3/2016 | Watterson |
| 2016/0092909 A1 | 3/2016 | Watterson |
| 2016/0101311 A1 | 4/2016 | Workman |
| 2016/0107065 A1 | 4/2016 | Brammer |
| 2016/0121074 A1 | 5/2016 | Ashby |
| 2016/0148535 A1 | 5/2016 | Ashby |
| 2016/0148536 A1 | 5/2016 | Ashby |
| 2016/0158595 A1 | 6/2016 | Dalebout |
| 2016/0206248 A1 | 7/2016 | Sartor et al. |
| 2016/0206922 A1 | 7/2016 | Dalebout et al. |
| 2016/0250519 A1 | 9/2016 | Watterson |
| 2016/0253918 A1 | 9/2016 | Watterson |
| 2016/0339298 A1 | 11/2016 | Kats |
| 2016/0346595 A1 | 12/2016 | Dalebout et al. |
| 2016/0346609 A1 | 12/2016 | Bailly et al. |
| 2016/0346617 A1 | 12/2016 | Srugo et al. |
| 2017/0006338 A1 | 1/2017 | Kim et al. |
| 2017/0036053 A1 | 2/2017 | Smith |
| 2017/0056711 A1 | 3/2017 | Dalebout |
| 2017/0056715 A1 | 3/2017 | Dalebout |
| 2017/0056726 A1 | 3/2017 | Dalebout et al. |
| 2017/0124912 A1 | 5/2017 | Ashby |
| 2017/0193578 A1 | 7/2017 | Watterson |
| 2017/0266483 A1 | 9/2017 | Dalebout |
| 2017/0266489 A1 | 9/2017 | Douglass |
| 2017/0266532 A1 | 9/2017 | Watterson |
| 2017/0266533 A1 | 9/2017 | Dalebout |
| 2017/0270820 A1 | 9/2017 | Ashby |
| 2017/0274248 A1 | 9/2017 | Brown et al. |
| 2017/0316425 A1 | 11/2017 | Ackland et al. |
| 2018/0001135 A1 | 1/2018 | Powell |
| 2018/0036585 A1 | 2/2018 | Powell |
| 2018/0071610 A1 | 3/2018 | Miller |
| 2018/0084817 A1 | 3/2018 | Capell et al. |
| 2018/0085630 A1 | 3/2018 | Capell |
| 2018/0089396 A1 | 3/2018 | Capell |
| 2018/0099116 A1 | 4/2018 | Ashby |
| 2018/0099179 A1 | 4/2018 | Chatterton |
| 2018/0099180 A1 | 4/2018 | Wilkinson |
| 2018/0099205 A1 | 4/2018 | Watterson |
| 2018/0111034 A1 | 4/2018 | Watterson |
| 2018/0117383 A1 | 5/2018 | Workman |
| 2018/0117385 A1 | 5/2018 | Watterson |
| 2018/0117393 A1 | 5/2018 | Ercanbrack |
| 2018/0140903 A1 | 5/2018 | Poure et al. |
| 2018/0154205 A1 | 6/2018 | Watterson |
| 2018/0154207 A1 | 6/2018 | Hochstrasser |
| 2018/0154208 A1 | 6/2018 | Powell et al. |
| 2018/0154209 A1 | 6/2018 | Watterson |
| 2018/0200566 A1 | 7/2018 | Weston |
| 2018/0330630 A1 | 11/2018 | Klein et al. |
| 2019/0058370 A1 | 2/2019 | Tinney |
| 2019/0080624 A1 | 3/2019 | Watterson |
| 2019/0111318 A1 * | 4/2019 | Evancha ............ A63B 24/0087 |
| 2019/0143193 A1 | 5/2019 | Kim |
| 2019/0151698 A1 | 5/2019 | Olson |
| 2019/0168072 A1 | 6/2019 | Brammer |
| 2019/0178313 A1 | 6/2019 | Wrobel |
| 2019/0192898 A1 | 6/2019 | Dalebout |
| 2019/0192952 A1 | 6/2019 | Powell |
| 2019/0209893 A1 | 7/2019 | Watterson |
| 2019/0223612 A1 | 7/2019 | Watterson |
| 2019/0232112 A1 | 8/2019 | Dalebout |
| 2019/0269958 A1 | 9/2019 | Dalebout |
| 2019/0269971 A1 | 9/2019 | Capell |
| 2019/0275366 A1 | 9/2019 | Powell |
| 2019/0282852 A1 | 9/2019 | Dalebout |
| 2019/0328079 A1 | 10/2019 | Ashby |
| 2019/0329091 A1 | 10/2019 | Powell |
| 2019/0336827 A1 | 11/2019 | Intonato et al. |
| 2019/0376585 A1 | 12/2019 | Buchanan |
| 2020/0009417 A1 | 1/2020 | Dalebout |
| 2020/0016459 A1 | 1/2020 | Smith |
| 2020/0047027 A1 | 2/2020 | Ward et al. |
| 2020/0047031 A1 * | 2/2020 | Orady ................ A63B 24/0062 |
| 2020/0254311 A1 | 8/2020 | Waterson et al. |
| 2020/0368575 A1 | 11/2020 | Hays et al. |
| 2020/0391069 A1 | 12/2020 | Olson et al. |
| 2021/0001177 A1 | 1/2021 | Smith |
| 2021/0001205 A1 | 1/2021 | Kim |
| 2021/0046353 A1 | 2/2021 | Dalebout et al. |
| 2021/0106899 A1 | 4/2021 | Willardson et al. |
| 2021/0110910 A1 | 4/2021 | Ostler et al. |
| 2021/0146221 A1 | 5/2021 | Dalebout et al. |
| 2021/0213331 A1 | 7/2021 | Watterson |
| 2021/0268336 A1 | 9/2021 | Watterson et al. |
| 2021/0291013 A1 | 9/2021 | Nascimento |
| 2021/0299518 A1 | 9/2021 | Brammer et al. |
| 2021/0299542 A1 | 9/2021 | Brammer et al. |
| 2021/0339079 A1 | 11/2021 | Dalebout et al. |
| 2022/0062685 A1 | 3/2022 | Ashby et al. |

(56) References Cited

U.S. PATENT DOCUMENTS

| | | |
|---|---|---|
| 2022/0074455 A1 | 3/2022 | Wrobel |
| 2022/0104992 A1 | 4/2022 | Ashby |
| 2022/0212052 A1 | 7/2022 | Ercanbrack et al. |
| 2022/0241649 A1 | 8/2022 | Ashby |
| 2022/0241665 A1 | 8/2022 | Dalebout et al. |
| 2022/0241668 A1 | 8/2022 | Willardson et al. |
| 2022/0249912 A1 | 8/2022 | Watterson et al. |
| 2022/0257994 A1 | 8/2022 | Smith |
| 2022/0258007 A1 | 8/2022 | Watterson et al. |
| 2022/0258008 A1 | 8/2022 | Watterson et al. |
| 2022/0266085 A1 | 8/2022 | Dalebout et al. |
| 2022/0280857 A1 | 9/2022 | Watterson |
| 2022/0309042 A1 | 9/2022 | Archer |
| 2022/0314078 A1 | 10/2022 | Watterson et al. |
| 2022/0323827 A1 | 10/2022 | Watterson et al. |
| 2022/0339493 A1 | 10/2022 | Larsen |
| 2022/0339520 A1 | 10/2022 | Toth |
| 2022/0342969 A1 | 10/2022 | Watterson et al. |
| 2022/0347516 A1 | 11/2022 | Taylor |
| 2022/0347548 A1 | 11/2022 | Watterson |
| 2022/0362613 A1 | 11/2022 | Watterson et al. |
| 2022/0362624 A1 | 11/2022 | Dalebout |
| 2022/0395729 A1 | 12/2022 | Toth |
| 2023/0039903 A1 | 2/2023 | Brammer et al. |
| 2023/0054845 A1 | 2/2023 | Smith |
| 2023/0122235 A1 | 4/2023 | Ashby et al. |
| 2023/0128721 A1 | 4/2023 | Plummer |
| 2023/0158358 A1 | 5/2023 | Ercanbrack et al. |
| 2023/0181993 A1 | 6/2023 | Taylor et al. |
| 2023/0191189 A1 | 6/2023 | Taylor et al. |
| 2023/0191197 A1 | 6/2023 | Ashby |
| 2023/0218975 A1 | 7/2023 | Toles et al. |
| 2023/0226401 A1 | 7/2023 | Watterson |

FOREIGN PATENT DOCUMENTS

| | | |
|---|---|---|
| CN | 102656507 A | 9/2012 |
| CN | 104268073 A | 1/2015 |
| CN | 108600785 A | 9/2018 |
| CN | 111741795 A | 10/2020 |
| EP | 1029507 A2 | 8/2000 |
| EP | 3833453 A1 | 6/2021 |
| KR | 10-2019-0000980 | 1/2019 |
| TW | I520764 | 2/2016 |
| TW | I1520764 | 2/2016 |
| TW | 202045227 | 12/2020 |
| TW | 202045228 | 12/2020 |
| TW | I727653 | 5/2021 |
| TW | I727654 | 5/2021 |
| WO | WO-02/15985 | 2/2002 |
| WO | 2010-109383 | 9/2010 |
| WO | WO-2017/155966 | 9/2017 |
| WO | 2020/167511 | 8/2020 |
| WO | 2020/167513 | 8/2020 |

OTHER PUBLICATIONS

AU Examination Report dated Jun. 1, 2022 in AU application No. 2020221016.
CN Office Action dated Apr. 2, 2022 in Chinese Patent Application No. 202080014080.X.
CN Office Action dated Mar. 22, 2022 in Chinese Patent Application No. 202080014136.1.
Foreign Action other than Search Report on CN 202080014080.X dated Apr. 2, 2022.
Foreign Action other than Search Report on CN 202080014136.1 dated Mar. 22, 2022.
U.S. Office Action on U.S. Appl. No. 16/742,762 dated Feb. 28, 2022.
Office Action for Canadian Application No. 3127653 dated Nov. 2, 2022, 5 pages.
Office Action for Chinese Application No. 202080014080.X dated Aug. 1, 2022, 17 pages.
Office Action for Chinese Application No. 202080014080.X dated Jan. 28, 2023, 14 pages.
Office Action for European Application No. 20755704.2 dated Nov. 9, 2022, 8 pages.
Office Action for Taiwanese Application No. 111110807 dated Sep. 22, 2022, 13 pages.
Office Action for Canadian Application No. 3127656 dated Nov. 2, 2022, 3 pages.
Office Action for Chinese Application No. 202080014136.1 dated Nov. 16, 2022, 14 pages.
Office Action for European Application No. 20755398.3 dated Oct. 17, 2022, 10 pages.
U.S. Appl. No. 13/088,007, filed Apr. 15, 2011, Watterson et al.
U.S. Appl. No. 15/973,176, filed May 7, 2018, Douglass.
U.S. Appl. No. 16/750,925, filed Jan. 25, 2019, Silcock.
U.S. Appl. No. 17/178,173, filed Feb. 17, 2021, Watterson et al.
U.S. Appl. No. 17/217,938, filed Mar. 30, 2021, Watterson et al.
U.S. Appl. No. 29/702,127, filed Sep. 16, 2019, Cutler et al.
U.S. Appl. No. 62/804,146, filed Feb. 11, 2019, Watterson.
U.S. Appl. No. 62/804,685, filed Feb. 12, 2019, Watterson et al.
U.S. Appl. No. 62/852,118, filed May 22, 2019, Hays et al.
U.S. Appl. No. 62/866,576, filed Jun. 25, 2019, Capell.
U.S. Appl. No. 62/887,391, filed Aug. 15, 2019, Ercanbrack et al.
U.S. Appl. No. 62/887,398, filed Aug. 15, 2019, Dalebout et al.
U.S. Appl. No. 62/897,113, filed Sep. 6, 2019, Ostler et al.
U.S. Appl. No. 62/914,007, filed Oct. 11, 2019, Willardson et al.
U.S. Appl. No. 62/934,291, filed Nov. 12, 2019, Dalebout et al.
U.S. Appl. No. 62/934,297, filed Nov. 12, 2019, Dalebout et al.
Bodyguard Fitness; Bodyguard T-30, T-45, T-75 Treadmills User Manual #691059 rev A Dec. 2015; User Manual; 76 pages.
Capell; Becca "iFit>Blog; Your Expert Guide to Proper Heart Rate Training;" Blog; located at: https://www.ifit.com/blog/yourexpert-guide-to-proper-heart-rate-training/; accessed on Jan. 14, 2020; 3 pages.
Cybex International, Inc.; "Cybex-R Series Treadmill Assembly Instructions—Part No. 1008084-0001 AC"; Assembly Manual; 2018; 31 pages.
Cybex International, Inc.; "Cybex-V Series Treadmill Assembly Instructions—Part No. 1008693-0001 AA;" Assembly Manual; 2018; 31 pages.
Cybex International, Inc.; Cybex 790T Treadmill Owner's Manual Cardiovascular Systems Part No. LT-24467-4 E; Owners Manual; 2015; 106 pages.
Gym Source; "The Three Top Treadmills for Heart Rate Control Training;" Webpage; located at: https://blog.gymsource.corn/the-3-top-treadmills-for-heart-rate-control-training; accessed on Jan. 14, 2020; 1 page.
International Search Report and Written Opinion dated Jun. 5, 2020 issued in Int'l Application No. PCT/US2020/016415, 9 pages.
International Search Report and Written Opinion dated May 26, 2020 issued in Int'l Application No. PCT/US2020/016405, 11 pages.
Taiwan Intellectual Property Office; Official Letter issued in Application No. 109104158 dated Sep. 9, 2020.
Taiwan Intellectual Property Office; Official Letter issued in Application No. 109104160 dated Sep. 9, 2020.
Taiwan Patent Application No. 110112089, filed Feb. 11, 2020, titled "Controlling an Exercise Machine Using a Video Workout Program;" 133 pages.
Truefitness.com; "True Alpine Runner Owner's Manual—Model# Til000, Revision 091418;" Owners Manual; 50 pages.
Truefitness.com; "True TC650 & TC900 Treadmill Owner's Manual—Revision 091418;" Owners Manual; 62 pages.
U.S. Appl. No. 17/066,485, filed Oct. 9, 2020, Weston et al.
U.S. Appl. No. 17/739,819, filed May 9, 2022, Buchanan.
U.S. Appl. No. 17/841,313, filed Jun. 15, 2022, Weston et al.
U.S. Appl. No. 17/963,822, filed Oct. 11, 2022, Powell.
U.S. Appl. No. 18/091,004, filed Dec. 29, 2022, Cox.
U.S. Appl. No. 18/103,221, filed Jan. 30, 2023, Dalebout et al.
U.S. Appl. No. 18/114,758, filed Feb. 27, 2023, Cutler et al.
U.S. Appl. No. 18/117,263, filed Mar. 3, 2023, Smith et al.
U.S. Appl. No. 18/123,026, filed Mar. 17, 2023, Silcock et al.
U.S. Appl. No. 18/132,277, filed Apr. 7, 2023, Vasquez et al.

(56) References Cited

OTHER PUBLICATIONS

U.S. Appl. No. 18/136,535, filed Apr. 19, 2023, Ashby et al.
U.S. Appl. No. 18/141,872, filed May 1, 2023, Ashby et al.
U.S. Appl. No. 18/205,299, filed Jun. 2, 2023, Wrobel.
U.S. Appl. No. 18/207,512, filed Jun. 8, 2023, Chuang.
U.S. Appl. No. 18/210,505, filed Jun. 15, 2023, Nielsen et al.
U.S. Appl. No. 62/273,852, filed Dec. 31, 2015, Watterson.
U.S. Appl. No. 63/073,081, filed Sep. 1, 2021, Ashby et al.
U.S. Appl. No. 63/079,697, filed Sep. 7, 2020, Willardson et al.
U.S. Appl. No. 63/086,793, filed Oct. 20, 2020, Ashby.
U.S. Appl. No. 63/134,036, filed Jan. 5, 2021, Ercanbrack et al.
U.S. Appl. No. 63/150,066, filed Feb. 16, 2021, Smith.
U.S. Appl. No. 63/156,801, filed Mar. 4, 2021, Watterson.
U.S. Appl. No. 63/165,498, filed Mar. 24, 2021, Archer.
U.S. Appl. No. 63/179,094, filed Apr. 23, 2021, Watterson et al.
U.S. Appl. No. 63/180,521, filed Apr. 27, 2021, Watterson et al.
U.S. Appl. No. 63/187,348, filed May 11, 2021, Dalebout et al.
U.S. Appl. No. 63/188,431, filed May 13, 2021, Plummer.
U.S. Appl. No. 63/200,903, filed Apr. 2, 2021, Watterson et al.
U.S. Appl. No. 63/211,870, filed Jun. 17, 2021, Watterson et al.
U.S. Appl. No. 63/216,313, filed Jun. 29, 2021, Watterson et al.
U.S. Appl. No. 63/229,794, filed Aug. 12, 2021, Brammer.
U.S. Appl. No. 63/235,002, filed Aug. 19, 2021, Smith.
U.S. Appl. No. 63/254,470, filed Oct. 11, 2021, Powell.
U.S. Appl. No. 63/278,714, filed Nov. 12, 2021, Taylor.
U.S. Appl. No. 63/289,997, filed Dec. 15, 2021, Taylor et al.
U.S. Appl. No. 63/290,455, filed Dec. 16, 2021, Taylor et al.
U.S. Appl. No. 63/290,557, filed Dec. 16, 2021, Ashby.
U.S. Appl. No. 63/298,170, filed Jan. 10, 2022, Ercanbrack et al.
U.S. Appl. No. 63/299,357, filed Jan. 13, 2022, Toles et al.
U.S. Appl. No. 63/305,976, filed Feb. 2, 2022, Watterson.
U.S. Appl. No. 63/329,270, filed Apr. 8, 2022, Vasquez et al.
U.S. Appl. No. 63/332,581, filed Apr. 25, 2022, Ashby et al.
U.S. Appl. No. 63/338,265, filed May 4, 2022, Ashby et al.
U.S. Appl. No. 63/350,072, filed Jun. 8, 2022, Chuang.
U.S. Appl. No. 63/352,539, filed Jun. 15, 2022, Nielsen et al.
U.S. Appl. No. 63/471,680, filed Jun. 7, 2023, Powell et al.
Watterson, et al., Chinese Search Report for Chinese Application No. 202080014136, dated Jul. 11, 2022.
U.S. Appl. No. 15/821,386, filed Nov. 22, 2017, Ashby.
U.S. Appl. No. 16/378,022, filed Apr. 8, 2019, Watterson.
U.S. Appl. No. 16/435,104, filed Jun. 7, 2019, Buchanan.
U.S. Appl. No. 16/506,085, filed Jul. 9, 2019, Smith.
U.S. Appl. No. 29/568,648, filed Jun. 20, 2016, Cutler et al.
U.S. Appl. No. 62/697,833, filed Jul. 13, 2018, Smith.
U.S. Appl. No. 62/796,952, filed Jan. 25, 2019, Silcock et al.
U.S. Appl. No. 62/842,118, filed May 5, 2019, Icon Health & Fitness, Inc.

* cited by examiner

First Data:

| Seconds Since Start | 605 |
|---|---|
| Speed (mph) | 6 |
| Incline % | 0.5 |
| HR Zone | 3 |
| Current HR | 150 |
| Workout State* | In Workout |

First CSV Encoding:

| Seconds Since Start | 605 |
|---|---|
| Speed (mph) | 6 |
| Incline % | 0.5 |
| Resistence | N/A |
| Target RPM | N/A |
| Target Watts | N/A |
| Target HR Zone | 3 |
| Target HR | 150 |
| Workout State* | In Workout |
| CSV Encoding | 605,6,0.5,0,0,0,3,150,1 |

\* Workout State (0=Warmup, 1=In Workout, 2=Cool Down)

Second Data:

| Seconds Since Start | 606 |
|---|---|
| Speed (mph) | 6 |
| Incline % | 0.5 |
| HR Zone | 3 |
| Current HR | 152 |
| Workout State* | In Workout |

Second CSV Encoding:

| Seconds Since Start | 606 |
|---|---|
| Speed (mph) | 6 |
| Incline % | 0.5 |
| Resistence | N/A |
| Target RPM | N/A |
| Target Watts | N/A |
| Target HR Zone | 3 |
| Target HR | 152 |
| Workout State* | In Workout |
| CSV Encoding | 605,6,0.5,0,0,0,3,152,1 |

\* Workout State (0=Warmup, 1=In Workout, 2=Cool Down)

Third Data:

| Seconds Since Start | 607 |
|---|---|
| Speed (mph) | 5 |
| Incline % | 4.5 |
| HR Zone | 3 |
| Current HR | 156 |
| Workout State* | In Workout |

Third CSV Encoding:

| Seconds Since Start | 607 |
|---|---|
| Speed (mph) | 5 |
| Incline % | 4.5 |
| Resistance | N/A |
| Target RPM | N/A |
| Target Watts | N/A |
| Target HR Zone | 3 |
| Target HR | 156 |
| Workout State* | In Workout |
| CSV Encoding | 607,5,4.5,0,0,0,3,156,1 |

* Workout State (0=Warmup, 1=In Workout, 2=Cool Down)

Fourth Data:

| Seconds Since Start | 608 |
|---|---|
| Speed (mph) | 5 |
| Incline % | 4.5 |
| HR Zone | 3 |
| Current HR | 160 |
| Workout State* | In Workout |

Fourth CSV Encoding:

| Seconds Since Start | 608 |
|---|---|
| Speed (mph) | 5 |
| Incline % | 4.5 |
| Resistence | N/A |
| Target RPM | N/A |
| Target Watts | N/A |
| Target HR Zone | 3 |
| Target HR | 160 |
| Workout State* | In Workout |
| CSV Encoding | 608,5,4.5,0,0,0,3,160,1 |

* Workout State (0=Warmup, 1=In Workout, 2=Cool Down)

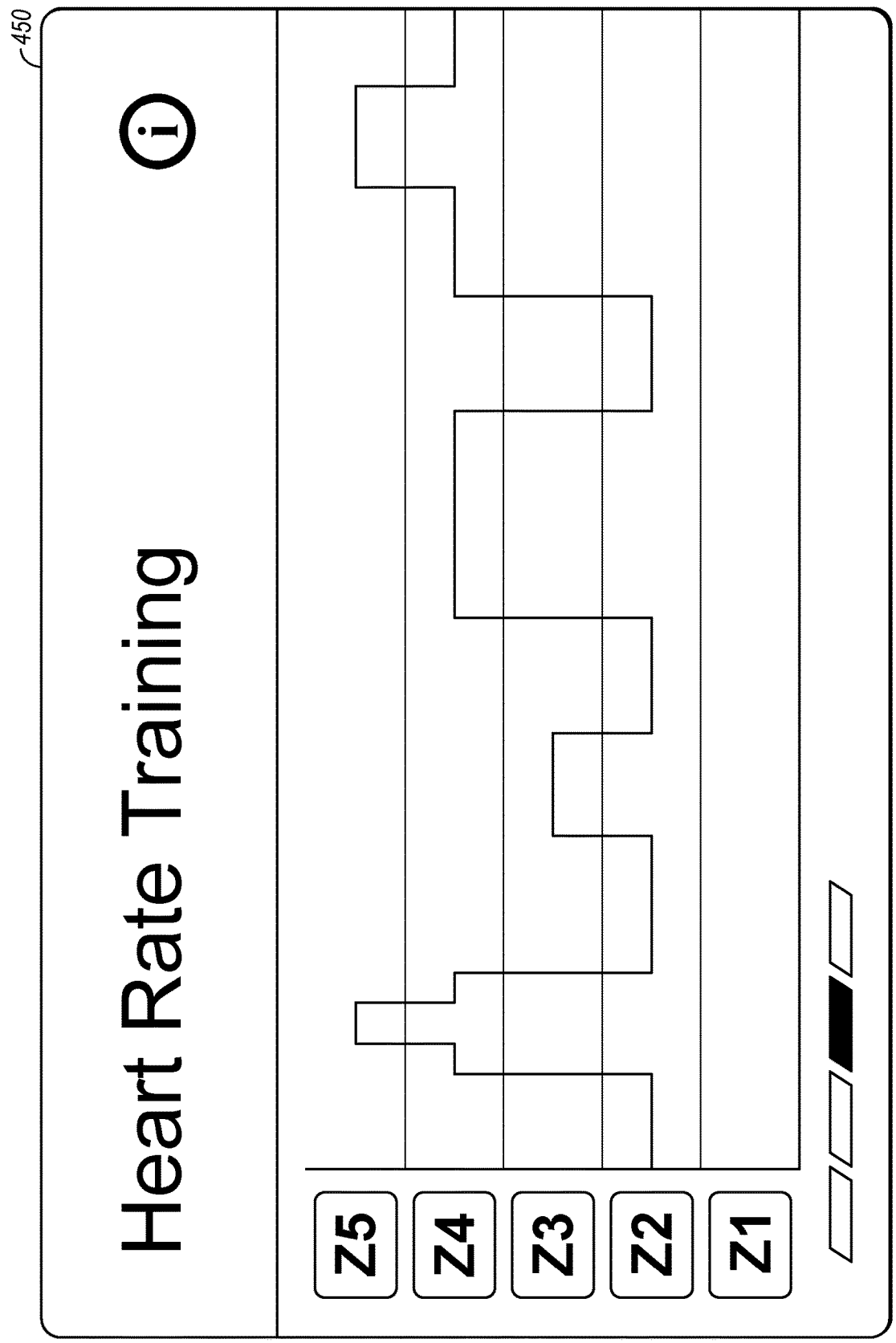

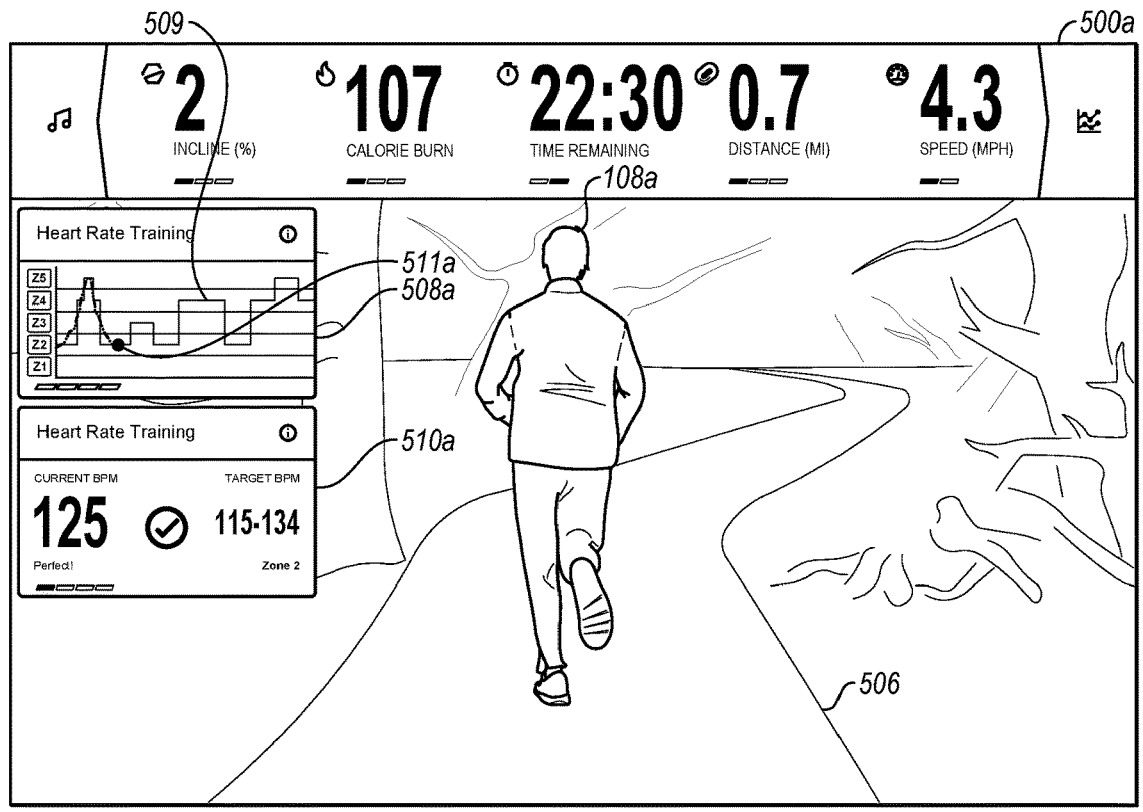

| Current Programmed Heart Rate Zone | Zone 2 |
|---|---|
| Current Programmed Heart Rate Zone Range | 115-134 BPM |
| Previous Programmed Heart Rate Zone | Zone 4 |
| Time Since Workout Began | 450 Seconds |
| Time Since Zone Change | 70 Seconds |
| Time Remaining in Current Programmed Heart Rate Zone | 50 Seconds |
| Time Remaining in Workout | 1350 Seconds |
| Heart Rate Monitoring Rate | Once Per Second |
| Threshold Heart Rate Trend Rate | -5 Seconds |
| Warmup-Time Threshold | 180 Seconds |
| User's Last Ten Actual Heart Rates (BPM) | 122,122,123,123,124,124,125,124,125,125 |
| Baseline Difficulty Level | $B_0$ |
| Baseline Speed | 4 MPH |
| Current Difficulty Level | $B_2$ |
| Current Speed | 4.3 MPH |
| User's Actual Heart Rate | 125 BPM |
| User's Actual Heart Rate Zone | Zone 2 |
| User's Actual Heart Rate Zone Range | 115-134 BPM |

FIG. 5A

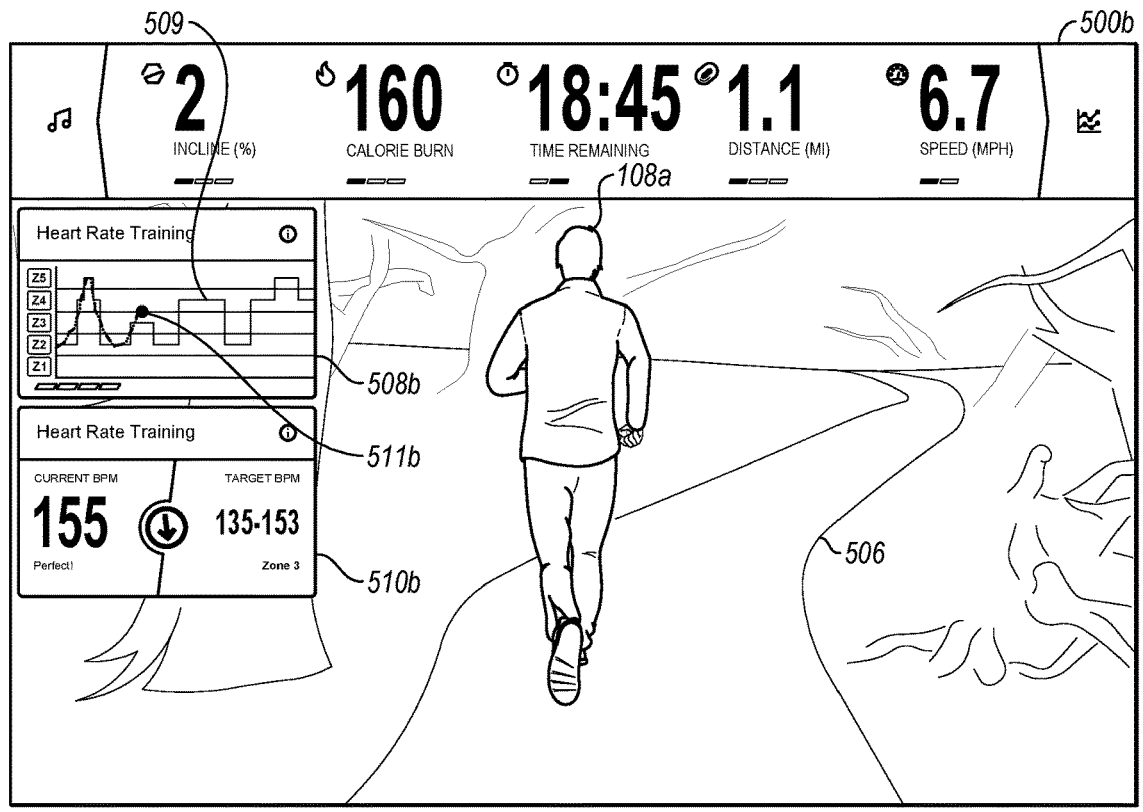

| | |
|---|---|
| Current Programmed Heart Rate Zone | Zone 3 |
| Current Programmed Heart Rate Zone Range | 135-153 BPM |
| Previous Programmed Heart Rate Zone | Zone 2 |
| Time Since Workout Began | 675 Seconds |
| Time Since Zone Change | 60 Seconds |
| Time Remaining in Current Programmed Heart Rate Zone | 60 Seconds |
| Time Remaining in Workout | 1125 Seconds |
| Heart Rate Monitoring Rate | Once Per Second |
| Threshold Heart Rate Trend Rate | +4 Seconds |
| Warmup-Time Threshold | 180 Seconds |
| User's Last Ten Actual Heart Rates (BPM) | 152,152,153,153,154,154,155,155,155,155 |
| Baseline Difficulty Level | $B_0$ |
| Baseline Speed | 6 MPH |
| Current Difficulty Level | $B_2$ |
| Current Speed | 6.7 MPH |
| User's Actual Heart Rate | 155 BPM |
| User's Actual Heart Rate Zone | Zone 4 |
| User's Actual Heart Rate Zone Range | 154-172 BPM |

*FIG. 5B*

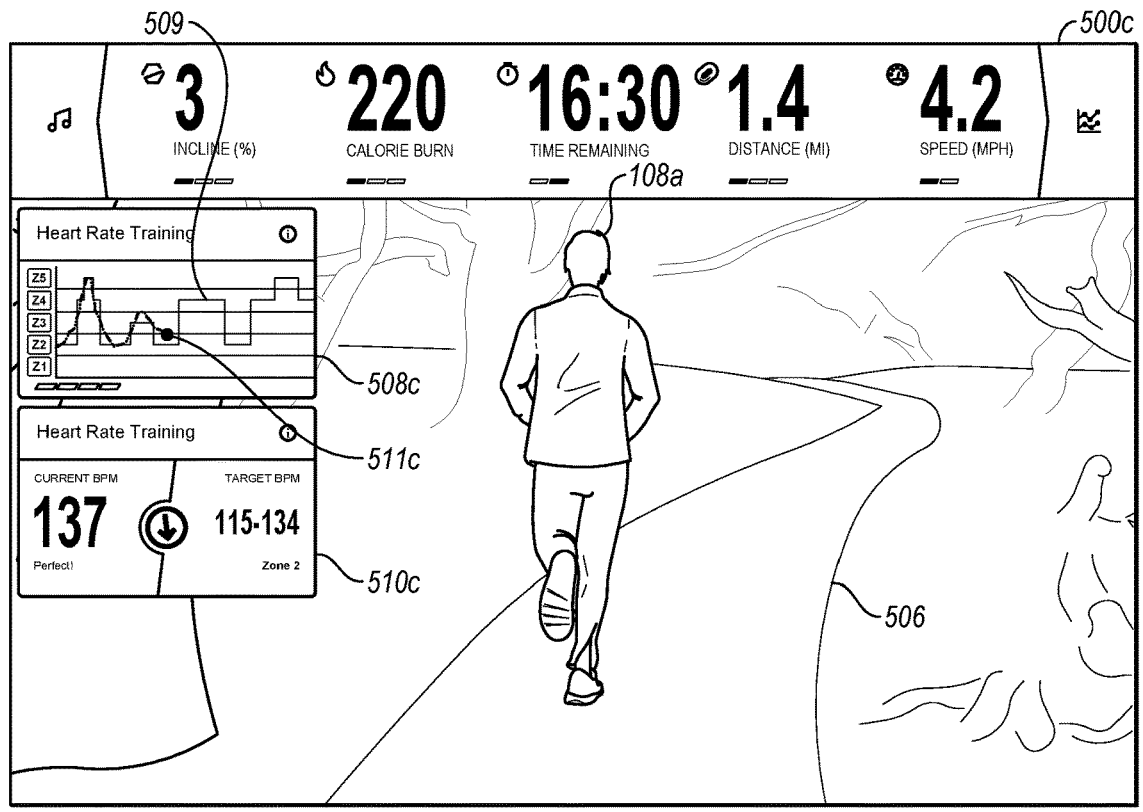

| Current Programmed Heart Rate Zone | Zone 2 |
|---|---|
| Current Programmed Heart Rate Zone Range | 115-134 BPM |
| Previous Programmed Heart Rate Zone | Zone 3 |
| Time Since Workout Began | 810 Seconds |
| Time Since Zone Change | 50 Seconds |
| Time Remaining in Current Programmed Heart Rate Zone | 70 Seconds |
| Time Remaining in Workout | 990 Seconds |
| Heart Rate Monitoring Rate | Once Per Second |
| Threshold Heart Rate Trend Rate | -4 Seconds |
| Warmup-Time Threshold | 180 Seconds |
| User's Last Ten Actual Heart Rates (BPM) | 131,131,132,133,133,134,135,136,136,137 |
| Baseline Difficulty Level | $B_0$ |
| Baseline Speed | 4 MPH |
| Current Difficulty Level | $B_1$ |
| Current Speed | 4.2 MPH |
| User's Actual Heart Rate | 137 BPM |
| User's Actual Heart Rate Zone | Zone 3 |
| User's Actual Heart Rate Zone Range | 135-153 BPM |

FIG. 5C

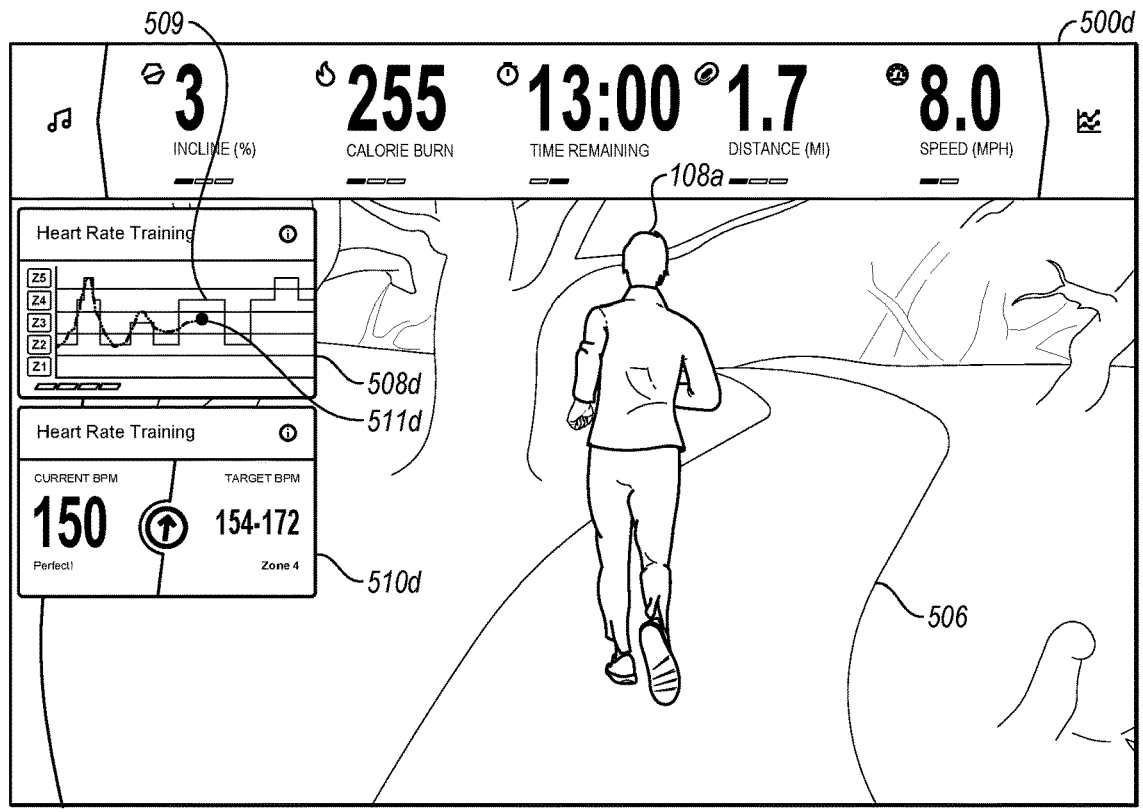

| | |
|---|---|
| Current Programmed Heart Rate Zone | Zone 4 |
| Current Programmed Heart Rate Zone Range | 154-172 BPM |
| Previous Programmed Heart Rate Zone | Zone 2 |
| Time Since Workout Began | 1020 Seconds |
| Time Since Zone Change | 120 Seconds |
| Time Remaining in Current Programmed Heart Rate Zone | 120 Seconds |
| Time Remaining in Workout | 780 Seconds |
| Heart Rate Monitoring Rate | Once Per Second |
| Threshold Heart Rate Trend Rate | +5 Seconds |
| Warmup-Time Threshold | 180 Seconds |
| User's Last Ten Actual Heart Rates (BPM) | 148,147,148,149,149,149,150,150,150,150 |
| Baseline Difficulty Level | $B_0$ |
| Baseline Speed | 8 MPH |
| Current Difficulty Level | $B_0$ |
| Current Speed | 8 MPH |
| User's Actual Heart Rate | 150 BPM |
| User's Actual Heart Rate Zone | Zone 3 |
| User's Actual Heart Rate Zone Range | 135-153 BPM |

*FIG. 5D*

ENCODING EXERCISE MACHINE CONTROL COMMANDS IN SUBTITLE STREAMS

CROSS-REFERENCE TO RELATED APPLICATIONS

This application is a continuation of U.S. patent application Ser. No. 16/742,762, filed Jan. 14, 2020, which claims the benefit of and priority to U.S. Provisional Patent Application No. 62/804,685, filed Feb. 12, 2019, and also claims the benefit of, and priority to, U.S. Provisional Patent Application No. 62/866,576, filed Jun. 25, 2019. Each of these applications is incorporated herein by reference in its entirety for all that it discloses.

BACKGROUND

Stationary exercise machines have become an increasingly popular way to exercise. To combat the boredom and burnout that is often experienced by users that exercise with these exercise machines, exercise machines are often sold with a number of different pre-programmed workout programs that are saved within the electronics of the exercise machines. For example, these workout programs may include a "fat burn" workout program, a "hills" workout program, a "performance" workout program, and/or other workout programs.

To enable a user to become more immersed in a workout performed on an exercise machine, some exercise machines are capable of executing video workout programs. A video workout program generally includes a video as well as corresponding control commands. The video generally depicts a trainer performing a workout. The corresponding control commands, when executed during the display of the video, generally control an exercise machine to mimic the workout that is depicted in the video as being performed by the trainer. For example, where a trainer is running at 6 miles per hour in a video of a video workout program, the corresponding control commands of the video workout program may control a running belt of a treadmill to likewise operate at 6 miles per hour.

One problem faced by users attempting to perform a video workout program on an exercise machine is that it can be difficult to maintain synchronization between the video and the corresponding control commands in the video workout program. For example, where the video in a video workout program experiences a delay, the corresponding control commands of the video workout program can become unsynchronized from the video, resulting in an incongruity between what a user sees in the video and what the user experiences on the exercise machine. For example, where the video in a video workout program on a treadmill shows a trainer transitioning from running at 5 miles per hour to 6 miles per hour, if the video buffers or experiences some other delay around the time that the transition is depicted in the video, the corresponding control commands in the video workout program can get ahead of the video, resulting in the running belt of the treadmill speeding up from operating at 5 miles per hour to operating at 6 miles per hour prior to the transition being depicted in the video. This lack of synchronization between a video and corresponding control commands in a video workout program can be unsettling or even dangerous for a user of an exercise machine and can limit the ability of the user to become sufficiently immersed in a workout performed on the exercise machine to effectively combat boredom and burnout.

Another problem faced by users attempting to perform a video workout program on an exercise machine is that the fitness level of the user may be higher or lower than is optimal for the workout being performed in the video. In these situations, the video workout program may allow a user to manually override the control commands in order to allow the user to adjust the video workout program to better match the user's fitness level. Unfortunately, however, requiring adjustments of a video workout program to be made manually by the user can detract from the enjoyment of the user and can result in the user inadvertently operating the exercise machine at a level that is not optimal for the user's fitness level. Further, manual adjustment of a video workout program on an exercise machine can result in a lack of integrity between what a user sees in the video and what the user experiences on the exercise machine. This lack of integrity between the video and the manually-overridden control commands in the video workout program can be unsettling for a user of an exercise machine, and can limit the ability of the user to become sufficiently immersed in a workout performed on the exercise machine to effectively combat boredom and burnout.

The subject matter claimed herein is not limited to embodiments that solve any disadvantages or that operate only in environments such as those described above. Rather, this background is only provided to illustrate one example technology area where some embodiments described herein may be practiced.

SUMMARY

In one aspect of the disclosure, a stationary exercise machine may include one or more moveable members configured to be moved by a user, an actuator configured to selectively adjust the speed of, or the amount of resistance on, the one or more moveable members, and one or more processors. The one or more processors may be configured to receive a video workout program, execute the video workout program set to a first difficulty level, receive a second difficulty level, and execute the video workout program reset to the second difficulty level.

It is to be understood that both the foregoing summary and the following detailed description are explanatory and are not restrictive of the invention as claimed.

BRIEF DESCRIPTION OF THE DRAWINGS

Embodiments will be described and explained with additional specificity and detail through the use of the accompanying drawings in which:

FIG. 4B illustrates a chart of programmed heart rate zones for a video workout program;

FIGS. 5A-5D illustrate video frames and charts that may be employed in dynamically scaling a video workout program on an exercise machine based on heart rate monitoring;

Throughout the drawings, identical reference numbers designate similar, but not necessarily identical, elements.

DETAILED DESCRIPTION

Figure 1:
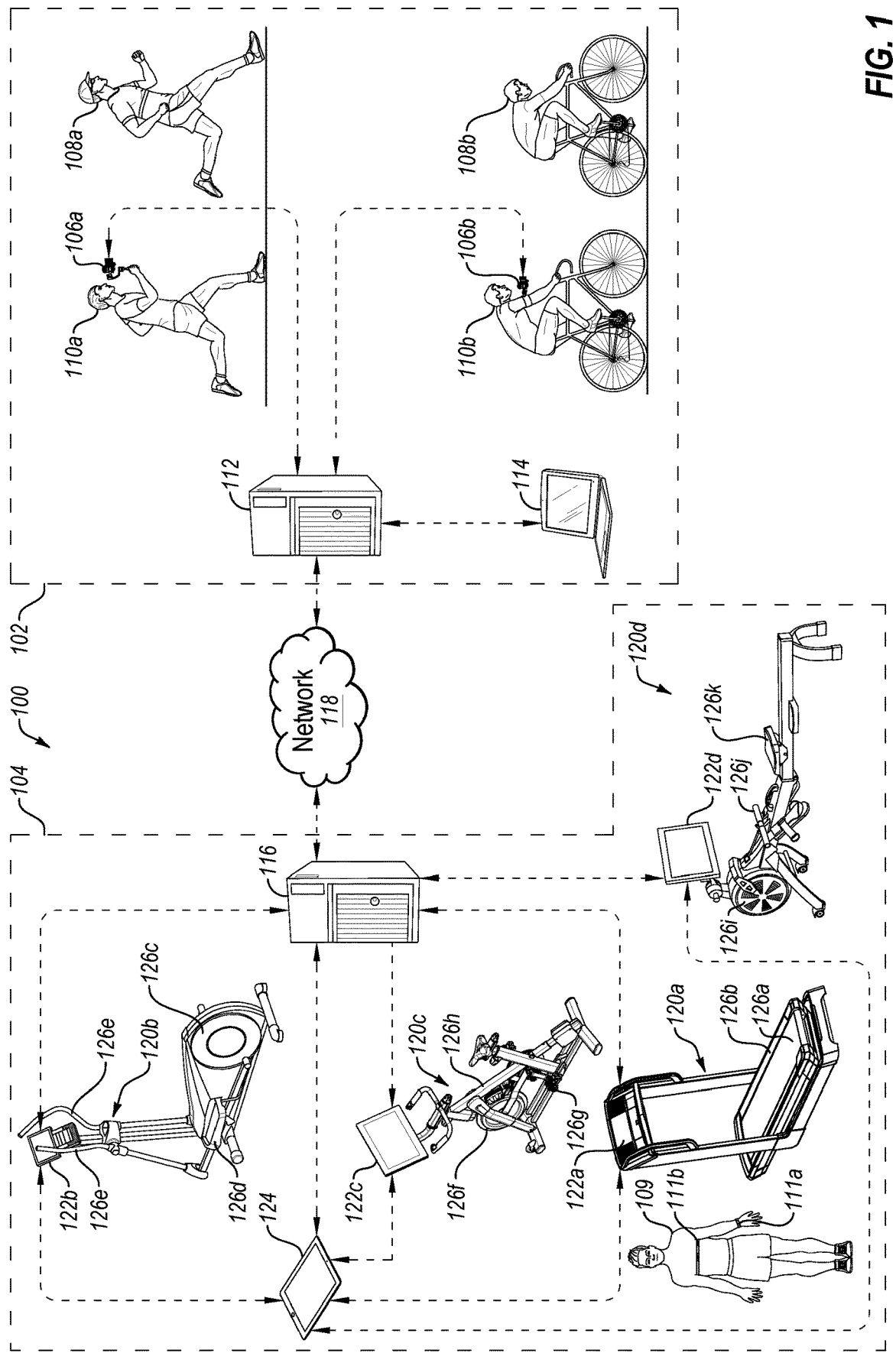
FIG. 1 illustrates a flowchart of an example exercise system for controlling an exercise machine using a video workout program.

While conventional stationary exercise machines generally include multiple conventional workout programs that are saved within the electronics of the exercise machines, these conventional workout programs are generally not effective at enabling a user to become immersed in workouts performed on the exercise machines. Therefore, some exercise machines are capable of being updated with video workout programs that include a video of a trainer performing a workout, in addition to corresponding control commands that control the exercise machine to mimic the workout performed by the trainer in the video. For example, where a trainer is running at 6 miles per hour in the video (either along a real-world path, or on a treadmill), the corresponding control commands may control a running belt of a treadmill to likewise operate at 6 miles per hour.

Unfortunately, however, it can be difficult to maintain synchronization between the video and the corresponding control commands in a video workout program. For example, where the video of a video workout program experiences a delay due to network limitations, memory limitations, or processing limitations, the corresponding control commands can become unsynchronized from the video, resulting in an incongruity between what a user sees in the video and what the user experiences on the exercise machine. For example, where the video in a video workout program on a treadmill shows a trainer transitioning from running at 10 miles per hour to 4 miles per hour, if the video buffers for a few seconds (due to network limitations, memory limitations, or processing limitations) around the time of the transition in the video, the corresponding control commands can get ahead of the video, resulting in the running belt of the treadmill slowing down from operating at 10 miles per hour to operating at 4 miles per hour prematurely. In this example, this lack of synchronization between the video and the corresponding control commands can be unsettling or even dangerous for a user of the treadmill because the running belt can slow down prior to the user expecting the running belt to slow down, which can limit the ability of the user to become sufficiently immersed in a workout performed on the treadmill to effectively combat boredom and burnout.

Further, the difficulty of maintaining synchronization between the video and the corresponding control commands in a video workout program can be exacerbated where the video is live and depicts a live event. For example, where a video in a video workout program depicts a live marathon, a user may be able to perform a workout on their treadmill in their home that mimics the live marathon, at the same time that the live marathon is occurring at a remote location, which may allow the user to become immersed in the workout performed on the treadmill because the user may feel like they are participating in the live marathon. However, network limitations, memory limitations, or processing limitations may prevent the video of the video workout program from keeping up, or cause the video to jump ahead, with respect to the actual live marathon, which may result in the control commands getting ahead of, or getting behind from, the video. This lack of synchronization between the video and the corresponding control commands can be unsettling or even dangerous for the user of the treadmill because the running belt can speed up or slow down before or after the user expects the running belt to speed up or slow down, which can limit the ability of the user to become sufficiently immersed in the workout performed on the treadmill by preventing the user from feeling like they are participating in the live marathon.

Also, in some situations, the fitness level of a user may be higher or lower than is optimal for a workout being performed in a video of a video workout program. In these situations, the video workout program may allow a user to manually override the control commands in order to allow the user to adjust the video workout program to better match the user's fitness level. Continuing with a previous example, where a trainer is running at 6 miles per hour in the video, but the user's fitness level is high enough that running at 6 miles per hour is too easy for the user, the user may manually override the control commands to control the running belt of the treadmill to operate at 10 miles per hour. Alternatively, where the user's fitness level is low enough that running at 6 miles per hour is too difficult for the user, the user may manually override the control commands to control the running belt of the treadmill to operate at 2 miles per hour. Unfortunately, however, requiring adjustments of a video workout program to be made manually by the user can detract from the enjoyment of the user and can result in the user inadvertently operating the exercise machine at a level that is not optimal for the user's fitness level.

Further, manual adjustment of a video workout program on an exercise machine can result in a lack of integrity between what a user sees in the video and what the user experiences on the exercise machine. Continuing with the previous example, where the video on the treadmill shows a trainer running at 6 miles per hour, but the user has manually overridden the control commands to control the running belt of the treadmill to operate at 2 miles per hour, the video may depict the trainer running while the user is only walking at a pace that is dramatically slower than the trainer. Alternatively, where the video on the treadmill shows a trainer running at 6 miles per hour, but the user has manually overridden the control commands to control the running belt of the treadmill to operate at 10 miles per hour, the video may depict the trainer running while the user is sprinting at a pace that is dramatically faster than the trainer. This lack of integrity between a video and manually overridden control commands in a video workout program can be unsettling for a user of an exercise machine and can limit the ability of the user to become sufficiently immersed in a workout performed on the exercise machine to effectively combat boredom and burnout.

Some embodiments disclosed herein may include methods for controlling an exercise machine using a video workout program. For example, a method may include capturing, remotely from an exercise machine, video, of a video workout program, depicting performance of a workout. Then, the method may include encoding, remotely from the exercise machine, exercise machine control commands, of the video workout program, into a subtitle stream (also known as a closed caption stream) of the video. Where the video workout program depicts a live workout, the encoding may occur synchronously with the capturing of the video.

Alternatively, where the video workout program depicts a pre-recorded workout, the encoding may occur subsequent to the capturing of the video. Then, the video workout program may be sent to the exercise machine and the method may include various actions performed locally to the exercise machine, such as decoding the subtitle stream of the video to access the exercise machine control commands, and displaying the video simultaneously with controlling one or more moveable members of the exercise machine using the exercise machine control commands.

Due to the fact that, in a video, frames from the video are timed with (e.g., linked or tied to) frames of the subtitle stream, the encoding of control commands in a subtitle stream of a video may maintain synchronization of the video and of corresponding control commands. This synchronization between a video and corresponding control commands can enable a user to become sufficiently immersed in a workout performed on the exercise machine to avoid the boredom and burnout that is often experienced by users of exercise machines.

Also, in another example of methods for controlling an exercise machine using a video workout program, a method may include executing a video workout program at an exercise machine, continuously monitoring an actual heart rate of a user, and periodically determining at least that an actual heart rate zone of the user is not equal to a current programmed heart rate zone of the video workout program. The method may also include periodically determining that the actual heart rate of the user is not trending toward the current programmed heart rate zone by at least a threshold heart rate trend rate. In response, the method may further include adaptively scaling the video workout program by adjusting the current difficulty level upward if the actual heart rate zone is lower than the current programmed heart rate zone, or downward if the actual heart rate zone is higher than the current programmed heart rate zone.

By monitoring not only the user's current heart rate but also the direction and speed at which the user's heart rate is trending (e.g., the slope of the user's heart rate), some embodiments may avoid changing the current difficulty level too often. Further, in some embodiments, the changes to the current difficulty level can be limited to avoid being changed too dramatically in order to avoid the current difficulty level experienced by the user from being dramatically different from the difficulty level that the user sees in the video. As a result of the current difficulty level not being changed too often and/or too dramatically, the enjoyment of the user may be increased, the inadvertent operation of the exercise machine at a level that is not optimal for the user's fitness level may be avoided, and/or the integrity between the workout of the trainer shown in the video and the actual workout performed by the user can be maintained, thus enabling a user to become sufficiently immersed in the workout performed on the exercise machine to avoid the boredom and burnout that is often experienced by users of exercise machines.

Turning now to the drawings, FIG. 1 illustrates a flowchart of an example exercise system 100 for controlling an exercise machine using a video workout program. The exercise system 100 may include a remote location 102 and a local location 104 connected by a network 118.

In some embodiments, the network 118 may be configured to communicatively couple the any two devices in the exercise system 100 to one another, and/or to other devices. In some embodiments, the network 118 may be any wired or wireless network, or combination of multiple networks, configured to send and receive communications between systems and devices. In some embodiments, the network 118 may include a Personal Area Network (PAN), a Local Area Network (LAN), a Metropolitan Area Network (MAN), a Wide Area Network (WAN), a Storage Area Network (SAN), the Internet, or some combination thereof. In some embodiments, the network 118 may also be coupled to, or may include, portions of a telecommunications network, including telephone lines, for sending data in a variety of different communication protocols, such as a cellular network or a Voice over IP (VoIP) network.

In the remote location 102, the exercise system 100 may include a video camera 106a or 106b that may be employed to capture video of a trainer 108a or 108b performing a workout, and which includes stabilization capabilities to avoid the captured video from being unduly shaky. For example, the video camera 106a may be employed by a videographer 110a to capture video of the trainer 108a performing a workout in which the trainer 108a runs a live marathon. Similarly, the video camera 106b may be employed by a videographer 110b to capture video of the trainer 108b performing a workout in which the trainer 108b rides a bicycle in a live road bicycle race. In either example, the result may be captured video that can be sent to a remote server 112 for further processing. The video may be formatted in any one of multiple video formats, at least some of which being capable of supporting a subtitle stream. Some example formats may include, but are not limited to, MPEG-4, Dynamic Adaptive Streaming over HTTP (MPEG-DASH), and HTTP Live Streaming (HLS).

Next, a producer (not shown) may utilize a computer 114 to input exercise machine control commands for the video into a video workout program, which may be encoded into a subtitle stream of the video, or may be encoded separately from the video. For example, where the video is being produced to be utilized as a live video workout program, the producer may input the exercise machine control commands using the computer 114 synchronously with the videographer 110a or 110b using the video camera 106a or 106b to capture video of the trainer 108a or 108b performing the workout (e.g., during a live event). In this example, the producer may also give corresponding instructions to the trainer, such as through an earpiece worn by the trainer, in order to help the trainer and the producer be in sync following a common script or plan for the workout. Alternatively, where the video is produced to be utilized in a pre-recorded video workout program, the producer may input exercise machine control commands using the computer 114 subsequent to the videographer 110a or 110b using the video camera 106a or 106b to capture video of the trainer 108a or 108b (e.g., minutes, hours, or days after the live event).

In some embodiments, the control commands may be encoded into a subtitle stream of the video, which may be a subtitle stream that is not commonly used. For example, where a first subtitle stream (e.g., subtitle stream 1) is commonly used for English subtitles, and a second subtitle stream (e.g., subtitle stream 2) is commonly used for Spanish subtitles, but a third subtitle stream (e.g., subtitle stream 3) is commonly not used, the third subtitle stream (e.g., subtitle stream 3) may be used for encoding exercise machine control commands. The video workout program, including the captured video and the control commands (which may be encoded in the subtitle stream of the video, or may be encoded separately from the video) may then be transmitted over the network 118 from the remote server 112 in the remote location 102 to a local server 116 in the local location 104.

The video workout program may then be transmitted from the local server 116 to be used in connection with an exercise machine 120a, 120b, 120c, or 120d. For example, the video workout program may be transmitted from the local server 116 to a console 122a, 122b, 122c, or 122d of the exercise machine 120a, 120b, 120c, or 120d, which may include a display, such as a touchscreen display. Alternatively, a separate tablet 124 may function as a console, or may function in connection with a console, of the exercise machine 120a, 120b, 120c, or 120d, and may also include a display, such as a touchscreen display. The tablet 124 may communicate with the console 122a, 122b, 122c, or 122d, and/or with the exercise machine 120a, 120b, 120c, or 120d, via a network connection, such as a Bluetooth connection. In either example, the video and the control commands (which may be encoded in the subtitle stream of the video) may be decoded and/or accessed. Then, the console 122a, 122b, 122c, or 122d and/or the tablet 124 may display the video from the video workout program (e.g., of the trainer 108a or 108b performing the marathon or the road bicycle race at the remote location 102) while simultaneously controlling one or more moveable members of the exercise machine 120a, 120b, 120c, or 120d using the control commands.

In embodiments where the control commands are encoded in the subtitle stream of the video, due to the fact that, in a video, frames from the video are timed with frames of a subtitle stream, the encoding of control commands in a subtitle stream maintains synchronization of the video and of corresponding control commands. This synchronization in a video workout program between the video and the corresponding control commands can enable a user to become immersed in a workout on the exercise machine 120a, 120b, 120c, or 120d, which may help the user to avoid the boredom and burnout that is often experienced by users of exercise machines.

Further, during performance of a workout by a user 109 using the video workout program on the exercise machine 120a, 120b, 120c, or 120d, a heart rate of the user 109 may be monitored by the console 122a, 122b, 122c, or 122d, and/or the tablet 124. This heart rate monitoring may be accomplished by receiving continuous heart rate measurements wirelessly (such as over Bluetooth or Ant+) from a heart rate monitoring device worn by the user 109, such as a heart rate strap 111b or a heart rate watch 111a, or other wearable heart rate monitor. Alternatively, the heart rate monitoring device may be built into another device, such as being built into handlebars or handgrips of the exercise machine 120a, 120b, 120c, or 120d.

The exercise machine 120a is illustrated in FIG. 1 as a treadmill. The treadmill 120a may include multiple different moveable members, including a running belt 126a and a running deck 126b, which may include one or more operating parameters that are selectively adjustable within a limited range. During performance of a workout using a video workout program on the treadmill 120a, the running belt 126a may rotate and the running deck 126b may incline. One example of an operating parameter on the treadmill 120a is a speed of the running belt 126a. The running belt 126a may rotate at different speeds within a limited range. An actuator (see FIG. 2), for example a belt motor, may selectively adjust the speed at which the running belt 126a rotates within the limited range. Another example of an operating parameter on the treadmill 120a is the inclination of running deck 126b. The running deck 126b may be selectively inclinable to different angles within a limited range. An actuator, for example an incline motor, may selectively adjust the incline of the running deck 126b within the limited range.

The exercise machine 120b is illustrated in FIG. 1 as an elliptical machine. The elliptical machine 120b may include multiple different moveable members, including a flywheel 126c, foot rails or pedals 126d, and handles 126e, which include one or more operating parameters that are selectively adjustable within a limited range. During performance of a workout using a video workout program on the elliptical machine 120b, movement of the foot rails or pedals 126d and the handles 126e may cause the flywheel 126c to rotate. One example of an operating parameter on the elliptical machine 120b is the amount of resistance applied to the flywheel 126c. A differing amount of resistance can be applied to the flywheel 126c to make the movement of the foot rails or pedals 126d and the handles 126e more difficult or less difficult. An actuator, such as a brake, may be used to selectively adjust the amount of resistance that is applied to the flywheel 126c. Another example of an operating parameter on the elliptical machine 120b is the inclination of foot rails or pedals 126d. The foot rails or pedals 126d may be inclinable to different angles within a limited range. An actuator, such as an incline motor, may selectively adjust the incline of the foot rails or pedals 126d within the limited range. Yet another example of an operating parameter on exercise machine 120b is the stride length of the foot rails or pedals 126d and/or the handles 126e. The stride length of the foot rails or pedals 126d and/or the handles 126e may be adjustable to different distances within a limited range. An actuator, for example a stride length motor, may selectively adjust the stride length of the foot rails or pedals 126d and/or the handles 126e within the limited range.

The exercise machine 120c is illustrated in FIG. 1 as an exercise bike. The exercise bike 120c may include multiple different moveable members, including a flywheel 126f, pedals 126g, and a frame 126h, which include one or more operating parameters that are selectively adjustable within a limited range. During performance of a workout using a video workout program on the exercise bike 120c, movement of the pedals 126g may cause the flywheel 126f to rotate. One example of an operating parameter on the exercise bike 120c is the amount of resistance applied to the flywheel 126f. A differing amount of resistance can be applied to the flywheel 126f to make rotation of the pedals 126g more difficult or less difficult. An actuator, such as a brake, may be used to selectively adjust the amount of resistance that is applied to the flywheel 126f within the limited range. Another example of an operating parameter on the exercise bike 120c is the position of the frame 126h. The frame 126h may tilt forward, backward, or from side to side within a limited range. An actuator, such as a tilt motor, may selectively adjust the position of the frame 126h within the limited range.

The exercise machine 120d is illustrated in FIG. 1 as a rower machine. The rower machine 120d may include multiple different moveable members, including a flywheel 126i, a rowbar 126j, and a seat 126k, which include one or more operating parameters that are selectively adjustable within a limited range. During performance of a workout using a video workout program on the rower machine 120d, movement of the rowbar 126j may cause the flywheel 126i to rotate. One example of an operating parameter on the rower machine 120d is the amount of resistance applied to the flywheel 126i. A differing amount of resistance can be applied to the flywheel 126i to make pulling on the rowbar 126j more difficult or less difficult. An actuator, such as a brake, may be used to selectively adjust the amount of resistance that is applied to the flywheel 126*i* within the limited range.

Figure 2:
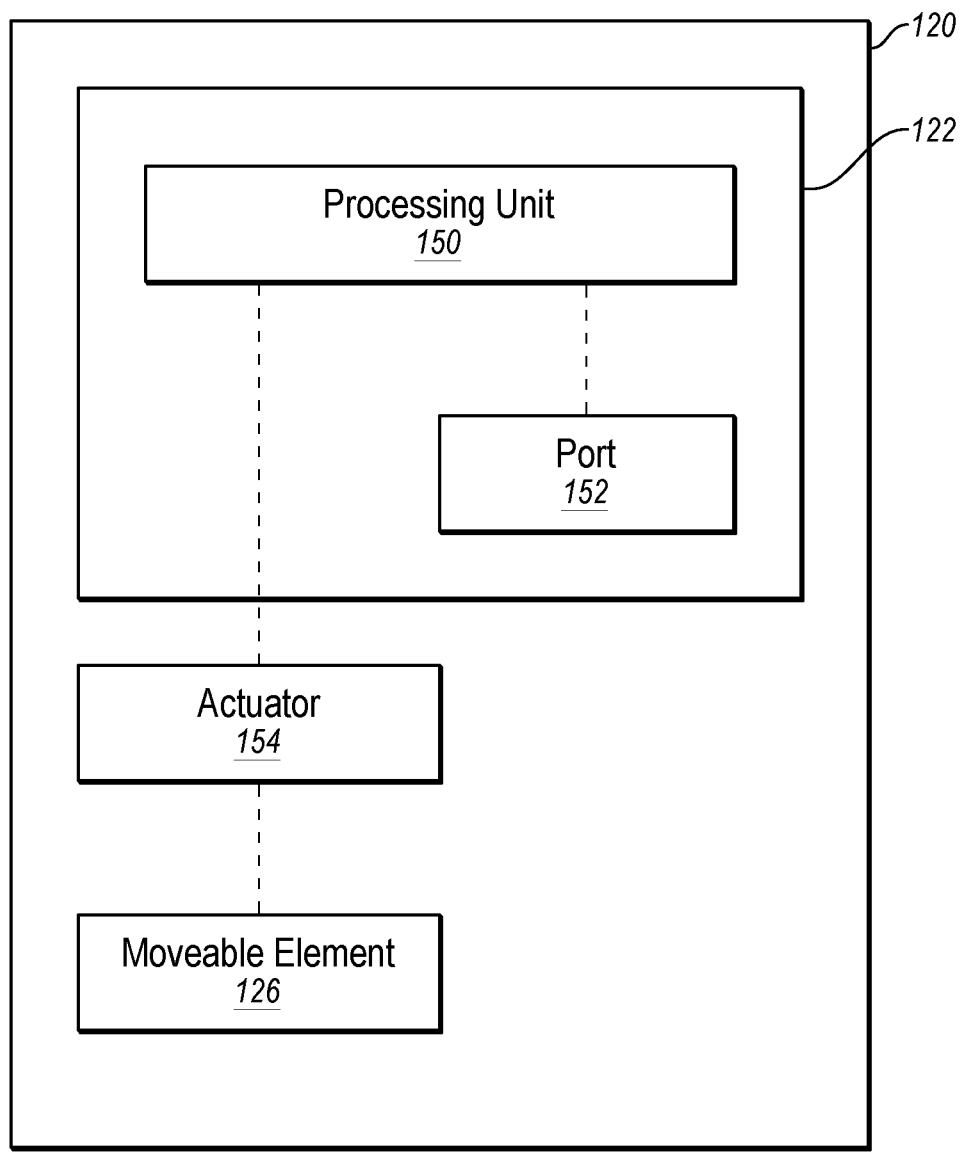
FIG. 2 illustrates a block diagram of an example exercise machine that may be controlled using a video workout program.

FIG. 2 illustrates a block diagram of an example exercise machine 120 that may be controlled using a video workout program. The exercise machine 120 of FIG. 2 may represent, and may include similar components to, any of the exercise machine 120*a*, 120*b*, 120*c*, or 120*d* of FIG. 1, for example.

As disclosed in FIG. 2, the exercise machine 120 may include a processing unit 150, a receiving port 152, an actuator 154, and a moveable member 126. The moveable member 126, which may be similar to any of the moveable members 126*a*-126*k* of FIG. 1, for example. The processing unit 150 may be communicatively connected to the receiving port 152 and may be included within a console 122, which may be similar to any of the consoles 122*a*, 122*b*, 122*c*, or 122*d* of FIG. 1, for example. The processing unit 150 may also be communicatively connected to the actuator 154. In response to control commands executed by the processing unit 150, the actuator 154 may selectively adjust one or more operating parameters of the moveable member 126 within a limited range.

Data, including data in a video workout program, can be received by the exercise machine 120 through the receiving port 152. As stated previously, a video workout program may include video as well as control commands. Control commands may provide control instructions to an exercise machine (such as a treadmill, an elliptical machine, an exercise bike, or a rower machine). Control commands may include, for example, control commands for a belt motor, an incline motor, and other actuators. In addition to actuator control commands, control commands may further include distance control commands, time control commands, and/or heart rate zone control commands. These control commands may provide a series of actuator control commands for execution at specific times or at specific distances. For example, a control command for an actuator to be at a certain level for a specific amount of time or for a specific distance. These control commands may also provide a series of actuator control commands for execution at specific times or at specific distances based on a user's monitored heart rate or heart rate trends over time. For example, a control command for an actuator may dictate a certain heart rate zone for a certain amount of time or distance, and a difficulty level of this control command may be dynamically scaled based on a user's monitored heart rate in order to get or keep the user in the certain heart rate zone for the certain amount of time or distance.

Using a control command, received at the receiving port 152 in a video workout program, such as a control command that is decoded from a subtitle stream of a video of a video workout program for example, the processing unit 150 may control the actuator 154 on the exercise machine 120 in the sequence and at the times or distances specified by the control command. For example, actuator control commands that provide the processing unit 150 with commands for controlling a belt motor, an incline motor, a flywheel brake, stride length motor, or another actuator may be included in the control commands received in a video workout program at the exercise machine 120.

Actuator control commands can be received for different time segments or distance segments of a workout. For example, a ten minute workout may have twenty different control commands that provide the processing unit 150 with a different control command for controlling an actuator every thirty seconds. Alternatively, a ten mile workout may have twenty different control commands that provide a processing unit with a different control command for controlling an actuator every half mile. Workouts may be of any duration or distance and different control commands may be received at any time or distance during the workout. Alternatively, a 5 minute workout may have 300 different control commands that provide the processing unit 150 with a different control command for controlling an actuator once per second.

The control commands received in a video workout program at the exercise machine 120 may be executed by the processing unit 150 in a number of different ways. For example, the control commands may be received and then stored into a read/write memory that is included in the processing unit 150. Alternatively, the control commands may be streamed to the exercise machine 120 in real-time. The control commands may also be received and/or executed from a portable memory device, such as a USB memory stick or an SD card.

Video workout programs may include a plurality of control commands that provide instructions for different types of exercise machines. For example, a video workout program may include a first set of control commands for controlling a belt motor and an incline motor on a treadmill, as well as a second set of control commands for controlling a flywheel brake, an incline motor, and a stride length motor of an elliptical machine. Where the exercise machine 120 is a treadmill, the processing unit 150 of the exercise machine 120 may be configured to recognize and select the first set of control commands that provides instructions for a treadmill, while ignoring the second set of control commands that provides instructions for an elliptical machine. Similarly, where the exercise machine 120 is an elliptical machine, the processing unit 150 of the exercise machine 120 may be configured to recognize and select the second set of control commands that provides instructions for an elliptical machine, while ignoring the first set of control commands that provides instructions for a treadmill.

In addition to recognizing and selecting the compatible set of control commands, the processing unit 150 may also apply a sizing restriction to control commands before the control commands can be executed by the exercise machine 120. As with recognizing the compatible set of control commands, the processing unit 150 may use reference data to determine whether a sizing restriction is necessary and, if so, apply the sizing restriction. Application of a sizing restriction to compatible control commands may be necessary due to the fact that the moveable members 126 on the exercise machine 120 have operating parameters that are adjustable only within a limited range. Thus, even if two exercise machines have the same type of actuator (i.e., both a treadmill and an elliptical machine may have incline motors), sets of control commands for that actuator may not be compatible with both exercise machines.

FIGS. 3A-3D illustrate video frames and charts that may be employed in controlling an exercise machine using exercise machine control commands of a video workout program that are encoded into a subtitle stream of a video of the video workout program. In particular, FIGS. 3A-3D illustrate frames 300*a*-300*d* of video captured by the videographer 110*a* (see FIG. 1) of the trainer 108*a* performing a workout, which may include running a marathon along a path 306. Further, FIGS. 3A-3D also illustrate data charts 302*a*-302*d* which contain certain relevant data parameters gathered during the workout at the same time that the corresponding frame of video is captured, manually or automatically using one or more sensors, for example. Finally, FIGS. 3A-3D also illustrate comma separated values (CSV) encoding charts 304a-304d showing how the data parameters from the data charts 302a-302d is translated and encoded into control commands.

The frames 300a-300d of video captured of the trainer 108a running the marathon represent frames of video captured in succession, one second apart. It is understood, however, that other intervening frames of video may also be captured, such as 29 intervening frames of video between each of the successive frames 300a-300d, resulting in a captured video having 30 frames per second. The reason that only one frame per second are illustrated in the frames 300a-300d of video is because the encoding of control commands of a video workout program into a subtitle stream of a video of the video workout program may only occur only once per second in the example encoding disclosed in FIGS. 3A-3D. Other encoding rates are also possible, such as encoding twice per second or four times per second, for example. In some embodiments, the encoding rate may be up to as many times per second as there are frames per second (e.g., where the frame rate is 30 frames per second, the encoding rate may up to 30 times per second).

Figure 3A:
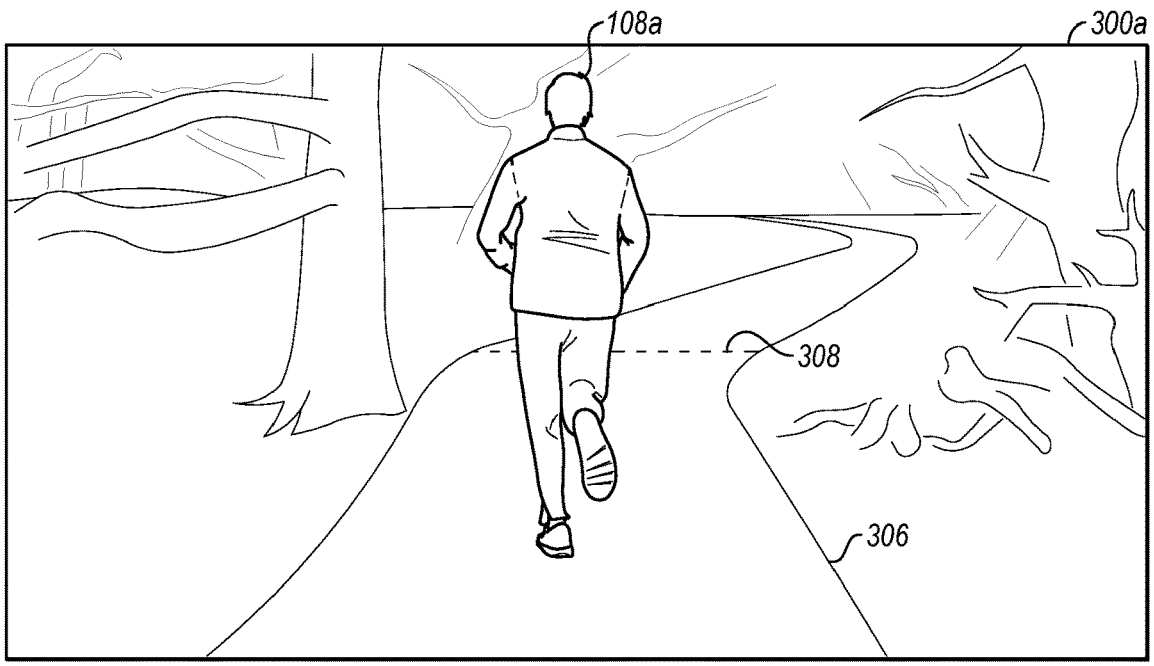
FIGS. 3A-3D illustrate video frames and charts that may be employed in controlling an exercise machine using exercise machine control commands of a video workout program that are encoded into a subtitle stream of a video of the video workout program.

As disclosed in the frame 300a of FIG. 3A, the trainer 108a may be performing a workout by running a marathon along the path 306. As disclosed in the data chart 302a, at the time that the frame 300a is captured by a video camera, 605 seconds may have transpired since the start of the workout, the trainer 108a may be running at a pace of 6 miles per hour up a 0.5% incline, the trainer 108a may currently be in a heart rate zone 3 with a heart rate of 150 beats per minute, and may be in a workout state of "In Workout" (as opposed to a workout state of "Warmup" or "Cool Down"). As disclosed in the CSV encoding chart 304a, the data parameters from the data chart 302a may be encoded into a CSV encoding 305a in a subtitle stream of a video, which is timed with (e.g., linked or tied to) the frame 300a, as "605,6,0.5, 0,0,0,3,150,1", which represents 605 seconds since the start of the workout, a speed of 6 miles per hour, a 0.5% incline, resistance being non-applicable (with N/A being represented by a 0), a target revolutions per minute being non-applicable (with N/A being represented by a 0), a target watts being non-applicable (with N/A being represented by a 0), a target heart rate zone of 3, a target heart rate of 150, and a workout state of 1 (which represents a workout state of "In Workout"). In some embodiments, the CSV encoding 305a may have all values separated by a comma, may have all values be numbers (e.g., numbers between −99999.0 to 99999.0), may not have spaces between values, may encode values in order (e.g., so that the position of each value can be used to interpret the meaning of each value), and may allow for a new value if the new value is appended at the end of the CSV encoding.

Figure 3B:
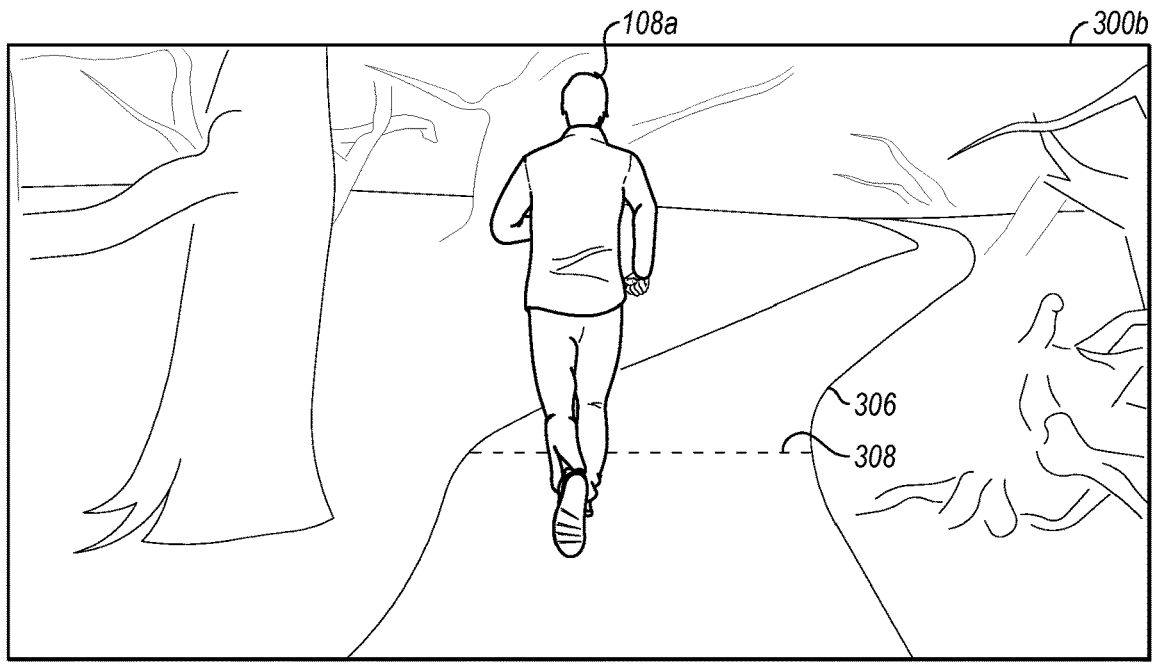

As disclosed in the frame 300b of FIG. 3B, the trainer 108a may continue performing the workout by running the marathon along the path 306. As disclosed in the data chart 302b, at the time that the frame 300b is captured by a video camera, 606 seconds may have transpired since the start of the workout (e.g. one additional second has transpired since the frame 300a was captured), the trainer 108a may still be running at a pace of 6 miles per hour up a 0.5% incline, the trainer 108a may still be in heart rate zone 3 but with an increased heart rate of 152 beats per minute, and may still be in a workout state of "In Workout." As illustrated in frame 300b, the trainer 108a may be approaching a transition 308 in the path 306 where the incline transitions from a relatively gradual 0.5% incline to a relatively steep 4.5% incline. As disclosed in the CSV encoding chart 304b, the data parameters from the data chart 302b may be encoded into a CSV encoding 305b in a subtitle stream of a video, which is timed with frame 300b, as "606,6,0.5,0,0,0,3,152,1".

Figure 3C:
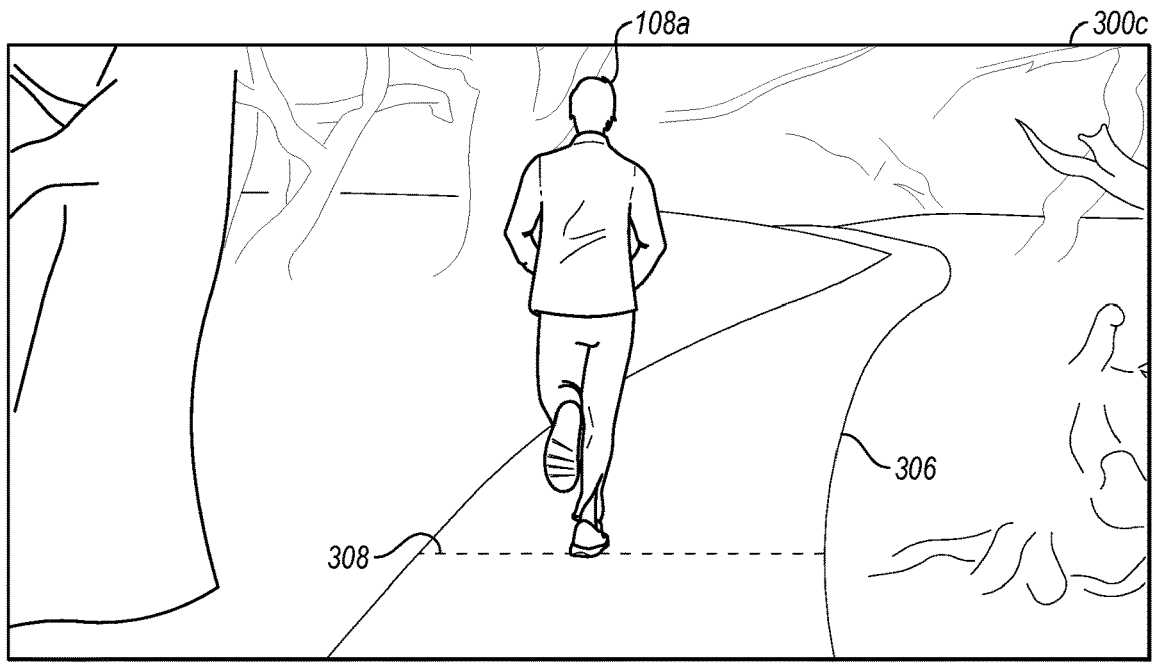

As disclosed in the frame 300c of FIG. 3C, the trainer 108a may continue performing the workout by running the marathon along the path 306. As disclosed in the data chart 302c, at the time that the frame 300c is captured by a video camera, 607 seconds may have transpired since the start of the workout (e.g. one additional second has transpired since the frame 300b was captured, and two additional seconds have transpired since the frame 300a was captured), the trainer 108a may now have slowed to running at a pace of 5 miles per hour up a 4.5% incline, the trainer 108a may still be in heart rate zone 3 but with an increased heart rate of 156 beats per minute, and may still be in a workout state of "In Workout." As illustrated in frame 300c, the trainer 108a may have crossed over the transition 308 in the path 306 where the incline transitions from the relatively gradual 0.5% incline to the relatively steep 4.5% incline, which may account for the slower speed and increased heart rate of the trainer 108a. As disclosed in the CSV encoding chart 304c, the data parameters from the data chart 302c may be encoded into a CSV encoding 305c in a subtitle stream of a video, which is timed with the frame 300c, as "607,5,4.5, 0,0,0,3,156,1".

Figure 3D:
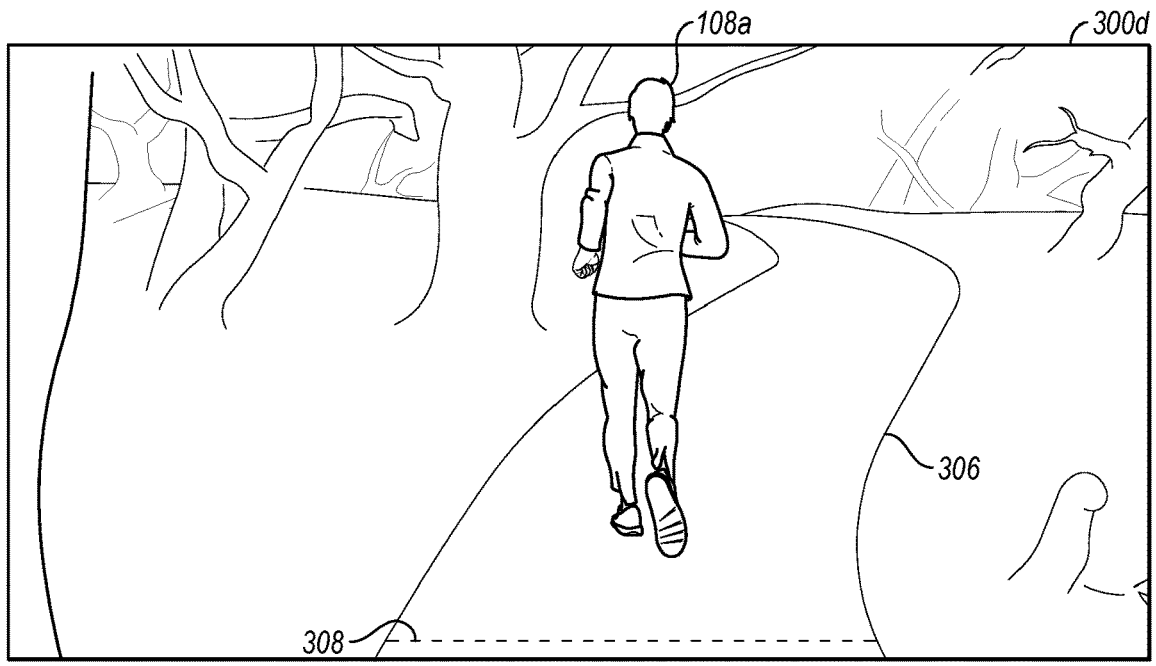

As disclosed in the frame 300d of FIG. 3D, the trainer 108a may continue performing the workout by running the marathon along the path 306. As disclosed in the data chart 302d, at the time that the frame 300d is captured by a video camera, 608 seconds may have transpired since the start of the workout (e.g. one additional second has transpired since the frame 300c was captured, two additional seconds have transpired since the frame 300b was captured, and three additional seconds have transpired since the frame 300a was captured), the trainer 108a may still be running at a pace of 5 miles per hour up a 4.5% incline, the trainer 108a may still be in heart rate zone 3 but with an increased heart rate of 160 beats per minute, and may still be in a workout state of "In Workout." As disclosed in the CSV encoding chart 304d, the data parameters from the data chart 302d may be encoded into a CSV encoding 305d in a subtitle stream of a video, which is timed with the frame 300d, as "608,5,4.5,0,0,0,3, 160,1".

Due to the fact that, in a video, the frames 300a-300d from the video are timed with frames of the subtitle stream, the encoding of control commands in a subtitle stream, such as in the CSV encodings 305a-305d illustrated in the CSV encoding charts 304a-304d, maintains synchronization of the video of a video workout program and of corresponding control commands of the video workout program. For example, even if the video is buffered or otherwise delayed, the subtitle stream will also be buffered or otherwise delayed by an identical amount, which will maintain synchronization of the video and of corresponding control commands. This synchronization between a video and corresponding control commands in a video workout program can enable a user to become immersed in a workout on the exercise machine, which may help the user to avoid the boredom and burnout that is often experienced by users of exercise machines.

Figure 4A:
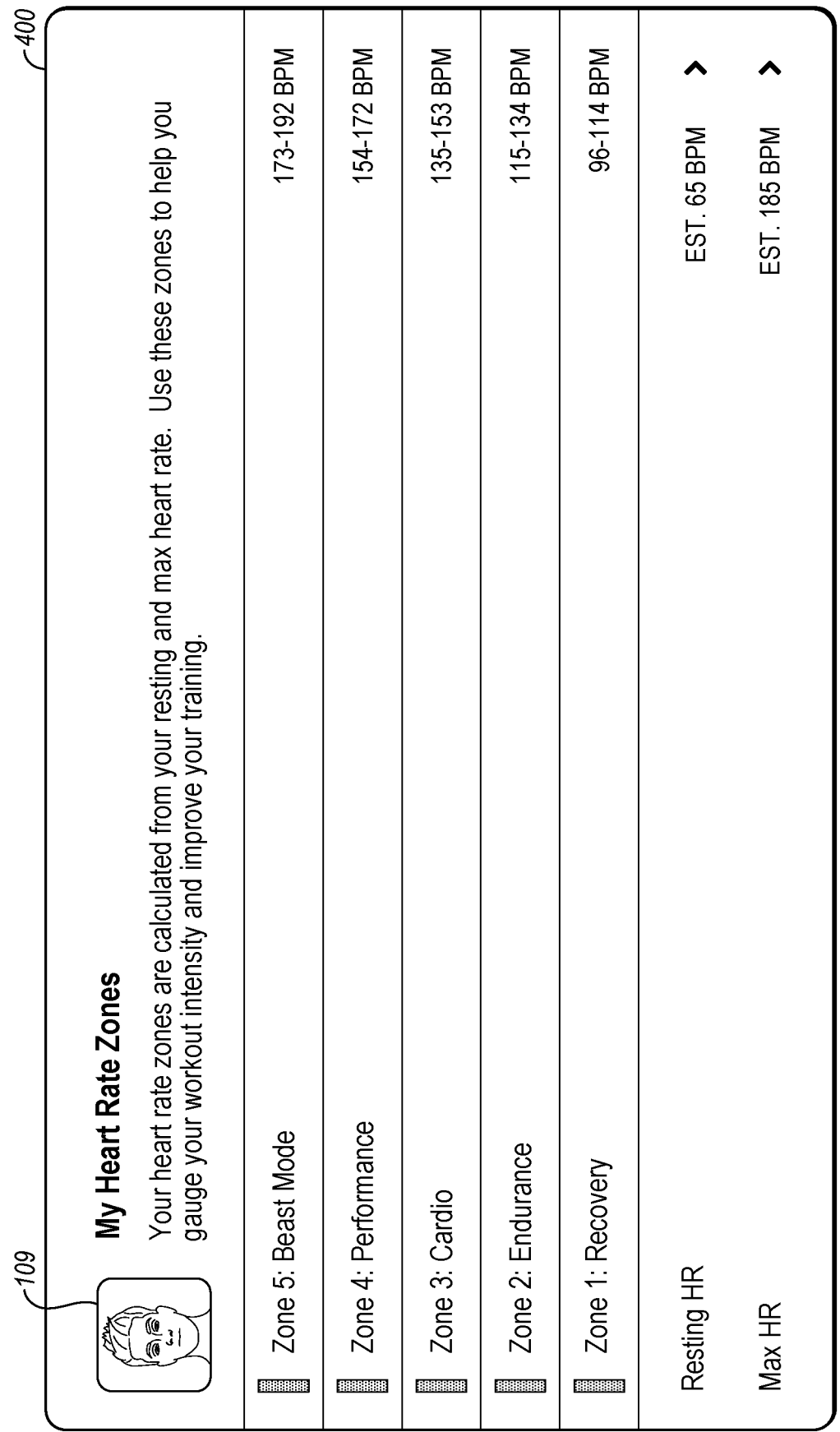
FIG. 4A illustrates a chart of a heart rate zones for a user based on the user's resting heart rate and max heart rate.

FIG. 4A illustrates a chart 400 of a heart rate zone for a user 109 based on the resting heart rate and max heart rate of the user 109. The difference between the max heart rate and the resting heart rate of the user 109 is known as a heart rate reserve (HRR). Some embodiments may employ heart rate reserved to calculate heart rate zones, rather than using a simple percentage of max heart rate, which may allow for zones to be calculated just on the values that the heart actual capable of beating at. As disclosed in the chart 400, the user 109 may have a measured or estimated resting heart rate of 65 beats per minute (BPM) as well as a measured or estimated max heart rate of 185 BPM. Based on these two data points, five heart rate zones for the user 109 may be calculated. In particular, as illustrated in the chart 400, each heart rate zone may be associated with a particular range of heart rates, such as 96-114 BPM for heart rate Zone 1, or 173-192 BPM for heart rate Zone 5. In some embodiments, prior to performing a video workout program, the resting heart rate as well as the max heart rate of a user may be obtained in order to calculate heart rate Zone 1 to heart rate Zone 5. Due to the fact that the resting heart rate and the max heart rate may vary from user to user, the calculated heart rate Zone 1 to heart rate Zone 5 may also vary from user to user.

In some embodiments, the resting heart rate and max heart rate in the chart 400 may be measured or estimated. For example, even though resting heart rate and max heart rate may be initially estimated for the user 109, the user 109 may be allowed to override the initial estimated values if the user 109 knows their resting heart rate or max heart rate. Further, instructions may be provided to the user 109 regarding how to properly measure or test their resting heart rate and/or max heart rate. For example, the treadmill 120a of FIG. 1 may be configured to provide a test that can be performed on the treadmill 120a to accurately test the max heart rate of the user 109. This may be a graded test that gets progressively harder until the user 109 hits their max heart rate. The user 109 may perform the test for as long as they can. When the user 109 ends the test, the treadmill 120a may automatically save the max heart rate of the user 109, and then recompute the heart rate zones shown in the chart 400 for the user 109. Similarly, anytime the user 109 adjusts their resting heart rate or max heart rates, the heart rate zones of the user 109 may be automatically shifted to reflect those new values. Also, it is noted that a max heart rate for a user 109 may be different for different exercise modalities, such as for difference exercise machines. For example, a max heart rate for the user 109 may be lower on the rower machine 120d (e.g., because it is not a weight bearing exercise machine) than on the treadmill 120a (because it is a weight bearing exercise machine). Therefore, for any given user, a difference max heart rate may be used for different exercise modalities.

FIG. 4B illustrates a chart 450 of programmed heart rate zones for a video workout program. As disclosed in the chart 450, the video workout program may include multiple programmed heart rate zones (i.e., zone 2 to zone 5, or Z2 to Z5) corresponding to the depiction of the trainer in the video. In particular, the programmed heart rate zone transitions from zone 2, to zone 4, to zone 5, to zone 4, to zone 2, to zone 3, to zone 2, to zone 4, to zone 2, to zone 4, to zone 5, and to zone 4. Each of the transitions may occur at a particular time during the video workout program, and may correspond to a commensurate change in the heart rate zone of the trainer shown in the video of the video workout program. In order to enable the exercise machine to automatically and adaptively scale the current difficulty level of the video workout program so that the user's heart rate zone tracks closely to the programmed heart rate zones, the user's heart rate may be continually monitored. Further, the trends of the user's heart rate may also be taken into consideration in order to avoid the current difficulty level from being changed too often and/or too dramatically.

FIGS. 5A-5D illustrate video frames and data charts that may be employed in dynamically scaling a video workout program on an exercise machine based on heart rate monitoring. In particular, FIGS. 5A-5D illustrate frames 500a-500d of video captured by the videographer 110a (see FIG. 1) of the trainer 108a performing a workout, which may include running a marathon along a path 506. Further, FIGS. 5A-5D also illustrate data charts 502a-502d which contain certain relevant data parameters. These data parameters may be gathered during the workout at the same time that the corresponding frame of video is captured, or may be gathered at or around the time that the corresponding frame of video is displayed. These data parameters may be gathered manually, by listening to voice commands of the trainer 108a for example. These data parameters may alternatively be gathered automatically, using one or more sensors for example.

Finally, FIGS. 5A-5D also illustrate widgets 508a-508d and 510a-510d which may overlay the frames 500a-500d, respectively, when dynamic scaling based on heart rate monitoring is active during a workout. In some embodiments, the dynamic scaling can be toggled on and off by a user using, for example, a "Smart HR Training" control. Further, in some embodiments, the chart 400 of FIG. 4A may be displayed when a user selects the header of any of the widgets 508a-508d or 510a-510d.

The frames 500a-500d of a video, which show the trainer 108a running the marathon, represent frames of video captured over time. It is understood, however, that other intervening frames of video may also be captured between each of the frames 500a-500d, resulting in a captured video having additional frames (e.g., with a frame rate of 24, 30, or 60 frames per second).

As disclosed in the frame 500a of FIG. 5A, the trainer 108a may be performing a workout by running a marathon along the path 506. As disclosed in the data chart 502a, at the time that the frame 500a is captured by the video camera 106a (see FIG. 1), the trainer 108a may be performing, and/or may direct that a user perform, the workout at a current programmed heart rate zone of zone 2, which for the user 109 of FIG. 4A corresponds to a personalized current programmed heart rate zone range of 115-134 BPM. As illustrated in the heart rate training widget 508a and in the data chart 502a, the previous programmed heart rate zone was zone 4, the time since the workout began is 450 seconds, the time since the most recent zone change is 70 seconds, the time remaining in the current programmed heart rate zone is 50 seconds, and the time remaining in the workout is 1350 seconds. As disclosed in the data chart 502a, the heart rate monitoring rate is once per second, the threshold heart rate trend rate is −5 seconds, the warmup time threshold is 180 seconds, and the user's last ten actual heart rates (in BPM) are 122, 122, 123, 123, 124, 124, 125, 124, 125, and 125. Also disclosed in the data chart 502a, the baseline difficulty level is $B_0$ with a baseline speed of 4 MPH, while the current difficulty level is $B_2$ with a current speed of 4.3 MPH. Finally, the data chart 502a also discloses that the user's actual heart rate is 125 BPM, which corresponds to the user's actual heart rate zone of zone 2, and the user's actual heart rate zone range of 115-134 BPM. Some or all of the data in data chart 502a may be employed to determine that the current difficulty level of the video workout program, of which the frame 500a is a part, should not be dynamically scaled because the user is already performing in the proper zone (i.e., zone 2).

As disclosed in the frame 500b and data chart 502b of FIG. 5B, the trainer 108a may be performing, and/or may direct that a user perform, the workout at a current programmed heart rate zone of zone 3, which for the user 109 of FIG. 4A corresponds to a personalized current programmed heart rate zone range of 135-153 BPM. As illustrated in the heart rate training widget 508b and in the data chart 502b, the previous programmed heart rate zone was zone 2, the time since the workout began is 675 seconds, the time since the most recent zone change is 60 seconds, the time remaining in the current programmed heart rate zone is 60 seconds, and the time remaining in the workout is 1125 seconds. As disclosed in the data chart 502b, the heart rate monitoring rate is once per second, the threshold heart rate trend rate is +4 seconds, the warmup time threshold is 180 seconds, and the user's last ten actual heart rates (in BPM) are 152, 152, 153, 153, 154, 154, 155, 155, 155, and 155. Also disclosed in the data chart 502b, the baseline difficulty level is $B_0$ with a baseline speed of 6 MPH, while the current difficulty level is $B_2$ with a current speed of 6.7 MPH. Finally, the data chart 502b also discloses that the user's actual heart rate is 155 BPM, which corresponds to the user's actual heart rate zone of zone 4, and the user's actual heart rate zone range of 154-172 BPM. Some or all of the data in data chart 502b may be employed to determine that the current difficulty level of the video workout program, of which the frame 500b is a part, should be dynamically scaled downward to move the user into the proper zone (i.e., from heart rate zone 4 to heart rate zone 3).

As disclosed in the frame 500c and data chart 502c of FIG. 5C, the trainer 108a may be performing, and/or may direct that a user perform, the workout at a current programmed heart rate zone of zone 2, which for the user 109 of FIG. 4A corresponds to a personalized current programmed heart rate zone range of 115-134 BPM. As illustrated in the heart rate training widget 508c and in the data chart 502c, the previous programmed heart rate zone was zone 3, the time since the workout began is 810 seconds, the time since the most recent zone change is 50 seconds, the time remaining in the current programmed heart rate zone is 70 seconds, and the time remaining in the workout is 990 seconds. As disclosed in the data chart 502c, the heart rate monitoring rate is once per second, the threshold heart rate trend rate is −4 seconds, the warmup time threshold is 180 seconds, and the user's last ten actual heart rates (in BPM) are 131, 131, 132, 133, 133, 134, 135, 136, 136, and 137. Also disclosed in the data chart 502c, the baseline difficulty level is $B_0$ with a baseline speed of 4 MPH, while the current difficulty level is $B_1$ with a current speed of 4.2 MPH. Finally, the data chart 502c also discloses that the user's actual heart rate is 137 BPM, which corresponds to the user's actual heart rate zone of zone 3 and the user's actual heart rate zone range of 135-153 BPM. Some of all of the data in data chart 502c may be employed to determine that the current difficulty level of the video workout program, of which the frame 500c is a part, should be dynamically scaled downward to move the user into the proper zone (i.e., from heart rate zone 3 to heart rate zone 2).

As disclosed in the frame 500d and data chart 502d of FIG. 4D, the trainer 108a may be performing, and/or may direct that a user perform, the workout at a current programmed heart rate zone of zone 4, which for the user 109 of FIG. 4A corresponds to a personalized current programmed heart rate zone range of 154-172 BPM. As illustrated in the heart rate training widget 508d and in the data chart 502d, the previous programmed heart rate zone was zone 2, the time since the workout began is 1020 seconds, the time since the most recent zone change is 120 seconds, the time remaining in the current programmed heart rate zone is 120 seconds, and the time remaining in the workout is 780 seconds. As disclosed in the data chart 502d, the heart rate monitoring rate is once per second, the threshold heart rate trend rate is +5 seconds, the warmup time threshold is 180 seconds, and the user's last ten actual heart rates (in BPM) are 148, 147, 148, 149, 149, 149, 150, 150, 150, and 150. Also disclosed in the data chart 502d, the baseline difficulty level is $B_0$ with a baseline speed of 8 MPH, and the current difficulty level is also $B_0$ with a current speed of 8 MPH. Finally, the data chart 502d also discloses that the user's actual heart rate is 150 BPM, which corresponds to the user's actual heart rate zone of zone 3, and the user's actual heart rate zone range of 135-153 BPM. Some of all of the data in data chart 502d may be employed to determine that the current difficulty level of the video workout program, of which the frame 500b is a part, should be dynamically scaled upward to move the user into the proper zone (i.e., from heart rate zone 3 to heart rate zone 4).

During the video workout program in which the heart rate training widget 508a-508d are displayed to the user 109, two states are displayed, namely, (1) a programmed state 509 which displays the programmed heart rate zone for the entire video workout program, and (2) a historical state 511a-511d which shows the historical heart rate zone (and/or the corresponding heart rate) of the user from the beginning of the video workout program to the current point in time in the video workout program. These two displayed states enable the user to track their actual heart rate performance (using the historical state 511a-511d) against the programmed heart rate performance (using the programmed state 509) for the video workout program.

During the video workout program in which the frames 500a-500d from the video are displayed to the user 109, the current difficulty level may be dynamically scaled based on the monitored heart rate of the user 109 of FIG. 4A. However, due to the fact that the direction and speed at which the heart rate of the user 109 is trending is also being continually monitored, the video workout program may avoid changing the current difficulty level too often and/or too dramatically. Thus, the enjoyment of the user 109 may be increased, the inadvertent operation of the exercise machine (e.g., the treadmill 120a of FIG. 1) at a difficulty level that is not optimal for the fitness level of the user 109 may be avoided, and the integrity between the workout of the trainer 108a shown in the frames 500a-500d from the video and the actual workout performed by the user 109 can be maintained, thus increasing the ability of the user 109 to become more immersed in the workout on the exercise machine.

Figure 6A:
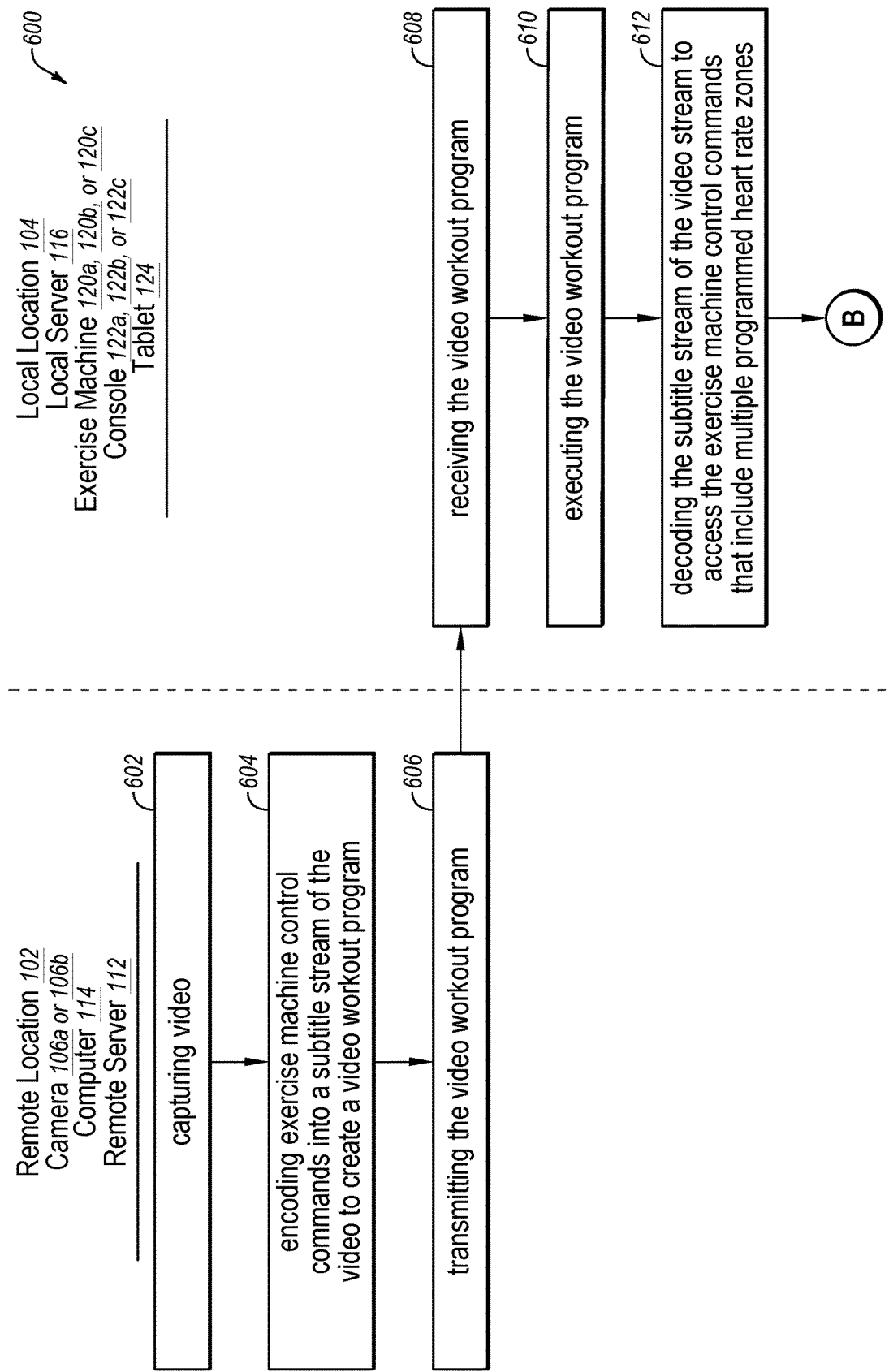
FIGS. 6A-6B illustrate a flowchart of an example method for controlling an exercise machine using a video workout program.
Figure 6B:
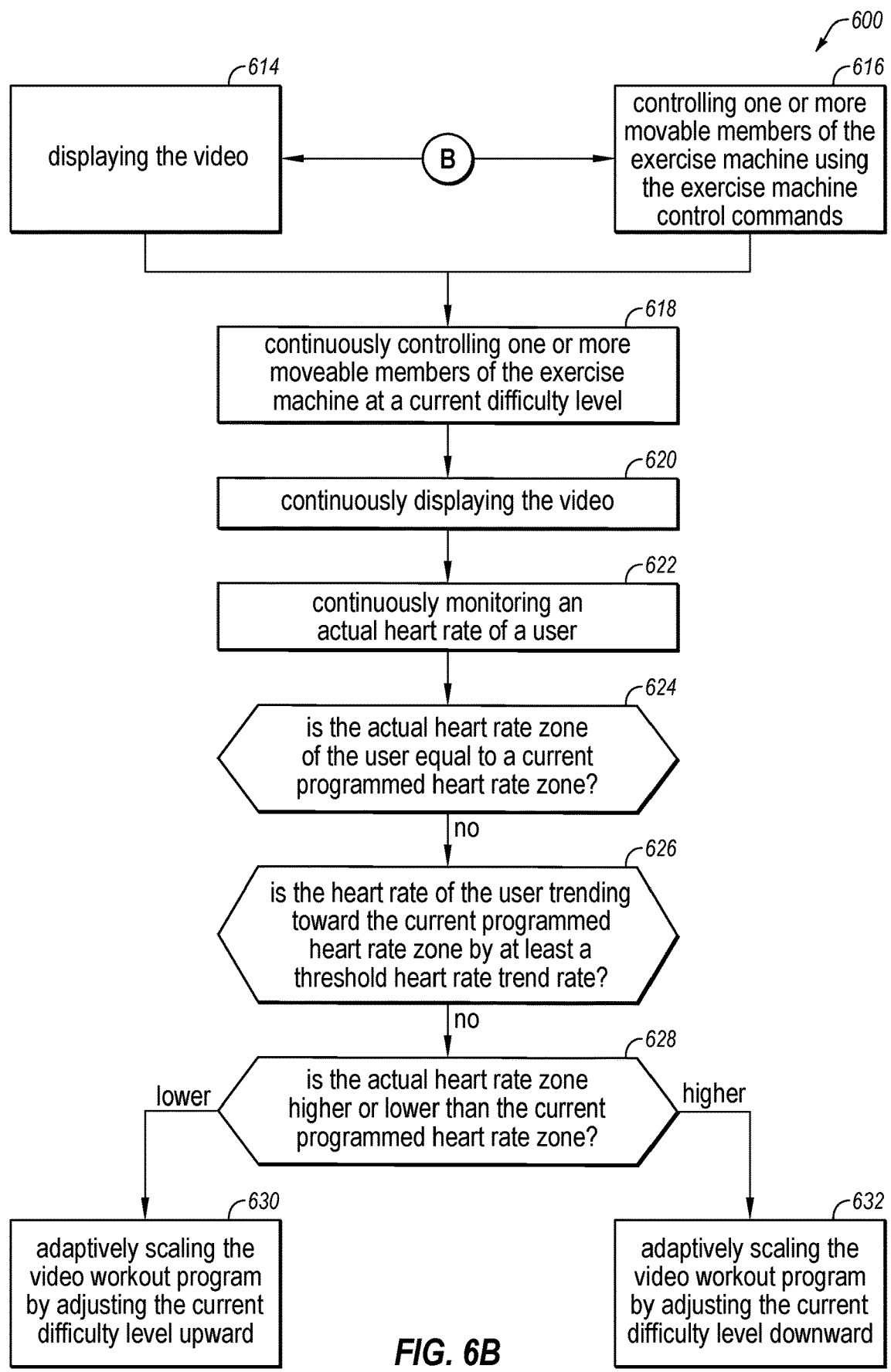

FIGS. 6A-6B illustrates a flowchart of an example method 600 for controlling an exercise machine using a video workout program. The method 600 may be performed, in some embodiments, by one or more applications, devices, or systems, such as by the video cameras 106a-106b, the computer 114, the remote server 112, the local server 116, the exercise machines 120a-120d, the consoles 122a-122d, and/or the tablet 124, or some combination thereof. In these and other embodiments, the method 600 may be performed by one or more processors based on one or more computer-readable instructions stored on one or more non-transitory computer-readable media. The method 600 will now be described in connection with FIGS. 1, 2, 3A-3D, 4A-4B, 5A-5D, and 6.

Prior to the method 600, a user may be subscribed to a subscription service (e.g., an IFIT account) that allows the user to have access to video workout programs. This subscription service may store user profile, as well as history information related to a user's sleep, nutrition, stress levels, exercise, wellness, and activity levels (which may be gathered automatically via sensors, or manually entered by the user). This profile and history information may be accessed to recommend particular video workout programs that will best help a user to achieve fitness goals set by the user or automatically generated for the user. By providing high quality video workout programs, a user may be incentivized to continue subscribing, and a retention rate for subscribers may be positively impacted. Further, some video workout programs created using the method 600 may be accessed by user using a pay-per-view model rather than an ongoing subscription model. For example, a pay-per-view model may be appropriate for rare events or classes, or for one-on-one training sessions between a single trainer and a single user.

Further, prior to the method 600, a pre-roll video of a video workout program may be displayed to a user. For example, prior to the start time of a live or pre-recorded exercise class or sporting event, there may be several minutes (e.g., 10 minutes) of pre-roll video that a user may view while waiting for the class or event to begin. This pre-roll video may include pre-recorded video or live video, or may alternate between the two (e.g., begin with prerecorded video at 10 before the start time and then cutting to live video of a trainer at 5 minutes before the start time). This pre-roll video may include a countdown clock to the start time of the class or event. In some embodiments, this pre-roll video does not include control commands encoded into the subtitle stream due to this encoding beginning at the start time of the class or event. In other embodiments, there may be pre-class or pre-event control commands encoded in the subtitle stream of the pre-roll video, such as control commands to adjust environmental control devices in the room (e.g., to adjust the temperature, lighting, music, etc. of the room).

The method 600 may include, at action 602, capturing video. For example, the video camera 106a may be employed by the videographer 110a to capture, at action 602, video of the trainer 108a performing a workout. In this example, the workout being performed by the trainer 108a may be running a marathon, and the video may be transmitted from the video camera 106a to the remote server 112 for further processing.

The method 600 may include, at action 604, encoding exercise machine control commands into a subtitle stream of the video to create a video workout program. For example, the computer 114 may be employed by a producer to encode, at action 604, exercise machine control commands into a subtitle stream of the video (that was sent to the remote server 112) to create a video workout program. These exercise machine control commands may be targeted for a particular type of exercise machine, such as the treadmill 120a.

In some embodiments, the exercise machine control commands may be encoded as comma separated values (CSVs). For example, the computer 114 may be employed by a producer to encode, at action 604, exercise machine control commands into the CSV encoding 305a, 305b, 305c, or 305d.

In some embodiments, the exercise machine control commands may be configured to control one or more of a speed of one or more moveable members of the exercise machine, an incline percentage of one or more moveable members of the exercise machine, or a resistance of one or more moveable members of the exercise machine. For example, the CSV encoding 305a, 305b, 305c, or 305d may include a control command configured to control one or more of the speed (e.g., in the $2^{nd}$ position of the CSV encoding), the incline percentage (e.g., in the $3^{rd}$ position of the CSV encoding), or the resistance (e.g., in the $4^{th}$ position of the CSV encoding) of one or more moveable members 126a-126h of the exercise machine 120a, 120b, or 120c.

In some embodiments, the comma separated values may further include workout data associated with a workout depicted in the video. This workout data may include one or more of a target revolutions per minute (RPM) for the workout, a target watts for the workout, a target heart rate zone for the workout, a target heart rate for the workout, a current number of seconds since a start of the workout, and a workout state of the workout. In some embodiments, the workout state may include a warmup state, an in-workout state, or a cooldown state. For example, the CSV encoding 305a, 305b, 305c, or 305d may include workout data associated with the workout depicted in the video from the video, which in this example is the running of a marathon. This workout data may include one or more of a target RPM for the workout (e.g., in the $5^{th}$ position of the CSV encoding), a target watts for the workout (e.g., in the $6^{th}$ position of the CSV encoding), a target heart rate zone for the workout (e.g., in the $7^{th}$ position of the CSV encoding), a target heart rate for the workout (e.g., in the $8^{th}$ position of the CSV encoding), a current number of seconds since a start of the workout (e.g., in the $1^{st}$ position of the CSV encoding), and a workout state of the workout (e.g., in the $9^{th}$ position of the CSV encoding). In this example, the workout state may be encoded as a 0 for a warmup state, as a 1 for an in-workout state, and as a 2 for a cooldown state.

In some embodiments, changes in the exercise machine control commands may be synchronized with associated changes in a workout depicted in the video. For example, as the trainer 108a changes from running on a 0.5% incline to running on a 4.5% incline, which change is depicted in frames 300b and 300c of the video, the exercise machine control commands that are encoded with the frames 300b and 300c may be synchronized to reflect this change, namely, that the incline percentage should change from 0.5% to 4.5% (compare the $3^{rd}$ position of the CSV encoding 305b to the $3^{rd}$ position of the CSV encoding 305c).

In some embodiments, the encoding, at action 604, of the exercise machine control commands into the subtitle stream of the video, to create a video workout program, may be performed subsequent to the capturing, at action 602, of the video. For example, where the video workout program being produced is intended to be a pre-recorded video workout program that is to be performed by an exercise machine user sometime in the future, the encoding of the subtitle stream at action 604 may be performed by the computer 114 (either automatically or as employed by a producer) subsequent to the capturing of the video at action 602 (e.g., minutes, hours, or days after the capturing of the video).

In some embodiments, the encoding, at action 604, of the exercise machine control commands into the subtitle stream of the video, to create a video workout program, may be performed synchronously with the capturing, at action 602, of the video. For example, where the video workout program being produced is intended to be a live video workout program that is performed in real-time by an exercise machine user simultaneously with a live workout (such as a live exercise machine workout performed during a live event such as a live marathon or a live road bicycle race), the encoding of the subtitle stream at action 604 may be performed by the computer 114 (either automatically or as employed by a producer) synchronously with the capturing of the video at action 602 (e.g., during a live event).

The method 600 may include, at action 606, transmitting the video workout program and, at action 608, receiving the video workout program. For example, the remote server 112 may send, at action 606, and the console 122a of the exercise machine 120a may receive, at action 608, the video workout program, such as via the network 118 and the local server 116.

The method 600 may include, at action 610, executing, at an exercise machine, the video workout program. For example, the console 122a of the treadmill 120a may execute, at action 602, a video workout program. The video workout program may include a video that includes the frames 500a-500d that depict the trainer 108a performing a workout that includes running a marathon.

The method 600 may include, at action 612, decoding the subtitle stream of the video to access the exercise machine control commands. For example, the console 122a of the exercise machine 120a may decode the subtitle stream of the video of a video exercise program to access the exercise machine control commands. In this example, this decoding may include interpreting the values stored in the comma separated values encoding 305a, 305b, 305c, or 305d (e.g., by the position of each value), such as by decoding the $7^{th}$ positions of the CSV encodings as a target heart rate zones for the workout and by decoding the $8^{th}$ positions of the CSV encodings as target heart rates for the workout.

In this example, these exercise machine control commands corresponding to heart rates and heart rate zones may correspond to a depiction of a trainer in the video. For example, the video of the video workout program may include the frames 500a-500d that depict the trainer 108a performing a workout that includes running a marathon. The video workout program may also include the multiple programmed heart rate zones that are illustrated in the chart 450 (e.g., the programmed heart rate zones that transition from zone 2, to zone 4, to zone 5, to zone 4, to zone 2, to zone 3, to zone 2, to zone 4, to zone 2, to zone 4, to zone 5, and to zone 4) and that correspond to the heart rate zones of the trainer 108a as depicted in the video.

The method 600 may include, at action 612, decoding the subtitle stream of the video to access the exercise machine control commands. For example, the console 122a of the exercise machine 120a may decode the subtitle stream of the video to access the exercise machine control commands. In this example, this decoding may include interpreting the values stored in the comma separated values encoding 305a, 305b, 305c, or 305d (e.g., by the position of each value).

The method 600 may include, at action 614, displaying the video and, at action 616, controlling one or more moveable members of the exercise machine using the exercise machine control commands. In some embodiments, changes in the control of the one or more moveable members of the exercise machine may occur synchronously with associated changes in the workout being displayed in the video. For example, the console 122a of the exercise machine 120a may display the video, including the frames 300a-300d (which may be interleaved with other frames, since the frames 300a-300d are successively one second apart). Simultaneously, the console 122a of the exercise machine 120a may control the running belt 126a and the running deck 126b of the exercise machine 120a using the exercise machine control commands. In this example, when the console 122a receives and decodes the CSV encoding 305b, simultaneously to displaying the frame 300b, the console 122a may control the running belt 126a to operate at 6 miles per hour based on the control command "6" found in the $2^{nd}$ position of the CSV encoding 305b, and may control the running deck 126b to incline to 0.5% based on the control command "0.5" found in the $3^{rd}$ position of the CSV encoding 305b. Similarly, in this example, when the console 122a receives and decodes the CSV encoding 305c, simultaneously to displaying the frame 300c, which shows changes in the workout of the trainer 108a from running at 6 mph to 5 mph, and from running on an incline of 0.5% to running on an incline of 4.5%, the console 122a may control the running belt 126a to change from operating at 6 mph to 5 mph based on the control command "5" found in the $2^{nd}$ position of the CSV encoding 305c, and may control the running deck 126b to change from being inclined at 0.5% to being inclined at 4.5% based on the control command "4.5" found in the $3^{rd}$ position of the CSV encoding 305c. In this manner, as the trainer 108a transitions from running on a 0.5% incline to running on a 4.5% incline in the video, the treadmill 120a displaying the video as part of a workout can likewise transition its running deck 126b from a 0.5% incline to a 4.5% incline, thus mimicking the workout by the trainer 108a depicted in the video for a user on the treadmill 120a.

In some embodiments, the video may be transmitted, at action 606, from a location remote from the exercise machine and received, at action 608, at a location local to the exercise machine in a live broadcast to enable the executing at action 610, the decoding at action 612, the displaying at action 614, and the controlling at action 616 to occur during the performance of the workout at the location remote from the exercise machine, and to enable performance of a workout on the exercise machine at the location local to the exercise machine that mimics the performance of the workout at the location remote from the exercise machine. For example, where the video workout program being produced is intended to be a live video workout program that is performed by an exercise machine user simultaneously with a live workout (such as a workout performed during a live event, such as the Boston Marathon in Massachusetts), the encoding of the subtitle stream (at action 604) may be performed by the computer 114 as employed by a producer on-site at the remote location 102, such as on-site the Boston Marathon in Massachusetts (e.g., in a production truck parked near the finish line, or in a nearby production studio). Then, the live video workout program may be broadcast live over the network 118 (e.g., over the Internet via a satellite uplink from the production truck or nearby production studio, possibly through Amazon Web Services (AWS), which may require a drone or blimp to get reception in a jungle or on a mountain or in a canyon or when surrounded by large buildings) to a user located at the local location 104, such as to a user's home in California. This may enable the user in his home in California to perform a workout on the treadmill 120a that mimics the running of the Boston Marathon in Massachusetts, while the Boston Marathon is actually happening in Massachusetts. Further, in addition control commands encoded in the subtitle stream of the video, other information may be encoded in the video or otherwise included with the video, such as TWITTER or FACEBOOK or INSTAGRAM comments, or other types of comments received from users or trainers, such as over the Internet via an app or website. This other information may be encoded and/or included on-site (e.g., in a production truck parked near the finish line or in a nearby production studio).

The method 600 may include, at action 618, continuously controlling one or more moveable members of the exercise machine at a current difficulty level. For example, the console 122a of the treadmill 120a may continuously control the running belt 126a of the treadmill 120a, and/or the running deck 126b of the treadmill 120a, at a current difficulty level. In some embodiments, an initial difficulty level may be adjusted as necessary throughout the workout to help the user 109 maintain their heart rate in the proper heart rate zone, as discussed in connection with actions 630 and 632.

The method 600 may include, at action 620, continuously displaying the video. For example, the console 122a of the treadmill 120a may continuously display the video of the video workout program that includes the frames 500a-500d.

The method 600 may include, at action 622, continuously monitoring an actual heart rate of a user. In some embodiments, the continuously monitoring of the actual heart rate of the user may include continuously monitoring the actual heart rate of the user at least once per second, or at some other regular or irregular interval, such as twice per second, four times per second, eight times per second, once every two seconds, once every four seconds, or once every eight seconds. In some embodiments, the continuously monitoring of the actual heart rate of the user may include continually verifying that the user is actually using the exercise machine. For example, the console 122a of the treadmill 120a may continuously monitor the actual heart rate of the user 109, using the heart rate strap 111b or the heart rate watch 111a, once per second. The console 122a of the treadmill 120a may also continually verify that the user is actually using the treadmill 120a by analyzing the motor load of the treadmill 120a to identify if a user is actually putting a load on the motor, and/or by analyzing sensor data (such as a pressure plate sensor) to identify if a user is actually present, etc. This may prevent dynamic scaling of the video workout program if the user is still wearing the heart rate strap 111b or the heart rate watch 111a but has stepped off of the running belt 126a of the treadmill 120a, for example. Various other methods (beyond a pressure plate sensor) may be employed to detect that the user has stepped off the running belt 126a of the treadmill 120a. For example, a camera may be employed to detect if a user remains running on the running belt 126a. Also, where a user's heart rate slows even though the speed of the running belt 126a has not slowed may be an indication that the user has stepped off of the running belt 126a. Further, other safety measures may be implements for certain users, such as minors or the elderly or user who suffer from morbid obesity, which may be tied to a user's age or self-identified or detected ability level (which may be tied to data stored in the user's online account or profile) such as implementing a governor to cause a maximum speed and/or a maximum resistance level (or maximum workload). For example, a minor may be detected based on a weight being detected on the running belt 126a (e.g., based on a load on the motor or based on a weight scale) that is less than a threshold amount (e.g., under 100 pounds).

The method 600 may include, at action 624, determining whether the actual heart rate zone of the user is equal to a current programmed heart rate zone. If not (no at action 624), the method 600 may include, at action 626, determining whether the actual heart rate of the user is trending toward the current programmed heart rate zone by at least a threshold heart rate trend rate. If not (no at action 626), the method 600 may include, at action 628, determining whether the actual heart rate zone is higher or lower than the current programmed heart rate zone. If lower (lower at 628), the method 600 may include, at action 630, adaptively scaling the video workout program by adjusting the current difficulty level upward. If higher (higher at 628), the method 600 may include, at action 632, adaptively scaling the video workout program by adjusting the current difficulty level downward. In some embodiments, the actions 624 and 626 may be performed periodically and then, in response, the actions 628 and 630, or the actions 628 and 632, may be performed. In some embodiments, the periodically determining of the actions 624 and 626 may be performed once in each 10 second period of time, or some other regular or irregular time interval, such as once in each 5 second period of time, once in each 2 second period of time, once every second, once each 15 second period of time, or once in each 20 second period of time. In some embodiments, any actual heart rate that is determined to be an outlier may not be used in performance of the periodically determining of the actions 624 and 626.

For example, the console 122a of the treadmill 120a may determine, at action 624, that the actual heart rate zone (e.g., zone 4 in the data chart 502b) of the user 109 is not equal to a current programmed heart rate zone (e.g., zone 3 in the data chart 502b). Then, the console 122a of the treadmill 120a determine, at action 626, that the actual heart rate of the user 109 is not trending toward the current programmed heart rate zone (e.g., zone 3 in the data chart 502b) by at least a threshold heart rate trend rate (e.g., +4 seconds in the data chart 502b). Then, the console 122a of the treadmill 120a determine, at action 628, that the actual heart rate zone (e.g., zone 4 in the data chart 502b) is higher than the current programmed heart rate zone (e.g., zone 3 in the data chart 502b) and may adaptively scale, at action 632, the video workout program by adjusting the current difficulty level (e.g., the current difficulty level of $B_2$ at 6.7 MPH) downward (e.g., to a new current difficulty level of $B_1$ at 6.3 MPH).

In another example, the console 122a of the treadmill 120a may determine, at action 624, that the actual heart rate zone (e.g., zone 3 in the data chart 502d) of the user 109 is not equal to a current programmed heart rate zone (e.g., zone 4 in the data chart 502d). Then, the console 122a of the treadmill 120a determine, at action 626, that the actual heart rate of the user 109 is not trending toward the current programmed heart rate zone (e.g., zone 4 in the data chart 502d) by at least a threshold heart rate trend rate (e.g., +5 seconds in the data chart 502d). Then, the console 122a of the treadmill 120a determine, at action 628, that the actual heart rate zone (e.g., zone 3 in the data chart 502d) is lower than the current programmed heart rate zone (e.g., zone 4 in the data chart 502d) and may adaptively scale, at action 630, the video workout program by adjusting the current difficulty level (e.g., the current difficulty level of $B_0$ at 8.0 MPH) upward (e.g., to a new current difficulty level of $B_1$ at 8.7 MPH).

In some embodiments, the actions 624 and 626 may further include periodically determining at least that a time elapsed since the video workout program began executing is greater than a warmup-time threshold. For example, the console 122a of the treadmill 120a may determine, in connection with the actions 624 and 626, that the time elapsed since the video workout program began executing (e.g., 675 seconds in the data chart 502b) is greater than a warmup-time threshold (e.g., 180 seconds), in which case the current difficulty level would be adjusted upward or downward because a warmup period has been completed. If the contrary were true, however, the current difficulty level may not be adjusted upward due to a warmup period not having been completed.

In some embodiments, the actions 624 and 626 may further include periodically determining at least that a time elapsed since the video workout program began executing is less than a warmup-time threshold and that the actual heart rate zone is higher than the current programmed heart rate zone. For example, the console 122*a* of the treadmill 120*a* may determine, in connection with the actions 624 and 626, that the time elapsed since the video workout program began executing (e.g., 60 seconds) is less than a warmup-time threshold (e.g., 180 seconds) and that the actual heart rate zone (e.g., zone 3) is higher than the current programmed heart rate zone (e.g., zone 2), in which case the current difficulty level would be adjusted downward at action 632. This may enable a current difficulty level that is initially too difficult to be adjusted downward, even during a warmup period.

In some embodiments, the actions 624 and 626 may further include periodically determining at least that a time remaining in the current programmed heart rate zone is greater than a time-remaining threshold. For example, the console 122*a* of the treadmill 120*a* may determine, in connection with the actions 624 and 626, that a time remaining in the current programmed heart rate zone (e.g., 60 seconds in the data chart 502*b*) is greater than a time-remaining threshold (e.g., 10 seconds), in which case the current difficulty level would be adjusted upward or downward because there is sufficient time remaining in the current programmed heart rate zone for a change in the current difficulty level to be effective. If the contrary were true, however, the current difficulty level may not be adjusted upward or downward due to insufficient time remaining in the current programmed heart rate zone for a change in the current difficulty level to be effective.

In some embodiments, difficulty levels to which the current difficulty level can be adjusted may include a baseline difficulty level, a finite number of positive difficulty levels that are more difficult than the baseline difficulty level, and a finite number of negative difficulty levels that are less difficult than the baseline difficulty level. In some embodiments, the current difficulty level may be initially set to the baseline difficulty level, or may be initially set based on a history of performance of the user on the exercise machine. For example, the console 122*a* of the treadmill 120*a* may adjust the current difficulty level (e.g., the speed of the running belt 126*a*) between a baseline difficulty level (e.g., $B_0$=7.0 MPH), six positive difficulty levels (e.g., $B_1$=7.5 MPH, $B_2$=8.0 MPH, $B_3$=8.4 MPH, $B_4$=9.0 MPH, $B_5$=9.7 MPH, and $B_6$=10.5 MPH) that are more difficult than the baseline difficulty level, and six negative difficulty levels (e.g., $B_{-1}$=6.5 MPH, $B_{-2}$=6.0 MPH, $B_{-3}$=5.6 MPH, $B_{-4}$=5.0 MPH, $B_{-5}$=4.6 MPH, and $B_{-6}$=4.3 MPH) that are less difficult than the baseline difficulty level. In this example, the current difficulty level may be initially set to the baseline difficulty level (e.g., $B_0$=7.0 MPH), or may be set to a most recent or most common difficulty level of the user in previous workout(s) (e.g., if the user was most recently performing at a $B_{-3}$ level, the current difficulty level may be initially set to $B_{-3}$=5.6 MPH).

Subsequent to the method 600, a post-roll video of a video workout program may be displayed to a user. For example, after the finish time of a live or pre-recorded exercise class or sporting event, there may be several minutes (e.g., 10 minutes) of post-roll video that a user may view after finishing the class or event. This post-roll video may include pre-recorded video or live video, or may alternate between the two (e.g., begin with live video of the trainer at the finish time and then cutting to pre-recorded video at 5 minutes after the finish time). In some embodiments, this post-roll video does not include control commands encoded into the subtitle stream due to this encoding ending at the finish time of the class or event. In other embodiments, there may be post-class or post-event control commands encoded in the subtitle stream of the post-roll video, such as control commands to adjust environmental control devices in the room (e.g., to adjust the temperature, lighting, music, etc. of the room).

Further, subsequent to or during the method 600, an archive copy of a live video workout program may be created. This archive copy may store the exercise machine control commands together with the video, either encoded in the subtitle stream or in some other storage format. In this manner, a live video workout program may become an archived video workout program.

Further, the method 600 may be employed, in some embodiments, to convert older video workout programs with exercise machine control signals stored in another storage format into exercise machine control signals that are encoded into the subtitle stream of the video. This conversion may be performed programmatically or manually (such as on the fly while the video workout program is being broadcast).

In some embodiments, the method 600 may result in controlling an exercise machine using a video workout program. Unlike conventional methods of controlling an exercise machine that lack reliable synchronization between a video and corresponding workout control commands in a video workout program, the method 600 may maintain synchronization of the video and of corresponding control commands in a video workout program due to the fact that, in a video, frames from the video are timed with frames of a subtitle stream. This synchronization in the method 600 between a video and corresponding control commands in a video workout program can enable a user to become immersed in a workout on the exercise machine, which may help the user to avoid the boredom and burnout that is often experienced by users of exercise machines. Further, method 600 may result in the performance of a workout in which the current difficulty level may be dynamically scaled based on the monitored heart rate of the user 109. However, due to the fact that the direction and speed at which the heart rate of the user 109 is trending is also being continually monitored, the method 600 may avoid the video workout program from changing the current difficulty level too often and/or too dramatically. Thus, the method 600 may result in the enjoyment of the user 109 being increased, the inadvertent operation of the exercise machine (e.g., the treadmill 120*a* of FIG. 1) at a difficulty level that is not optimal for the fitness level of the user 109 being avoided, and the integrity between the workout of the trainer 108*a* shown in the frames 500*a*-500*d* from the video and the actual workout performed by the user 109 being maintained, thus increasing the ability of the user 109 to become more immersed in the workout on the treadmill 120*a*, which may help the user to avoid the boredom and burnout that is often experienced by users of exercise machines.

Although the actions of the method 600 are illustrated in FIGS. 6A and 6B as discrete actions, various actions may be divided into additional actions, combined into fewer actions, reordered, expanded, or eliminated, depending on the desired implementation. For example, in some embodiments, actions 604-616 may be performed without performing the other actions of the method 600. Further, in some embodiments, actions 618-630 or 632 may be performed without performing the other actions of the method 600.

Figure 7:
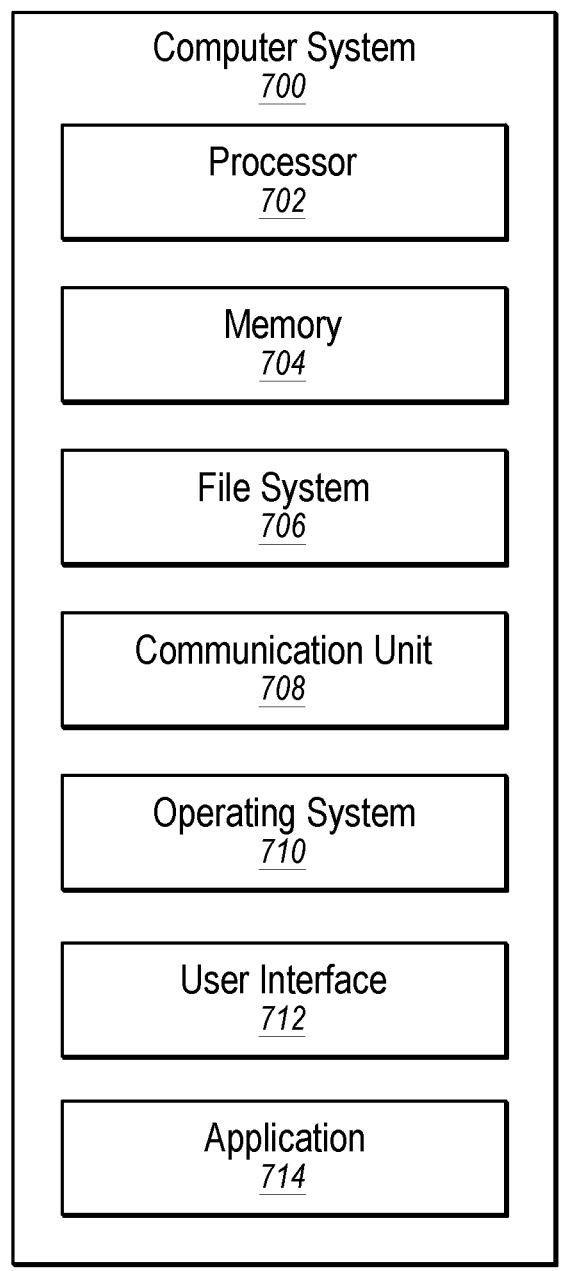
FIG. 7 illustrates an example computer system that may be employed in controlling an exercise machine using a video workout program.

FIG. 7 illustrates an example computer system 700 that may be employed in controlling an exercise machine using a video workout program. In some embodiments, the computer system 700 may be part of any of the systems or devices described in this disclosure. For example, the computer system 700 may be part of any of the video cameras 106a-106b, the computer 114, the remote server 112, the local server 116, the exercise machines 120a-120d, the consoles 122a-122d, or the tablet 124 of FIG. 1.

The computer system 700 may include a processor 702, a memory 704, a file system 706, a communication unit 708, an operating system 710, a user interface 712, and an application 714, which all may be communicatively coupled. In some embodiments, the computer system may be, for example, a desktop computer, a client computer, a server computer, a mobile phone, a laptop computer, a smartphone, a smartwatch, a tablet computer, a portable music player, an exercise machine console, a video camera, or any other computer system.

Generally, the processor 702 may include any suitable special-purpose or general-purpose computer, computing entity, or processing device including various computer hardware or software applications and may be configured to execute instructions stored on any applicable computer-readable storage media. For example, the processor 702 may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data, or any combination thereof. In some embodiments, the processor 702 may interpret and/or execute program instructions and/or process data stored in the memory 704 and/or the file system 706. In some embodiments, the processor 702 may fetch program instructions from the file system 706 and load the program instructions into the memory 704. After the program instructions are loaded into the memory 704, the processor 702 may execute the program instructions. In some embodiments, the instructions may include the processor 702 performing one or more actions of the method 600 of FIGS. 6A-6B.

The memory 704 and the file system 706 may include computer-readable storage media for carrying or having stored thereon computer-executable instructions or data structures. Such computer-readable storage media may be any available non-transitory media that may be accessed by a general-purpose or special-purpose computer, such as the processor 702. By way of example, and not limitation, such computer-readable storage media may include non-transitory computer-readable storage media including Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage media which may be used to carry or store desired program code in the form of computer-executable instructions or data structures and which may be accessed by a general-purpose or special-purpose computer. Combinations of the above may also be included within the scope of computer-readable storage media. Computer-executable instructions may include, for example, instructions and data configured to cause the processor 702 to perform a certain operation or group of operations, such as one or more actions of the method 600 of FIGS. 6A-6B. These computer-executable instructions may be included, for example, in the operating system 710, in one or more applications, or in some combination thereof.

The communication unit 708 may include any component, device, system, or combination thereof configured to transmit or receive information over a network, such as the network 118 of FIG. 1. In some embodiments, the communication unit 708 may communicate with other devices at other locations, the same location, or even other components within the same system. For example, the communication unit 708 may include a modem, a network card (wireless or wired), an infrared communication device, a wireless communication device (such as an antenna), and/or chipset (such as a Bluetooth device, an 802.6 device (e.g., Metropolitan Area Network (MAN)), a WiFi device, a WiMax device, a cellular communication device, etc.), and/or the like. The communication unit 708 may permit data to be exchanged with a network and/or any other devices or systems, such as those described in the present disclosure.

The operating system 710 may be configured to manage hardware and software resources of the computer system 700 and configured to provide common services for the computer system 700.

The user interface 712 may include any device configured to allow a user to interface with the computer system 700. For example, the user interface 712 may include a display, such as an LCD, LED, or other display, that is configured to present video, text, application user interfaces, and other data as directed by the processor 702. The user interface 712 may further include a mouse, a track pad, a keyboard, a touchscreen, volume controls, other buttons, a speaker, a microphone, a camera, any peripheral device, or other input or output device. The user interface 712 may receive input from a user and provide the input to the processor 702. Similarly, the user interface 712 may present output to a user.

The application 714 may be one or more computer-readable instructions stored on one or more non-transitory computer-readable media, such as the memory 704 or the file system 706, that, when executed by the processor 702, is configured to perform one or more actions of the method 600 of FIGS. 6A-6B. In some embodiments, the application 714 may be part of the operating system 710 or may be part of an application of the computer system 700, or may be some combination thereof.

INDUSTRIAL APPLICABILITY

Various modifications to the embodiments illustrated in the drawings will now be disclosed.

In general, some example methods disclosed herein may enable live or prerecorded video workout programs to be executed on an exercise machine that mimic workouts performed remotely from the exercise machine. For example, a workout may be performed by a trainer in an exotic remote location anywhere in the world, and a video of the workout being performed can be captured in a video workout program. Then, either subsequent to or synchronously with the capturing of the video, a subtitle stream of the video can be encoded with exercise machine control commands, that mimic the workout being performed in the remote exotic location, to create a video workout program. Then, the video workout program can be transmitted to a local location of an exercise machine, the video of the video workout program can be displayed to a user of the exercise machine, and the control commands of the video workout program can simultaneously be used to control the exercise machine to mimic, for the user on the exercise machine, the workout of the trainer in the exotic remote location depicted in the video. Due to the fact that, in a video, frames from the video are timed with frames of the subtitle stream, the encoding of workout control commands in a subtitle stream maintains synchronization of the video and of corresponding workout control commands in the video workout program.

This synchronization between a video and corresponding control commands in the video workout program can enable a user to become immersed in a workout on the exercise machine, which may help the user to avoid the boredom and burnout that is often experienced by users of exercise machines.

Further, in general, some example methods disclosed herein may enable live or prerecorded video workout programs on an exercise machine to be dynamically scaled based on heart rate monitoring. For example, due to the possibility that the fitness level of the user may be higher or lower than is optimal for the workout being performed by the trainer in the video of a video workout program, the actual heart rate of the user may be continuously monitored during the performance of the workout, and the difficulty level of the video workout program may be dynamically scaled during the performance of the workout to help the user maintain proper heart rate zones during the workout. By monitoring not only the user's current heart rate but also the direction and speed at which the user's heart rate is trending, the method may avoid changing the current difficulty level too often. Further, in some embodiments, the changes to the current difficulty level can be limited to avoid being changed too dramatically in order to avoid the current difficulty level experienced by the user from being dramatically different from the difficulty level that the user sees in the video. As a result of the current difficulty level not being changed too often and/or too dramatically, the enjoyment of the user may be increased, the inadvertent operation of the exercise machine at a level that is not optimal for the user's fitness level may be avoided, and the integrity between the workout of the trainer shown in the video and the actual workout performed by the user can be maintained, thus increasing the ability of the user to become more immersed in the workout on the exercise machine. Maintaining the integrity between the workout of the trainer shown in the video and the actual workout performed by the user may result, for example, in a trainer running but a user running at a faster or slower pace, but not walking or not sprinting.

In the exercise system disclosed herein, a video camera may be configured to communicate a video workout program over a network to be executed at, and to control, an exercise machine either directly or through any number of intermediate computer systems. For example, a remote server may be eliminated, and the video workout program may be transmitted over the network, after a video of the video workout program is encoded with exercise machine control commands, directly from a computer. In another example, both the remote server and the computer may be eliminated, and the encoding of the subtitle stream of the video with exercise machine control commands may occur at the video camera, resulting in the creation of a video workout program that is transmitted over the network directly from the video camera. In another example, another device, such as a wearable device worn by a videographer or worn by a trainer, may be used by the videographer or the trainer to encode the subtitle stream of the video to create a video workout program before the video workout program is transmitted over the network, and/or the encoding of the subtitle stream may occur automatically based on data gathered from sensors worn by the trainer, thus eliminating a producer from the production of the live video workout program or the prerecorded video workout program. In this example, the trainer may be a professional athlete (e.g., an NBA player), and the sensor(s) may be worn by the professional athlete during a professional sporting event (e.g., during an NBA playoff game), and the professional athlete's biometric data (e.g., heart rate data) may be encoded to allow a user at home to try to match their biometric data (e.g., heart rate) to the biometric data of the professional athlete. In another example, a local server may be eliminated, and the video workout program may be transmitted directly from the network to a console, or to a tablet where the tablet functions as a console or functions in connection with a console.

Further, in another example, the video workout program may be communicated to two devices, one to display the video, and another to control an exercise machine. In this example, a large television, a virtual reality (VR) or augmented reality (AR) headset, or some other device with a display may be configured to display the video of the video workout program, while another device such as a console may be configured to simultaneously control the exercise machine using the decoded exercise machine control commands from the subtitle stream of the video of the video workout program.

Also, in another example, the video camera may be configured to be operated by the trainer, thus eliminating the videographer.

Further, in another example, the video workout program may be broadcast to a single machine, such as in a one-on-one personalized workout session between a trainer and a user, or may be broadcast to multiple machines simultaneously, and multiple users may perform the pre-recorded video workout program, or the live video workout program, simultaneously. This may be useful in a gym setting where multiple users are in a group class and wish to perform the same workout together as a group. This simultaneous performance of a live video workout program or a pre-recorded video workout program may be performed on machines of the same type (e.g., all treadmills), or on machine of different types (e.g., some users on treadmills and some users on elliptical machines). Where the machines are of different types, the workout may include two sets of control commands that are individually relevant to a single type of machine, or may include a single set of control commands that may be used by both types of machines as relevant to each type of machine.

Also, although only a treadmill, elliptical machine, exercise bike, and rower machine are illustrated in the exercise system disclosed herein, it is understood that other types of exercise machines may be employed in the exercise system. For example, a cable weight machine or cable strength training machine (such as the NordicTrack Fusion CST machine), a stair climbing machine, or any other type of exercise machine may be employed.

Further, although some example heart rate zones disclosed herein are associated with particular ranges of heart rates, it is understood that a heart rate zone may be limited to smaller ranges of heart rates or to a single heart rate. Therefore, the term "zone" as used herein may encompass a single heart rate or a range of heart rates.

In the example frames, data, and CSV encodings disclosed herein, it is understood that the data gathered in the data charts are example data only, and other types of data may be additionally or alternatively gathered during the capturing of the video and/or during the creation of the video workout program. For example, precipitation data, temperature data, smell data, wind data, lighting data, and other types of data may be gathered during the capturing of the video. This data may then be encoded or included along with the exercise machine control commands, such as in the subtitle stream of the video in CSV encodings, to create the video workout program. Then, once decoded from the subtitle stream or otherwise accessed in the video workout program, this data may be employed automatically by an exercise machine to further create an immersive experience for a user of the exercise machine. For example, precipitation data may be employed to operate a mister, temperature data may be employed to operate a thermostat, smell data may be employed to operate a smell simulator, wind data may be employed to operate a fan, and/or lighting data may be employed to operate lighting, all in an effort to mimic, as much as possible, the remote environment of the workout depicted in the video of the video workout program once transmitted to the local location of the exercise machine. Other data may also be employed such as nutrition data that operates a smart food processor or food processor (e.g., a smart blender in connection with a smart refrigerator to make a particular protein shake with particular nutrients). In this manner, the user may further be immersed in the workout depicted in the video, which may help the user to forget any discomfort being experienced during the workout, and combat the boredom and burnout that is often experienced by users of exercise machines.

Further, although the workout depicted in the frames disclosed herein is an outdoor workout, any workout, whether indoors or outdoors, whether live or pre-recorded, and whether using an exercise machine or not using an exercise machine, may be depicted in the videos of the video workout programs disclosed herein. For example, a trainer may employ an exercise machine in a remote location to lead a group class in a studio workout at a local gym (or multiple group classes at multiple local gyms) of users exercising on the same type of exercise machine as the trainer. In this example, the video workout program may be a live video workout program or a pre-recorded video workout program, and the workout may be performed inside a building (e.g., in a workout studio) or outdoors. Further, although the workout depicted in the frames disclosed herein is a workout by a trainer, any person, whether a professional trainer or not, may perform the workout. For example, where two friends want to experience a workout in an exotic location (e.g., hiking Mount Everest), but only one of the friends has the money to make the trip, the second friend can experience the same workout at home on his treadmill as his friend experiences on his trip to the exotic location, using the methods disclosed herein.

Further, although the CSV encodings disclosed herein include nine (9) values, it is understood that CSV encoding may include greater than or less than nine (9) values. Further, values may be added over time as new control commands or other data becomes desirable to send to an exercise machine. Also, although a value of zero (0) is used to designate N/A in the CSV encodings disclosed herein, any other value, or no value at all, may be used instead to designate N/A in a CSV encoding. Further, although CSV encodings are disclosed herein as an example of how control commands and other data may be encoded in a subtitle stream, any other type of encoding, other than a CSV encoding, may be employed instead. For example, instead of values separated by a comma, values separated by some other delimiter may be employed. Further, other encodings that do not employ a delimiter may be employed.

Further, although the subtitle stream encodings disclosed herein are generally employed to encode control commands for exercise machines, it is understood that these subtitles stream encodings may additionally or alternatively be employed to encode control commands for other types of devices, such as televisions, smart appliances, automobile systems, environmental systems etc. For example, where a sporting event such as an NFL football game is broadcast over a television channel (e.g., NBC), the subtitle stream of the video depicting the marathon being broadcast may be encoded with control commands that: cause a couch vibration system to rumble and/or toss a user up when a big tackle occurs, cause a smart popcorn maker to make popcorn to be ready to eat at the end of each quarter or at the beginning of each commercial break, cause a scent device to emit a scent of grass or hotdogs to mimic smells in the NFL stadium depicted in the video, and cause a smart refrigerator pour a spectator a Coca-Cola in response to a user sending an indication of interest in a Coca-Cola commercial in the video back to the television channel (e.g., via a senor noticing interest by the user, such as a camera or biosensor, or via a manual indication by the user, such as a command to a smart speaker, or an indication on a smartphone app or website of the television station). Therefore, the subtitle stream encodings disclosed herein may be employed to control any device, such as to synchronize the automatic functioning of the device with the content depicted in the video.

Also, it is understood that the subtitle stream encodings disclosed herein may be secured to prevent a malicious third party from inserting malicious control commands into the subtitle stream encodings. For example, Amazon Web Services (AWS) may be employed to only accept video workout programs from a particular IP address. In this example, when control commands are embedded in a video of a video workout program, and then the resulting video workout program is sent to AWS from the particular IP address in an encrypted channel (with AWS holding the key to the encrypted channel), this may prevent AWS from accepting a malicious video workout program from another IP address and/or with another encryption scheme.

Further, although a video workout program is described herein as including a video and control commands that may cause an exercise machine to mimic the workout depicted in the video, it is understood that an exercise machine employing any of the methods disclosed herein may be configured to allow a user to seize control of the exercise machine during execution of the video workout program. For example, if the workout depicted in the video of the video workout program is too strenuous for a user, a user may opt to continue watching the video from the video workout program but cease to have the control commands continue to control the exercise machine. Therefore, control of a user's exercise machine by control commands of a video workout program may be overridden, either manually or automatically. In this example, a user may seize control of the exercise machine by selecting any of the standard controls of the exercise machine (e.g., the manual speed control), and may then again allow the video workout program to again control the exercise machine by selecting a "follow workout" control or a "follow trainer" control or a "follow video" control. In a first variation of this example, a video workout program executing on the exercise machine may continue to automatically scale the workout up and down, even though the user has manually modified a control of the workout, where the user has changed a control in the direction the user is supposed to be moving according to the video workout program (e.g., the user increases the speed where the video workout program is on the verge of doing so, or the user decreases the decline where video workout program is on the verge of doing so). In a second variation of this example, a video workout program executing on the exercise machine may continue to automatically scale the workout up and down to follow the workout depicted in the video, but may do so with the current difficulty level reset to the level set by the user. In a third variation of this example, the control by the video workout program executing on the exercise machine may be entirely overridden so that control of the exercise machine transfers entirely to the user, with no automatically scaling of the workout to follow the workout depicted in the video. In this third variation, with the control by the video workout program entirely overridden, the heart rate training widget may be disabled. Further, this third variation may result at any point during a video workout program where current heart rate data for the user becomes unavailable or unreliable for any reason, such as where a user removes their heart rate monitoring device (or never had it on in the first place), where the heart rate monitoring device is detected to be worn by another user or an animal (e.g., by a pet dog) or paired with the wrong exercise machine, or where their heart rate monitoring devices otherwise ceases to function properly for any other reason.

Some example embodiments may thus result in a personalized workout, which caters to the actual physiological response of the user to the workout, with hands-free adjustments to the workout being made on the fly. Further, some example embodiments enable a workout to adapt to current or recent conditions, as various current or recent factors can affect the heart rate of a user, such as current fitness level, recent sleep (or lack thereof), current dehydration or hydration levels, recent caffeine intake, current stress level, current fatigue level, current temperature, or current humidity level, or some combination thereof. For example, while a user's fitness level may not dramatically change day to day, other factors in a user's life can change day to day, and some embodiments may take those changes into account. For example, if a user is stressed, sleep deprived, dehydrated, or fatigued, the heart rate of the user may be faster than normal and the workout for the user may be automatically adjusted to be easier. In contrast, if the user is well rested, hydrated, and feeling fresh, the heart rate of the user may be slower than normal and the workout may be automatically adjusted to push the user harder. This may result in a workout that is not just catered to a user, but that is more specifically catered to the user on the particular day of the workout given the particular condition(s) of the user.

Some example embodiments can be employed with various types of workouts such as running, cycling, rowing, or other exercise machine workouts. Some example embodiments can avoid a user from overtraining by doing heart rate training more intelligently and may naturally force a user to progress as the fitness level of the user gradually increases, thus ensuring that a user increases a training load in a smart and meaningful way.

In some embodiments, the adaptive scaling of a video workout program by adjusting the current difficulty level may include adjusting multiple exercise machine parameters simultaneously. For example, in the case of a treadmill, the adaptive scaling of a video workout program may include simultaneously adjusting the current difficulty level of both a speed of a running belt and an incline percentage of a running deck. By adjusting multiple exercise machine parameters simultaneously in this manner, the integrity of the original workout depicted in the video may be better maintained and a more personalized workout may be performed by the user. For example, where a trainer is dramatically less fit than a user, in a video workout program in which the trainer is walking with a certain heart rate zone, the only way to get the user into that same heart rate zone or higher, while maintaining the integrity of the workout with the user walking rather than running, may be to dramatically increase the incline percentage of the running deck above the incline percentage at which the trainer performed their workout, rather than increasing the speed of the running belt much or at all. In this manner, both the trainer and the user are performing the workout by walking, but the dramatically more fit user is simply doing so at a high incline percentage than the dramatically less fit trainer. This may be due, at least in part, to a much greater loss in workout integrity due to the difference between walking and running versus walking at a lower incline percentage and walking at a higher incline percentage. In other words, while a user may easily notice a loss of workout integrity with the user running while the trainer is walking, the user may not be as likely to notice that their incline percentage is higher than the incline percentage of the trainer. An opposite example may also be implemented in a running video workout program, where the incline percentage of the running deck of the user is adjusted below (perhaps even to a negative incline percentage) the incline percentage at which the trainer performed their workout, rather than decreasing the speed of the running belt much or at all, to compensate for a dramatically les fit user. In this manner, both the trainer and the user are performing the workout by running, but the dramatically less fit user is simply doing so at a lower incline percentage than the dramatically more fit trainer.

In some embodiments, the adaptive scaling of a video workout program may include adjusting the current difficulty level of one or more exercise machine parameters and/or may include adjusting environmental factors that affect the difficulty of a workout. For example, the adjustment of environmental factors may include operation of a mister, adjustment of a thermostat, operation of a smell simulator, operation of a fan, and/or adjustment of lighting. Adjustment of each of these environmental factors may increase or decrease the difficulty of a video machine workout, and may be employed in a video machine workout in cooperation with, or instead of, the adjusting of the current difficulty level of one or more exercise machine parameters. Further, a user may be provided with personalization instructions during a video workout program that may affect the difficulty of the workout, such as instructions to hydrate, instructions to change the thermostat, instructions to operate a fan, or any other personalization or combination of personalizations.

In some embodiments, the adaptive scaling of a video workout program by adjusting the current difficulty level may include adjusting any exercise machine parameter related to difficulty using formulas employed to calculate the varying difficulty levels of a workout. For example, formulas may be employed to compute six difficulty levels that are easier than a baseline difficulty level, and six to twelve difficulty levels that are harder than the baseline difficulty level. Workouts will be scaled the same, regardless of exercise machine parameter limits. If an exercise machine parameter exceeds an exercise machine parameter limit, the exercise machine parameter may be set at a maximal exercise machine parameter limit.

In some embodiments, and in light of the possibility (or likelihood) that a user will perform a video workout program at a difficulty level other than the baseline difficulty level (e.g., different than the difficulty level of the trainer), the trainer depicted in the video of the video workout program may give verbal instructions in the video that are more directional than they are specific. For example, a trainer may explain that the workout will now be "increasing incline" rather than the workout will now be "increasing incline up to 10% incline." Thus, a trainer may not call out specific speeds, inclines, or resistances, but may call out more general revolutions per minute (RPM), strokes per minute (SPM), or rate of perceived exertion (RPE). A trainer may further make general statements in a video such as "I specifically picked the difficulty of this workout for you" or "I'll take this workout into account for the next workouts in the series" to give the trainer credit in the corresponding video workout program for the changes in the exercise machine control commands. The trainer in the video may also give verbal instructions that convey ideas such as "You can take control to adjust things if needed because you know yourself better than anyone," "If you need to take it easier today, just make one small adjustment and I'll handle the rest," "If you want an extra challenge today, make an adjustment and I'll handle the rest," "If you want to increase intensity, it might be better to increase intensity during the hard part of an interval, not the recovery," or "If you don't feel comfortable running faster than a certain pace, in the settings, feel free to set your max speed, and I'll make sure I don't take you beyond that." In some embodiments, a live video workout program may experience some natural lag between being recorded and broadcast and received and executed to control an exercise machine of a user. For example, this natural lag may be a few seconds long. In some embodiments, an artificial lag may also be introduced into a live video workout program. For example, an artificial lag of 10 seconds may be introduced into a live video workout program to allow for unexpected or unwanted video and/or audio to be edited out of the live video stream (e.g., to edit out audible obscenities uttered at a live event, or to edit out portions of a video that show visible obscenities). In either example, although this natural lag and/or artificial lag may cause a delay between the live event or class depicted in the video and the experience by the user, the user may nevertheless be watching the video so close in time to the actual events depicted that the user feels as though they are participating in the live event in real-time.

In some embodiments, the formulas for the various difficulty levels may be as follows, which correspond to a treadmill, an exercise bike, an elliptical machine, and a rower machine.

For a Treadmill (speed B of running belt):
$B_{-1}$=if (B>1, B−0.7^(5.1−B)−(0.8*(B/8)),B)
$B_{-2}$=if (B>1, B−0.7^(5.1−B)−(0.5*(B/8)), B)
$B_{-3}$=if (B>1, B−0.7^(5.1−B), B)
$B_{-4}$=if (B>1, B−0.7^(6−B), B)
$B_{-5}$=if (B>1, B−0.7^(7−B), B)
$B_{-6}$=if (B>1, B−0.7^(9−B), B)
$B_0$=B
$B_1$=if (B>1.4, 0.7^(9−B)+B, B)
$B_2$=if (B>1.4, 0.7^(7−B)+B, B)
$B_3$=if (B>1.4, 0.7^(6−B)+B, B)
$B_4$=if (B>1.4, 0.7^(5−B)+B, B)
$B_5$=if (B>1.4, 0.7^(4.2−B)+B, B)
$B_6$=if (B>1.4, 0.7^(3.5−B)+B, B)
$B_7$=if (B>4, 0.7^(2.6−B)+B, if (B>1.4, 0.7^(3.5−B)+B, B))
$B_8$=if (B>4, 0.7^(1.8−B)+B, if (B>1.4, 0.7^(3.5−B)+B, B))
$B_9$=if (B>4, 0.7^(1.2−B)+B, if (B>1.4, 0.7^(3.5−B)+B, B))
$B_{10}$=if (B>4, 0.7^(0.6−B)+B, if (B>1.4, 0.7^(3.5−B)+B, B))
$B_{11}$=if (B>4, 0.7^(−B)+B, if (B>1.4, 0.7^(3.5−B)+B, B))
$B_{12}$=if (B>4, 15, if (B>1.4, 0.7^(3.5−B)+B, B)) (note, the speed is set to 15 MPH for $B_{12}$ instead of 12 MPH, to provide for a treadmill that has a maximum speed of 15 MPH instead of 12 MPH)

Example, where baseline speed $B_0$=7.0 MPH, and equipment maximum speed is 12 MPH:
$B_{-6}$=4.3 MPH
$B_{-5}$=4.6 MPH
$B_{-4}$=5.0 MPH
$B_{-3}$=5.6 MPH
$B_{-2}$=6.0 MPH
$B_{-1}$=6.5 MPH
$B_0$=7.0 MPH
$B_1$=7.5 MPH
$B_2$=8 MPH
$B_3$=8.4 MPH
$B_4$=9 MPH
$B_5$=9.7 MPH
$B_6$=10.5 MPH
$B_7$=11.8 MPH
$B_8$=12 MPH (Note, these five last levels are set to the equipment maximum speed of 12 MPH)
$B_9$=12 MPH
$B_{10}$=12 MPH
$B_{11}$=12 MPH
$B_{12}$=12 MPH For a Treadmill (incline percentage C of running belt):
$C_{-6}$=if (B<4, (C>0, C−0.65*C, C), C)
$C_{-5}$=if (B<4, (C>0, C−0.55*C, C), C)
$C_{-4}$=if (B<4, (C>0, C−0.45*C, C), C)
$C_{-3}$=if (B<4, (C>0, C−0.35*C, C), C)
$C_{-2}$=if (B<4, (C>0, C−0.25*C, C), C)
$C_{-1}$=if (B<4, (C>0, C−0.15*C, C), C)
$C_0$=C
$C_1$=if (B<4, (C>0, 0.2*(40−C)/40*C+C, C), C)
$C_2$=if (B<4, (C>0, 0.4*(40−C)/40*C+C, C), C)
$C_3$=if (B<4, (C>0, 0.6*(40−C)/40*C+C, C), C)
$C_4$=if (B<4, (C>0, 0.8*(40−C)/40*C+C, C), C)
$C_5$=if (B<4, (C>0, (40−C)/40*C+C, C), C)
$C_6$=if (B<4, (C>0, 1.2*(40−C)/40*C+C, C), C)

Example, where baseline incline percentage is $C_0$=9%, and each incline percentage is rounded to the nearest 0.5%):
$C_{-6}$=3%
$C_{-5}$=4%
$C_{-4}$=5%
$C_{-3}$=6%
$C_{-2}$=7%
$C_{-1}$=7.5%
$C_0$=9%
$C_1$=10.5%
$C_2$=12%
$C_3$=13%
$C_4$=14.5%
$C_5$=16%
$C_6$=17.5%

For an Exercise Bike, an Elliptical Machine, or a Rower Machine (resistance R on the pedals, the handles, and/or the rowbar):
$R_{-6}$=if (if (R−6<1, 1, R−6)>24, 24, if (R−6<1, 1, R−6))
$R_{-5}$=if (if (R−5<1, 1, R−5)>24, 24, if (R−5<1, 1, R−5))
$R_{-4}$=if (if (R−4<1, 1, R−4)>24, 24, if (R−4<1, 1, R−4))
$R_{-3}$=if (if (R−3<1, 1, R−3)>24, 24, if (R−3<1, 1, R−3))
$R_{-2}$=if (if (R−2<1, 1, R−2)>24, 24, if (R−2<1, 1, R−2))
$R_{-1}$=if (if (R−1<1, 1, R−1)>24, 24, if (R−1<1, 1, R−1))
$R_0$=R
$R_1$=if (if (R+1<1, 1, R+1)>24, 24, if (R+1<1, 1, R+1))
$R_2$=if (if (R+2<1, 1, R+2)>24, 24, if (R+2<1, 1, R+2))

$R_3$=if (if (R+3<1, 1, R+3)>24, 24, if (R+3<1, 1, R+3))
$R_4$=if (if (R+5<1, 1, R+5)>24, 24, if (R+5<1, 1, R+5))
$R_5$=if (if (R+5<1, 1, R+5)>24, 24, if (R+5<1, 1, R+5))
$R_6$=if (if (R+6<1, 1, R+6)>24, 24, if (R+6<1, 1, R+6))
Example where baseline resistance on pedals is $R_0$=9:
$R_{-6}$=3
$R_{-5}$=4
$R_{-4}$=5
$R_{-3}$=6
$R_{-2}$=7
$R_{-1}$=8
$R_0$=9
$R_1$=10
$R_2$=11
$R_3$=12
$R_4$=13
$R_5$=14
$R_6$=15

In some embodiments, a starting difficulty level, other than the baseline difficulty level, may be determined for a user prior to beginning a video workout program. For example, after a user has completed at least a threshold number or workouts of at least a threshold duration (e.g., 3 workouts of a duration greater than 5 minutes), the data from these workouts, and possibly one or more other earlier workouts, may be analyzed (e.g., the past 7 completed workouts with a duration of more than 5 minutes may be analyzed, which may be around the last two weeks of workouts for some users). Outlier data may be excluded (especially low outliers instead of high outliers, because users don't tent over-exert beyond capability, but do tend to under-exert below capability), and the average data (e.g., average $VO_2$, average watts, average heart rate, or average heart rate recovery rate, or some combination thereof) of the workouts may be determined, and the closest difficulty level may be used as the starting difficulty level based on this average. In this manner, adjustments in difficulty level toward the beginning of a video workout program may be minimized. In other words, based on user history and behaviors, some embodiments may intelligently decide what level works best for the user, and as time progresses, some embodiments get smarter and learn more about the user. Scaled difficulty levels may be stored and labeled after being calculated for further use. For example, scaled difficulty levels may be stored and labeled based on the average $VO_2$ of the workout, according to the following formula:

$$(C_1+C_2+C_3+C_4+C_5+C_6+C_7)/M/*200/(T_1+T_2+T_3+T_4+T_5+T_6+T_7)=AVO_2$$

Where:
M=Mass (kg)
$AVO_2$=Average Relative $VO_2$ (ml/kg/sec)
C=Calorie Burn (kcal)
$C_1$=Calorie burn for most recent workout
$C_2$=Calorie burn for second most recent workout
$C_3$=Calorie burn for third most recent workout
Etc.
T=Time/Workout Duration (seconds)
$T_1$=Workout duration for most recent workout
$T_2$=Workout duration for second most recent workout
$T_3$=Workout duration for third most recent workout
Etc.

In one example, where a user has a mass of 68 kg and has a $VO_2$ of 0.453 ml/kg/sec, this formula may result in an $AVO_2$ of 0.453*68=30.8 $AVO_2$.

In some embodiments, calculating the average $VO_2$ of a workout may enable computation of the overall level at which the workout is programmed. For example, in the context of treadmill workouts, this may allow for basic differentiation between walking and running workouts as a whole. This may allow the targeting of different fitness levels with associated zones. For example, the Instantaneous $VO_2$ for every control set may be calculated according to the following formulas, which correspond to a treadmill, exercise bike, elliptical machine, and a rower machine:

For a Treadmill:
If S<1.8 m/s $$(0.1*S)+(1.8*S*G)+0.058333=VO_2 (ml/kg/sec)$$

Else if S>1.8 m/s $$(0.2*S)+(0.9*S*G)+0.058333=VO_2 (ml/kg/sec)$$

Where:
S=Speed (m/s)
G=Percent grade or incline (m/m)
Then, the average $VO_2$ may be calculated according to the following formula:

$$\Sigma(IVO_2*T)/\Sigma(T)=AVO_2 \text{ (ml/kg/sec)}$$

Where:
T=Time spent at that pace and grade or incline (sec)
$VO_2$=Instantaneous volume of oxygen consumed (ml/kg/sec)
$AVO_2$=Workout volume of oxygen consumed (ml/kg/sec)

For an Exercise Bike:

$$VO_2=(10.8*W/84)/60+0.11666667$$

Where:
W=Power (watts)
$VO_2$=Instantaneous volume of oxygen consumed (ml/kg/sec)
60=division from min to sec
0.11666667=$VO_2$ at rest (added to active $VO_2$)
84=default weight For an Elliptical Machine:

$$VO_2=1.15*(10.8*W/84)/60+0.11666667$$

Where:
W=Power (watts)
$VO_2$=Instantaneous volume of oxygen consumed (ml/kg/sec)
1.15=efficiency correction
60=division from min to sec
0.11666667=$VO_2$ at rest (added to active $VO_2$)
84=default weight For a Rower Machine:

$$W=(((RR/100)+(1-(RR/100))*0.25)*S*1.75)*5$$

$$VO_2=(0.20833*W+6.92)/84$$

Where:
W=Power (watts)
$VO_2$=Instantaneous volume of oxygen consumed (ml/kg/sec)
1.75 meters (5' 9")=default user height
84 kg (185 lbs.)=default user weight of Then, other formulas may be employed to compute different heart rate zone values for a user. This may be done by breaking up instantaneous V02 values into simple categories with a max and min. A heart rate zone may be calculated for every control set. Two different sets of heart rate zone values may be determined by the overall workout $VO_2$ ($AVO_2$). For example, first workouts may be divided by Average $VO_2$ and a zone may be assigned for each control set, according to the formulas below, which correspond to a treadmill, an exercise bike, an elliptical machine, and a rower machine:
For a Treadmill:
If $AVO_2 < 0.35$ ml/kg/sec
Compute Zones as such by INSTANTANEOUS $VO_2$ for each control set:
if instantaneous $VO_2 < 0.1$, Zone=0/-- (Not in a real zone)
$0.1 \geq VO_2 < 0.2$, Zone=1
$0.2 \geq VO_2 < 0.3$, Zone=2
$0.3 \geq VO_2 < 0.55$, Zone=3
$0.55 \geq VO_2 < 0.65$, Zone=4
$0.65 \geq VO_2$, Zone=5
If $AVO_2 \geq 0.35$ ml/kg/sec
Compute Zones as such:
if instantaneous $VO_2 < 0.15$, Zone=0/-- (Not in a real zone)
$0.15 \geq VO_2 < 0.35$, Zone=1
$0.35 \geq VO_2 < 0.6$, Zone=2
$0.6 \geq VO_2 < 0.7$, Zone=3
$0.7 \geq VO_2 < 0.85$, Zone=4
$0.85 \geq VO_2$, Zone=5
For an Exercise Bike:
Compute Zones as such by INSTANTANEOUS $VO_2$ for each control set:
if instantaneous $V02 < 0.2$, Zone=0/-- (Not in a real zone)
$0.2 \geq VO_2 < 0.35$, Zone=1
$0.35 \geq VO_2 < 0.45$, Zone=2
$0.45 \geq VO_2 < 0.6$, Zone=3
$0.6 \geq VO_2 < 0.7$, Zone=4
$0.7 \geq VO_2$, Zone=5
For an Elliptical Machine:
Compute Zones as such by INSTANTANEOUS $VO_2$ for each control set:
if instantaneous $VO_2 < 0.2$, Zone=0/-- (Not in a real zone)
$0.2 \geq VO_2 < 0.3$, Zone=1
$0.3 \geq VO_2 < 0.4$, Zone=2
$0.4 \geq VO_2 < 0.5$, Zone=3
$0.5 \geq VO_2 < 0.6$, Zone=4
$0.6 \geq VO_2$, Zone=5
For a Rower Machine:
Compute Zones as such by INSTANTANEOUS $VO_2$ for each control set:
if instantaneous $V02 < 0.2$, Zone=0/-- (Not in a real zone)
$0.2 \geq VO_2 < 0.35$, Zone=1
$0.35 \geq VO_2 < 0.45$, Zone=2
$0.45 \geq VO_2 < 0.6$, Zone=3
$0.6 \geq VO_2 < 0.7$, Zone=4
$0.7 \geq VO_2$, Zone=5

In some embodiments, these zone calculations may be used to estimates initial zones for a user, and then these initial estimated zones may be reviewed and fined tuned by a fitness professional. Further, in some embodiments, other zone calculations may be employed other than the zone calculations listed above.

Next, a zone may be assigned for cross-training sections as well. For example, workouts that have cross-training may have calorie multiplier metadata for sections of the workouts that have cross training. For these sections, the $VO_2$ may be computed accordingly. In these situations, the following calculations may be employed:
1. Compute $VO_2$ for interval with metadata.
2. Multiply that $VO_2$ by the calorie multiplier (just between the set time codes).
3. Use that to assign a zone.

Next, zone smoothing may be added according to the following formulas:

If $Z_0=Z_2$ AND $D<20$ AND $|VO2_{z0}-VO2_z|<0.1$, $Z=Z_0$

If $Z_0=Z_2$ AND $D \geq 20$, $Z=Z$ (no change)

If $Z_0 \neq Z_2$, $Z=Z$ (no change)

If $|VO2_{z0}-VO2_z|>0.1$, $Z=Z$ (no change)

Where:
$Z_0$=Previous Zone
$Z_2$=Subsequent Zone
D=Zone Duration

Next, corrective zone measures may be added according to the following formulas:

$$AZ = \text{if } (Z_0-Z>1, 1, 0)+Z$$

If zone of previous control set is more than one zone greater than the current calculated zone, add 1 to the zone
If not, use calculated zone.
Where:
AZ=Adjusted Zone
Z=Current Zone
PZ=Programmed Zone
$PZ_0$=Previous Programmed Zone
t=seconds after a programmed zone change
$t_0$=time of zone change
$t_5$=5 seconds after a zone change
T=seconds into the workout In some embodiments, in the context of a video workout program configured to be performed on a treadmill, an exercise bike, an elliptical machine, or a rower machine, the following zone evaluation may be performed to determine if the user is in the correct zone and to determine if a zone change is needed. This may be accomplished according to the following formula:

$$PZ-AZ=0$$

No action $$PZ-AZ>0$$

Potential to increase difficulty level $$PZ-AZ<0$$

Potential to decrease difficulty level
Where:
PZ=Programmed Zone (part of control set)
AZ=Actual Zone (based on actual user HR)

Continuing with the example context of a video workout program configured to be performed on a treadmill, an exercise bike, an elliptical machine, or a rower machine, there may be at least two different situations in which difficulty levels would need to be adjusted for a user. The first situation is when the user drifts out of the correct zone. The second situation is when the workout itself changes zones. Each of these two situations will now be explored.

Turning to the first situation in which the user drifts out of the correct zone, this situation may apply if a user experienced a zone change and made it to the correct zone but later is no longer in the correct zone. If the user never made it to the correct zone, or was only in the correct zone for less than a threshold time period (e.g., 5 seconds or 10 seconds), then the second situation criteria may be applied instead of the first situation criteria. The first situation may occur due to overcorrecting heart rate zones, or due to heart rate drift which is a phenomenon where, even at the same workload, a user's heart rate will steadily rise as they fatigue. In this first situation, the following sets of criteria may be employed, which correspond to a treadmill, an exercise bike, an elliptical machine, and a rower machine:

For a Treadmill:
Criteria Set 1:
If programmed zone lasts >25 sec
If user was in the correct zone for >5 sec consecutively
If >10 seconds remain in that programmed zone
If user is not in the correct zone
Then take Action 1: Immediately change level up or down if they leave the correct zone. (Only allow scale down event in first 180 seconds of workout, and 180 seconds following a pause event)
Criteria Set 2:
If T>180
If<10 seconds remain in that programmed zone
If user was in the correct zone for >5 sec consecutively
If user is not in the correct zone
Then take Action 2: Evaluate again after zone changes. (Do nothing)
Criteria Set 3:
If T>180
If programmed zone lasts <25 sec
If user was in the correct zone for >5 sec consecutively
If user is not in the correct zone
Then take Action 3: Evaluate again after zone changes (Do nothing)
Criteria Set 4:
If T>180
If user was in the correct zone for <5 sec consecutively
If user is not in the correct zone
Then take Action 4: Follow protocol for zone change
Criteria Set 5:
If T>180
If user is in the correct zone
If between $t_x$, $t_{x+10}$, $0<\Delta$ HR<4 BPM
If between $t_{x+10}$, $t_{x+2}$, $0<\Delta$ HR<4 BPM
User is still in correct zone
Then take Action 5: Immediately scale down
Criteria Set 6:
If T>180
If user is in the correct zone
If between $t_x$, $t_{x+10}$, $\Delta$ HR<-4 BPM
If between $t_{x+10}$, $t_{x+2}$, $\Delta$ HR<-4 BPM
User is still in correct zone
Then take Action 6: Immediately scale up For an Exercise Bike or an Elliptical Machine (RPM) or a Rower machine (SPM):
Criteria Set 1:
If programmed zone lasts >25 sec
If user was in the correct zone for >5 sec consecutively
If >10 seconds remain in that programmed zone
If user is no longer in the correct zone
If user revolutions per minute (RPM) is no more than 15 RPM less than programmed RPM/user strokes per minutes (SPM) is no more than 5 SPM less than programmed SPM
Then take Action 1: Immediately change level up or down if they leave the correct zone (Only allow scale down event in first 180 seconds of workout, and 180 seconds following a pause event)
Criteria Set 2:
If programmed zone lasts >25 sec
If user was in the correct zone for >5 sec consecutively
If >10 seconds remain in that programmed zone
If user is no longer in the correct zone
If user RPM is below prescribed RPM by more than 15 RPM/user SPM is below prescribed SPM by more than 5 SPM
Then take Action 1: Send message to increase RPM/SPM and evaluate again after zone changes (Do nothing)
Criteria Set 3:
If T>180
If<10 seconds remain in that programmed zone
If user was in the correct zone for >5 sec consecutively
If user is no longer in the correct zone
Then take Action 2: Evaluate again after zone changes (Do nothing)
Criteria Set 4:
If T>180
If programmed zone lasts <25 sec
If user was in the correct zone for >5 sec consecutively
If user is no longer in the correct zone
Then take Action 3: Evaluate again after zone changes (Do nothing)
Criteria Set 5:
If T>180
If user was in the correct zone for <5 sec consecutively
If user is no longer in the correct zone
Then take Action 4: Follow protocol for new zone Turning now to the second situation in which the workout itself changes zones, this situation may apply each time that a video workout program transitions from one zone to another during a workout. In some embodiments, the heart rates of the user during an initial time period after the change to a new zone (e.g., the first five seconds from $t_0$-$t_5$, or the first ten seconds from $t_0$-$t_{10}$) may be thrown out to allow for the heart rate of the user to react to a corresponding change in difficulty level. Oftentimes a peak heart rate will be seen in the first few seconds (e.g., the first five seconds, or the first 10 seconds) of the recovery period, and therefore it may be advantageous to throw out the first few seconds in order to avoid this peak heart rate from influencing changes in the difficulty level of the workout. Therefore, where the first five or ten seconds are thrown out, and the evaluation period is ten second, no scaling changes may take place for at least fifteen or twenty seconds after a zone change and/or a scale event. In some embodiments, the first fifteen seconds after a scale up event or a zone increase may be thrown out. In some embodiments, a slope of the user's heart rate may be evaluated every 10 seconds, and the appropriateness of scaling of the difficulty level may then be evaluated up to every 20 seconds. In this second situation, the following sets of criteria may be employed, which correspond to a treadmill, an exercise bike, an elliptical machine, and a rower machine:

For a Treadmill:
Criteria Set 1:
If T>180
If $PZ-PZ_0=1$
If programmed zone lasts >25 sec
If between $t_x$, $t_{x+10}$, $0<\Delta$ HR<4 BPM (starting at $t_5$, $t_{15}$)
If HR is below target zone
If >5 seconds remain in that programmed zone
If user is not yet in the correct zone (and wasn't in the correct zone for at least 5 sec) (their HR is still too low)
Then take Action 1: Immediately change level up
Criteria Set 2:
If $PZ-PZ_0=-1$ If programmed zone lasts >25 sec
If between $t_x$, $t_{x+10}$, $-4 < \Delta$ HR $< -2$ BPM (starting at $t_5$, $t_{15}$)
If HR is above target zone
If >5 seconds remain in that programmed zone
If user is not yet in the correct zone (and wasn't in the correct zone for at least 5 sec) (their HR is still too high)
Then take Action 2: Immediately change level down
Criteria Set 3:
  If $PZ-PZ_0 = -1$
  If programmed zone lasts >25 sec
  If between $t_x$, $t_{x+10}$, $-2 < \Delta$ HR $< 0$ BPM (starting at $t_5$, $t_{15}$)
  If HR is above target zone
  If >5 seconds remain in that programmed zone
  If user is not yet in the correct zone (and wasn't in the correct zone for at least 5 sec) (their HR is still too high)
  Then take Action 3: Immediately change two levels down
Criteria Set 4:
  If T>180
  If $PZ-PZ_0 > 2$
  If programmed zone lasts >25 sec
  If HR is below target zone
  If between $t_x$, $t_{x+10}$, $0 < \Delta$ HR $< 5$ BPM (starting at $t_5$, $t_{15}$)
  If >5 seconds remain in that programmed zone
  If user is not yet in the correct zone (and wasn't in the correct zone for at least 5 sec) (their HR is still too low)
  Then take Action 4: Immediately change level up
Criteria Set 5:
  If $PZ-PZ_0 < -2$
  If programmed zone lasts >25 sec
  If between $t_x$, $t_{x+10}$, $-5 < \Delta$ HR $< -3$ BPM (starting at $t_5$, $t_{15}$)
  If HR is above target zone
  If >5 seconds remain in that programmed zone
  If user is not yet in the correct zone (and wasn't in the correct zone for at least 5 sec) (their HR is still too high)
  Then take Action 5: Immediately change level down
Criteria Set 6:
  If $PZ-PZ_0 < -2$
  If programmed zone lasts >25 sec
  If between $t_x$, $t_{x+10}$, $-3 < \Delta$ HR $< 0$ BPM (starting at $t_5$, $t_{15}$)
  If HR is above target zone
  If >5 seconds remain in that programmed zone
  If user is not yet in the correct zone (and wasn't in the correct zone for at least 5 sec)(their HR is still too high)
  Then take Action 6: Immediately change 2 levels down
Criteria Set 7:
  If programmed zone lasts >25 sec
  If >5 seconds remain in that programmed zone
  If user is not in the correct zone
  Then take Action 7: Evaluate again after zone changes (Do nothing)
Criteria Set 8:
  If T>180
  If $PZ-PZ_0 = 1$
  If programmed zone lasts >25 sec
  If $\Delta$ HR between $t_x$, $t_{x+10} \geq 4$ BPM
  If HR is below target zone
  If >5 seconds remain in that programmed zone
  If user is not yet in the correct zone (their HR is still too low)
  Then take Action 8: Keep evaluating the rolling $\Delta$ HR to see if change is necessary (Do nothing)
Criteria Set 9:
  If T>180
  If $PZ-PZ_0 = 1$
  If programmed zone lasts >25 sec
  If HR is above target zone
  If >5 seconds remain in that programmed zone
  If user is not yet in the correct zone (their HR is still too low)
  Then take Action 9: Immediately scale workout down
Criteria Set 10:
  If T>180
  If $PZ-PZ_0 = -1$
  If programmed zone lasts >25 sec
  If $\Delta$ HR between $t_x$, $t_{x+10} \leq -4$ BPM
  If HR is above target zone
  If >5 seconds remain in that programmed zone
  If user is not yet in the correct zone (their HR is still too high)
  Then take Action 10: Keep evaluating the rolling $\Delta$ HR to see if change is necessary (Do nothing)
Criteria Set 11:
  If T>180
  If $PZ-PZ_0 = -1$
  If programmed zone lasts >25 sec
  If HR is below target zone
  If >5 seconds remain in that programmed zone
  If user is not yet in the correct zone (their HR is still too low)
  Then take Action 11: Immediately scale workout up
Criteria Set 12:
  If T>180
  If $PZ-PZ_0 \geq 2$
  If programmed zone lasts >25 sec
  If $\Delta$ HR between $t_x$, $t_{x+10} \geq 5$ BPM
  If HR is below target zone
  If >5 seconds remain in that programmed zone
  If user is not yet in the correct zone (their HR is still too low)
  Then take Action 12: Keep evaluating the rolling $\Delta$ HR to see if change is necessary (Do nothing)
Criteria Set 13:
  If T>180
  If $PZ-PZ_0 > 2$
  If programmed zone lasts >25 sec
  If HR is above target zone
  If >5 seconds remain in that programmed zone
  If user is not yet in the correct zone (their HR is still too high)
  Then take Action 13: Immediately scale workout down
Criteria Set 14:
  If T>180
  If $PZ-PZ_0 \leq -2$
  If programmed zone lasts >25 sec
  If $\Delta$ HR between $t_x$, $t_{x+10} \leq -5$ BPM
  If >5 seconds remain in that programmed zone
  If user is not yet in the correct zone (their HR is still too high)
  Then take Action 14: Keep evaluating the rolling $\Delta$ HR to see if change is necessary
Criteria Set 15:
  If T>180
  If $PZ-PZ_0 < -2$
  If programmed zone lasts >25 sec If HR is below target zone
If >5 seconds remain in that programmed zone
If user is not yet in the correct zone (their HR is still too low)
Then take Action 15: Immediately scale workout up
Criteria Set 16:
If user is in the correct zone
Then take Action 16: Do nothing
Criteria Set 17:
If T≤180
Then take Action 17: Follow logic for scale down event. If scale up event is triggered, ignore.
For an Exercise Bike or an Elliptical Machine (RPM) or a Rower machine (SPM):
Criteria Set 1:
If T>180
If $PZ-PZ_0=1$
If programmed zone lasts >25 sec
If between $t_x$, $t_{x+10}$, $0<\Delta$ HR<4 BPM (starting at $t_5$, $t_{15}$)
If >5 seconds remain in that programmed zone
If user is not yet in the correct zone (and wasn't in the correct zone for at least 5 sec) (their HR is still too low)
If user RPM is no more than 15 RPM less than programmed RPM/SPM is no more than 4 SPM less than programmed SPM (can be above)
Then take Action 1: Immediately change level up
Criteria Set 2:
If T>180
If $PZ-PZ_0=1$
If programmed zone lasts >25 sec
If between $t_x$, $t_{x+10}$, $0<\Delta$ HR<4 BPM (starting at $t_5$, $t_{15}$)
If >5 seconds remain in that programmed zone
If user is not yet in the correct zone (and wasn't in the correct zone for at least 5 sec) (their HR is still too low)
If user RPM is below prescribed RPM by more than 15 RPM/user SPM is below prescribed SPM by more than 4 SPM
Then take Action 2: Evaluate again after zone changes (Do nothing)
Criteria Set 3:
If $PZ-PZ_0=-1$
If programmed zone lasts >25 sec
If between $t_x$, $t_{x+10}$, $-4<\Delta$ HR<0 BPM (starting at $t_5$, $t_{15}$)
If >5 seconds remain in that programmed zone
If user is not yet in the correct zone (and wasn't in the correct zone for at least 5 sec) (their HR is still too high)
Then take Action 3: Immediately change level down
Criteria Set 4:
If T>180
If $PZ-PZ_0>2$
If programmed zone lasts >25 sec
If between $t_x$, $t_{x+10}$, $0<\Delta$ HR<5 BPM (starting at $t_5$, $t_{15}$)
If >5 seconds remain in that programmed zone
If user is not yet in the correct zone (and wasn't in the correct zone for at least 5 sec) (their HR is still too low)
If user RPM is no more than 15 RPM less than programmed RPM/SPM is no more than 5 SPM less than programmed SPM
Then take Action 4: Immediately change level up
Criteria Set 5:
If T>180
If $PZ-PZ_0\geq 2$
If programmed zone lasts >25 sec
If between $t_x$, $t_{x+10}$, $0<\Delta$ HR<5 BPM (starting at $t_5$, $t_{15}$)
If >5 seconds remain in that programmed zone
If user is not yet in the correct zone (and wasn't in the correct zone for at least 5 sec) (their HR is still too low)
If user RPM is below prescribed RPM by more than 15 RPM/user SPM is below prescribed SPM by more than 4 SPM
Then take Action 5: Evaluate again after zone changes (Do nothing)
Criteria Set 6:
If $PZ-PZ_0\leq -2$
If programmed zone lasts >25 sec
If between $t_x$, $t_{x+10}$, $-5<\Delta$ HR<0 BPM (starting at $t_5$, $t_{15}$)
If >5 seconds remain in that programmed zone
If user is not yet in the correct zone (and wasn't in the correct zone for at least 5 sec) (their HR is still too high)
Then take Action 6: Immediately change level down
Criteria Set 7:
If programmed zone lasts <25 sec
If >5 seconds remain in that programmed zone
If user is not in the correct zone
Then take Action 7: Evaluate again after zone changes (Do nothing)
Criteria Set 8:
If T>180
If $PZ-PZ_0=1$
If programmed zone lasts >25 sec
If $|\Delta$ HR$|$ between $t_x$, $t_{x+10}\geq 4$ BPM
If >5 seconds remain in that programmed zone
If user is not yet in the correct zone (their HR is still too low)
Then take Action 8: Keep evaluating the rolling $\Delta$ HR to see if change is necessary (Do nothing)
Criteria Set 9:
If T>180
If $PZ-PZ_0=-1$
If programmed zone lasts >25 sec
If $\Delta$ HR between $t_x$, $t_{x+10}\leq -4$ BPM
If >5 seconds remain in that programmed zone
If user is not yet in the correct zone (their HR is still too high)
Then take Action 9: Keep evaluating the rolling $\Delta$ HR to see if change is necessary (Do nothing)
Criteria Set 10:
If T>180
If $PZ-PZ_0>2$
If programmed zone lasts >25 sec
If $\Delta$ HR between $t_x$, $t_{x+10}\geq 5$ BPM
If >5 seconds remain in that programmed zone
If user is not yet in the correct zone (their HR is still too low)
Then take Action 10: Keep evaluating the rolling $\Delta$ HR to see if change is necessary
Criteria Set 11:
If T>180
If $PZ-PZ_0\leq -2$
If programmed zone lasts >25 sec
If $|\Delta$ HR$|$ between $t_x$, $t_{x+10}\leq -5$ BPM
If >5 seconds remain in that programmed zone
If user is not yet in the correct zone (their HR is still too high)
Then take Action 11: Keep evaluating the rolling $\Delta$ HR to see if change is necessary Criteria Set 12:
  If user is in the correct zone
  Then take Action 12: Do nothing.
Criteria Set 13:
  If T≤180
    Take Action 13: Follow logic for scale down event. If scale up event is triggered, ignore.
In some embodiments, the foregoing criteria may follow various guidelines with regard to starting a new video workout program and/or pausing a video workout program. These guidelines may include the following guidelines:
1. DO NOT scale up a workout in the first 180 seconds in order to allow a user's heart rate to increase on its own. Scaling in the first 180 seconds would likely overshoot the target.
2. DO NOT scale up a workout in the 180 seconds following a pause event in order to account for the likelihood that, when a user pauses the workout, they are likely going to have their heart rate drop due to the recovery.
3. DO allow scale down events to happen in the first 180 seconds of the workout in order to account for a warmup that is too challenging for the user.
4. DO allow scale down events to happen in the 180 seconds following a pause event.
5. DO NOT scale up for 60 seconds after a cross training section. A cross training section may have metadata with a calorie multiplier for that section.
6. DO NOT scale during a cross training section. A cross training section may have metadata with a calorie multiplier for that section.
7. DO NOT scale up for 60 seconds (for a treadmill) or 30 seconds (for an exercise bike, an elliptical machine, or a rower machine) after the dynamic scaling based on heart rate monitoring has been toggled back on by a user (after the smart scaling had previously been toggled off by a user, in some cases by the user overriding a setting).
8. DO NOT scale when last scale up event <25 seconds ago.
9. DO NOT scale when last scale down event <20 seconds ago.
10. DO NOT scale when a programmed zone increase <25 seconds ago.
11. DO NOT scale when a programmed zone decrease <20 seconds ago.
12. DO NOT scale if <5 seconds remains in a zone, and user is and was not in the zone.
13. DO NOT scale if<10 seconds remain in a zone, and user was in the zone (but isn't anymore).
14. DO NOT scale if PZ<25 seconds.
15. DO NOT scale if user pressed follow workout <60 seconds ago and HR is below PZ.
16. DO NOT scale if cross training ended <60 seconds ago and HR is below PZ.
17. DO NOT scale if workout is a cycling or elliptical workout and RPM values are invalid.
18. DO NOT scale if workout is a rowing workout and SPM values are invalid.
19. DO NOT scale if HR data is invalid.
20. DO NOT scale when levels are the same (example: when speed is at 1 mph, or at +6 to +12 walking speeds).
21. DO NOT scale up when equipment limits have been reached and HR is below the PZ.
22. DO NOT scale if a user is at a level that is maxing out the governor and HR is below PZ.
23. DO NOT scale if every data point in the array of last 10 seconds is the same value.
24. DO NOT scale if a user has changed controls in the last 60 seconds.
25. DO NOT scale when a user hops off of the running belt of a treadmill and hops onto to the side rails of the treadmill (e.g., to prevent a runaway treadmill) which may be detected in a number of ways including, but not limited to:
  Criteria Set 1:
    If last zone change was not a zone decrease
    If no scale down event for the last 30 seconds
    If Δ HR≤−4 bpm
    Then perform Actions 1: Do not send any scale up events, Pause workout, and
  Resume workout 2 levels lower
  Criteria Set 2:
    If last zone change was a zone decrease
    If zone decrease was at least 120 seconds ago
    If no scale down event for 30 seconds
    If Δ HR≤−4 bpm
    Then perform Actions 2: Do not send any scale up events, Pause workout, and
  Resume workout at previous level
  Criteria Set 3:
    If there was a scale down event within 30 seconds, OR
    If there was a zone decrease within 120 seconds (and no other changes since), OR
    If HR isn't dropping faster than 4 BPM per 10 seconds
    Then perform Action 3: Do nothing In some embodiments, outliers in heart rate data may be excluded in order to avoid dynamic scaling based on heart rate data that is likely invalid. For example, the following steps may be followed to exclude outlier heart rate data:
  Step 1: Is the value super wild?
  If HR>250, then exclude
  If HR<40, then exclude
  If 40<HR<250, then use as part of data set in step 2
  Note: Null values are treated like a 0 and are automatically excluded from the data set.
  Step 2: Is the value an outlier based on other data points around it?
  With the remaining values, take the median of the previous 10 seconds (or the array of the 10 seconds of data passed at the same time)
  If |HR−M|>20, exclude.
  Step 3: If ≤2 values are excluded, they are ignored when it comes to finding the A for scale events, OR if >2 values are excluded, do not trigger any scale event because it can be assumed that the data is bad.
  Where:
  HR=Instantaneous HR value
  M=Median of 10 second data set In one example that follows these steps for excluding outliers in heart rate data, with the following ten heart rate values: {123,123,146,125,122,122,121,121,121,120} and M=122, the following results may be obtained:
  $HR_1$=120, |120−122|=2, include
  $HR_2$=121, |121−122|=1, include
  $HR_3$=122, |122−122|=0, include
  $HR_4$=123, |123−122|=1, include
  $HR_5$=146, |146−122|=24, exclude In accordance with common practice, the various features illustrated in the drawings may not be drawn to scale. The illustrations presented in the present disclosure are not meant to be actual views of any particular apparatus (e.g., device, system, etc.) or method, but are merely example representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, it is understood that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner.

Further, any disjunctive word or phrase presenting two or more alternative terms, whether in the summary, detailed description, claims, or drawings, should be understood to contemplate the possibilities of including one of the terms, either of the terms, or both terms. For example, the phrase "A or B" should be understood to include the possibilities of "A" or "B" or "A and B."

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

The foregoing description, for purpose of explanation, has been described with reference to specific embodiments. However, the illustrative discussions above are not intended to be exhaustive or to limit the invention as claimed to the precise forms disclosed. Many modifications and variations are possible in view of the above teachings. The embodiments were chosen and described to explain practical applications, to thereby enable others skilled in the art to utilize the invention as claimed and various embodiments with various modifications as may be suited to the particular use contemplated.

The invention claimed is:

1. A method for controlling an exercise machine using a video workout program, the method comprising:
   receiving a subtitle stream of a video that has been encoded remotely from the exercise machine with exercise machine control commands to create the video workout program, wherein the exercise machine control commands are encoded at regular intervals based on a frame rate of the video;
   decoding, locally to the exercise machine, the subtitle stream of the video to access the exercise machine control commands;
   displaying, locally to the exercise machine, the video; and
   controlling, locally to the exercise machine, one or more moveable members of the exercise machine using the exercise machine control commands.

2. The method of claim 1, wherein the exercise machine control commands are encoded as comma separated values (CSVs).

3. The method of claim 2, wherein the CSVs further include workout data associated with a workout depicted in the video of the video workout program.

4. The method of claim 3, wherein the workout data includes one or more of:
   a target revolutions per minute (RPM) for the workout;
   a target watts for the workout;
   a target heart rate zone for the workout;
   a target heart rate for the workout;
   a current number of seconds since a start of the workout; and
   a workout state of the workout, the workout state including a warmup state, an in-workout state, or a cooldown state.

5. The method of claim 1, wherein:
   changes in the exercise machine control commands of the video workout program are synchronized with associated changes in the workout depicted in the video of the video workout program; and
   changes in the control of the one or more moveable members of the exercise machine occur synchronously with associated changes in the workout being displayed in the video.

6. The method of claim 1, wherein the exercise machine control commands are configured to control one or more of:
   a speed of the one or more moveable members of the exercise machine;
   an incline percentage of the one or more moveable members of the exercise machine; or
   a resistance of the one or more moveable members of the exercise machine.

7. The method of claim 2, wherein the exercise machine control commands are encoded such that values having different positions correspond to different parameters of the exercise machine.

8. A method for generating a video workout program for controlling an exercise machine, the method comprising:
  capturing, at a remote location that is remote from the exercise machine, a video that includes a depiction of a trainer performing a workout;
  encoding, at the remote location, exercise machine control commands into a subtitle stream of the video to create the video workout program, wherein the exercise machine control commands are encoded such that each second of the video is associated with an exercise control command of the exercise control commands; and
  transmitting the video workout program to the exercise machine, wherein the exercise machine is configured to decode the subtitle stream of the video to access the exercise machine control commands and execute the video workout program to control one or more moveable members of the exercise machine once per second using the exercise machine control commands and to continuously display the video.

9. The method of claim 8, wherein the exercise machine control commands are encoded as comma separated values (CSVs).

10. The method of claim 9, wherein the CSVs further include workout data associated with a workout depicted in the video of the video workout program.

11. The method of claim 10, wherein the workout data includes one or more of:
  a target revolutions per minute (RPM) for the workout;
  a target watts for the workout;
  a target heart rate zone for the workout;
  a target heart rate for the workout;
  a current number of seconds since a start of the workout; and
  a workout state of the workout, the workout state including a warmup state, an in-workout state, or a cooldown state.

12. The method of claim 8, wherein:
  changes in the exercise machine control commands of the video workout program are synchronized with associated changes in the workout depicted in the video of the video workout program; and
  changes in the control of the one or more moveable members of the exercise machine occur synchronously with associated changes in the workout being displayed in the video.

13. The method of claim 8, wherein the exercise machine control commands are configured to control one or more of:
  a speed of the one or more moveable members of the exercise machine;
  an incline percentage of the one or more moveable members of the exercise machine; or
  a resistance of the one or more moveable members of the exercise machine.

14. The method of claim 9, wherein the exercise machine control commands are encoded such that values having different positions correspond to different parameters of the exercise machine.

15. A non-transitory, computer-readable medium including instructions which, when executed by a processor of an exercise machine, cause the processor to:
  decode a subtitle stream of a video of a video workout program to access exercise machine control commands;
  execute, the video workout program to control one or more moveable members of the exercise machine once per second using the exercise machine control commands and to continuously display the video.

16. The computer-readable medium of claim 15, wherein the exercise machine control commands are encoded once per second.

17. The computer-readable medium of claim 15, wherein the exercise machine control commands are encoded as comma separated values (CSVs).

18. The computer-readable medium of claim 17, wherein the exercise machine control commands are encoded such that values having different positions correspond to different parameters of the exercise machine.

19. The computer-readable medium of claim 15, wherein:
  changes in the exercise machine control commands of the video workout program are synchronized with associated changes in the workout depicted in the video of the video workout program; and
  changes in the control of the one or more moveable members of the exercise machine occur synchronously with associated changes in the workout being displayed in the video.

20. The computer-readable medium of claim 18, wherein the exercise machine parameters include one or more of:
  a speed of the one or more moveable members of the exercise machine;
  an incline percentage of the one or more moveable members of the exercise machine; or
  a resistance of the one or more moveable members of the exercise machine.

* * * * *